US006074850A

United States Patent [19]
Antelman et al.

[11] Patent Number: 6,074,850
[45] Date of Patent: Jun. 13, 2000

[54] RETINOBLASTOMA FUSION POLYPEPTIDES

[75] Inventors: Douglas Antelman, Encinitas, Calif.; Richard J. Gregory, Westford, Mass.; Kenneth N. Wills, Encinitas, Calif.

[73] Assignee: Canji, Inc., San Diego, Calif.

[21] Appl. No.: 08/801,092

[22] Filed: Feb. 14, 1997

Related U.S. Application Data

[63] Continuation-in-part of application No. 08/751,517, Nov. 15, 1996, abandoned.

[51] Int. Cl.$^7$ .............................. C12P 21/04; C07H 21/04
[52] U.S. Cl. ...................... 435/69.7; 435/71.1; 536/23.4
[58] Field of Search .......................... 536/23.4; 435/69.7, 435/71.1

[56] References Cited

U.S. PATENT DOCUMENTS

| | | |
|---|---|---|
| 4,235,871 | 11/1980 | Papahadjopoulos et al. |
| 4,501,728 | 2/1985 | Geho et al. |
| 4,837,028 | 6/1989 | Allen |
| 5,019,369 | 5/1991 | Presant et al. |

FOREIGN PATENT DOCUMENTS

| | | |
|---|---|---|
| WO 92/06180 | 4/1992 | WIPO |
| WO 93/14188 | 7/1993 | WIPO |
| WO 93/19768 | 10/1993 | WIPO |
| WO 93/20221 | 10/1993 | WIPO |
| WO 94/06922 | 3/1994 | WIPO |
| WO 94/06923 | 3/1994 | WIPO |

OTHER PUBLICATIONS

Sellers et al. A Potent Transrepression Domain in the Retinoblastoma Protein Induces a Cell Cycle Arrest When Bound to E2F Sites PNAS (92)11544–48. 1995.

Chang et al. Cytostatic Gene Therapy for Vascular Proliferative Disorders with a Constitutively Active Form of Retinoblastoma Gene Product. Science (267)518–522, 1995.

Nakano et al. Transcriptional Regulatory Elements in the 5' Upstream and First Intron Region of the Human Smooth Muscle (Aortic Type)α–Actin–Encoding Gene. Gene (99)285–289. 1991.

Adams, P.D. et al., "Transcriptional control by E2F," *Cancer Biology* 6:99–108 (1995).

Adnane, J. et al., "The Retinoblastoma Susceptibility Gene Product Represses Transcription When Directly Bound to the Promoter," *J. Biol. Chem.* 270(15):8837–8843 (1995).

Antelman, D. et al., "Inhibition of tumor cell proliferation in vitro and in vivo by exogenous p110$^{RB}$, the retinoblastoma tumor suppressor protein," *Oncogene* 10:697–704 (1995).

Arteaga, C.L. et al., "Tissue–targeted Antinsense c–fos Retroviral Vector Inhibits Established Breast Cancer Xenografts in Nude Mice," *Cancer Research* 56:1098–1103 (1996).

Babajko, S. et al., "Interplay of the Liver–Enriched Trans-acting Factors, DBP and HNF1, in the Transactivation of Human IGFBP–1 Promoter," *Biochem. & Biophys. Research Commun.* 196(1):480–486 (1993).

Banas, B. et al., "Analysis of the promoter of the human prostatic acid phosphatase gene," *Biochim. Biophy. Acta* 1217:188–194 (1994).

Beijersbergen, R.L. et al., "E2F–4, a new member of the E2F gene family, has oncogenic activity and associates with p107 in vivo," *Genes & Devel.* 8:2680–2690 (1994).

Bingle, C.D. et al., "Interaction of CCAAT/enhancer–binding protein α and β with the rat caeruloplasmin gene promoter," *Biochem. J.* 294:473–479 (1993).

Bookstein, R. et al., "Suppression of Tumorigenicity of Human Prostate Carcinoma Cells by Replacing a Mutated RB Gene," *Science* 247:712–715 (1990).

Buck, V. et al., "Molecular and functional characterisation of E2F–5, a new member of the E2F family," *Oncogene* 11:31–38 (1995).

Clowes, A.W. et al., "Kinetics of Cellular Proliferation after Arterial Injury," *Lab. Invest.* 49(3) 327–333 (1983).

Cox, G.A. et al., "Overexpression of dystrophin in transgenic mdx mice eliminates dystrophic symptoms without toxicity," *Nature* 364:725–729 (1993).

Curiel, D.T. et al., "Adenovirus enhancement of transferrin–polylysine–mediated gene delivery," *Proc. Natl. Acad. Sci. U.S.A.* 88:8850–8854 (1991).

Dalesandro, J. et al., "Gene Therapy for Donor Hearts: Ex vivo Liposome–Mediated Transfection," *J. Thoracic and Cardiovascular Surgery* 111(2):416–422 (1996).

Dobrowolski, S.F. et al., "An E2F dominant negative mutant blocks E1A induced cell cycle progression," *Oncogene* 9:2605–2612 (1994).

Dowdy, S.F. et al., "Physical Interaction of the Retinoblastoma Protein with Human D Cyclins," *Cell* 73:499–511 (1993).

Dusetti, N.J. et al., "Structural Organization of the Gene Encoding the Rat Pancreatitis–associated Protein," *J. Biol. Chem.* 268(19):14470–14475 (1993).

Eisenberger, C.L. et al., "Differential Regulation of the Rat Phosphoenolpyruvate Carboxykinase Gene Expression in Several Tissues of Transgene Mice," *Mol. Cell Biol.* 12(3):1396–1403 (1992).

Fontaine, R.N. et al., "Structure of the Rat Pancreatic Cholesterol Esterase Gene," *Biochemistry* 30:7008–7014 (1991).

Forss–Petter, S. et al., "Transgenic Mice Expressing β–Galactosidase in Mature Neurons under Neuron–Specific Enolase Promoter Control," *Neuron* 5:187–197 (1990).

(List continued on next page.)

*Primary Examiner*—Paula K. Hutzell
*Assistant Examiner*—Lin Sun-Hoffman
*Attorney, Agent, or Firm*—Townsend and Townsend and Crew LLP

[57] ABSTRACT

Fusions of the transcription factor E2F and the retinoblastoma protein RB are provided, along with methods of treatment of hyperproliferative diseases.

18 Claims, 51 Drawing Sheets

(5 of 51 Drawing Sheet(s) Filed in Color)

OTHER PUBLICATIONS

French, B.A. et al., "Percutaneous Transluminal In Vivo Gene Transfer by Recombinant Adenovirus in Normal Porcine Coronary Arteries, Atherosclerotic Arteries, and Two Models of Coronary Restenosis," *Circulation* 90(5):2402–2413 (1994).

Friedman, J.M. et al., "Cellular Promoters Incorporated into the Adenovirus Genome: Cell Specificity of Albumin and Immunoglobin Expression," *Mol. Cell Biol.* 6(11):3791–3797 (1986).

Ginsberg, D. et al., "E2F–4, a new member of the E2F transcription factor family, interacts with p107," *Genes & Devel.* 8:2665–2679 (1994).

Gorman, C.M. et al., "Recombinant Genomes Which Express Chloramphenicol Acetyltransferase in Mammalian Cells," *Mol. Cell Biol.* 2(9):1044–1051 (1982).

Hanson, R.D. et al., "The 5'–Flanking Region of the Human CGL–1/Granzyme B Gene Targets Expression of a REporter Gene to Activated T–lymphocytes in Transgenic Mice," *J. Biol. Chem.* 266(36):24433–24438 (1991).

Hatzoglou, M. et al., "Hepatic Gene Transfer in Animals Using REtroviruses Containing the Promoter from the Gene for Phosphoenolpyruvate Carboxykinase," *J. Biol. Chem.* 265(28):17285–17293 (1990).

Helftenbein, G. et al., "Expression of the Uteroglobin Promoter in Epithelial Cell Lines from Endometrium," *Annals New York Acad. Sci.* Bulletti C. et al., eds., New York Academy of Sciences, New York, 622:69–79 (1991).

Hemstrom, C. et al., "Gene Product of Region E4 of Adenovirus Type 5 Modulates Accumulation of Certain Viral Polypeptides," *J. Virol.* 62(9):3258–3264 (1988).

Hiebert, S.W., "Regions of the Retinoblastoma Gene product Required for Its Interaction with the E2F Transcription Factor Are Necessary for E2 Promoter Repression and pRb–Mediated Growth Suppression," *Mol. Cell Biol.* 13(6):3384–3391 (1993).

Houchins, J.P. et al., "Genomic structure of nkg5, a human NK and T cell–specific activation gene," *Immunogenetics* 37:102–107 (1993).

Houglum, K. et al., "LAP (NF–IL6) Transactivates the Collagen $\alpha_1$(I) Gene from a 5' Regulatory Region," *J. Clin. Invest.* 94:808–814 (1994).

Huang, S. et al., "A cellular protein that competes with SV40 T antigen for binding to the retinoblastoma gene product," *Nature* 350:160–162 (1991).

Huber, B.E. et al., "Retroviral–mediated gene therapy for the treatment of hepatocellular carcinoma: An innovative approach for cancer therapy," *Proc. Natl. Acad. Sci. U.S.A.*, 88:8039–8043 (1991).

Ilantzis, C. et al., "Identification of a Human cancer Related Organ–Specific Neoantigen," *Microbiol. Immunol.* 37(2):119–128 (1993).

Ivey–Hoyle, M. et al., "Cloning and Characterization of E2F–2, a Novel Protein with the Biochemical Properties of Transcription Factor E2F," *Mol. Cell Biol.* 13(12):7802–7812 (1993).

Jahroudi, N. et al., "Endothelial–Cell–Specific Regulation of van Willebrand Factor Gene Expression," *Mol. Cell. Biol.* 14(2):999–1008 (1994).

Kaspar, F. et al., "Characterization of Two Point Mutations in the Androgen REceptor Gene of Patients with Perineoscrotal Hypospadia," *J. Steroid Biochem. Molec. Biol.* 47(1–6):127–135 (1993).

Kaye, F.J. et al., "A single–amino acid substitution results in a retinoblastoma protein defective in phosphorylation and oncoprotein binding," *Proc. Natl. Acad. Sci. U.S.A.* 87:6922–6926 (1990).

Keller, S.A. et al., "Regulation of amylase gene expression in diabetic mice is mediated by a cis–acting upstream element close to the pancreas–specific enhancer," *Genes & Devel.* 4:1316–1321 (1990).

Koc, O.N. et al., "Transfer of Drug Resistance Genes Into Hematopoietic Progenitors to Improve Chemotherapy Tolerance," *Seminars in Oncology* 23(1):46–65 (1996).

Krek, W. et al., "Negative REgulation of the Growth–Promoting Transcription Factor E2F–1 by a Stably Bound Cyclin A–Dependent Protein Kinase," *Cell* 78:161–172 (1994).

Krek, W. et al., "Cyclin A–Kinase Regulation of E2F–1 DNA Binding Function Underlies Suppression of an S Phase Checkpoint," *Cell* 83:1149–1158 (1995).

Kruse, F. et al., "An endocrine–specific element is an integral component of an exocrine–specific pancreatic enhancer," *Genes & Devel.* 7:774–786 (1993).

Lake, R.A. et al., "A 3' transcriptional enhancer regulates tissue–specific expression of the human CD2 gene," *EMBO J.* 9(10):3129–3136 (1990).

Lee, W.H. et al., "The retinoblastoma susceptibility gene encodes a nuclear phosphoprotein associated with DNA binding activity," *Nature* 329:642–645 (1987).

Lee, Y.H. et al., "Multiple, Functional DBP Sits on the promoter of the Cholesterol $7\alpha$–Hydroxlyase P450 Gene, CYP7," *J. Biol. Chem.* 269(20):14681–14689 (1994).

Li, S.P. et al., "cis–Acting Elements Responsible for Interleukin–6 Inducible C–reactive Protein Gene Expression," *J. Biol. Chem.* 265(7):4136–4142 (1990).

Lilja, H., "Structure, function, and regulation of the enzyme activity of prostate–specific antigen," *World J. Urol.* 11:188–191 (1993).

Lo, K. et al., "LyF–1, a Transcriptional Regulator That Interacts with a Novel Class of Promoters for Lymphocyte–Specific Genes," *Mol. Cell Biol.* 11(10):5229–5243 (1991).

Luskey, K.L., "Conservation of Promoter Sequence but Not Complex Intron Splicing Pattern in Human Hamster genes for 3–Hydroxy–3–Methylglutaryl Coenzyme A Reductase," *Mol. Cell Biol.* 7(5):1881–1893 (1987).

Makrov, S.S. et al., "Suppression of experimental arthritis by gene transfer of interleukin 1 receptor antagonist cDNA," *Proc. Natl. Acad. Sci. U.S.A.* 93:402–406 (1996).

Maxwell, I.H. et al., "Expression of the Diptheria Toxin A–Chain Coding Sequence under the Control of Promoters and Enhancers from Immunoglobulin Genes as a Means of Directing Toxicity to B–Lymphoid Cells," *Cancer Res.* 51:4299–4304 (1991).

Mendelzon, D. et al., "The binding site for the liver–specific transcription factor Tf–LF1 and the TATA box of the human transferrin gene promoter are the only elements necessary to direct liver specific transcription in vitro," *Nucl. Acids Res.* 18(19):5717–5721 (1990).

Nolet, S. et al., "Prostatic secretory protein $PSP_{94}$: gene organization and promoter sequence in Rhesus monkey and human," *Biochim. Biophys. Acta* 1089:247–249 (1991).

Nolta, J.A. et al., "Transduction of pluripotent human hematopoietic stem cells demonstrated by clonal analysis after engraftment in immune–deficient mice," *Proc. Natl. Acad. Sci. U.S.A.* 93:2414–2419 (1996).

Petropoulos, C.J. et al., "Using Avian Retroviral Vectors for Gene Therapy," *J. Virol.* 66(6):3391–3397 (1992).

Plank, C. et al., "The Influence of Endosome–disruptive Peptides on Gene Transfer Using Synthetic Virus–like Gene Transfer Systems," *J. Biol. Chem.* 269(17):12918–12924 (1994).

Qin, X.Q. et al., "Identification of a growth suppression domain within the retinoblastoma gene product," *Genes & Devel.* 6:953–964 (1992).

Raper, S.E. et al., "Safety and Feasibility of Liver–Directed Ex Vivo Gene Therapy for Homozygous Familial Hypercholesterolemia," *Annals. of Surgery* 223(2):116–126 (1996).

Reddy, S. et al., "Structure of the Human Smooth Muscle α–Actin Gene," *J. Biol. Chem.* 265(3):1683–1687 (1990).

Rice, D.A. et al., "Analysis of the Promoter Region of the Gene Encoding Mouse Cholesterol Side–chain Cleavage Enzyme," *J. Biol. Chem.* 265(20):11713–11720 (1990).

Rosenthal, N., "Identification of Regulatory Elements of Cloned Genes with Functional Assays," *Meth. of Enzymology* 152:704–720 (1987).

Schwartz, M.L. et al., "Brain–specific Enhancement of the Mouse Neurofilament Heavy Gene Promoter in Vitro," *J. Biol. Chem.* 269(18):13444–13450 (1994).

Sharkey, R.M. et al., "Phase I Clinical Evaluation of a New Murin Monoclonal antibody (Mu–9) against Colon–Specific Antigen–p for Targeting Gastrointestinal Carcinomas," *Cancer Supp.* 73(3):864–877 (1994).

Smith, J.R. et al., "Identification of Nucleotides Responsible for Enhancer Activity of Sterol Regulatory Element in Low Density Lipoprotein Receptor Gene," *J. Biol. Chem.* 265(4):2306–2310 (1990).

Svensson, E.C. et al., "Organization of the β–Galactoside α2, 6–Sialyltransferase Gene," *J. Biol. Chem.* 265(34):20863–20868 (1990).

Szoka, F. et al., "Comparative Properties and Methods of Preparation of Lipid Vesicles (Liposomes)," *Ann. Rev. Biophys. Bioeng.* 9:467–508 (1980).

Talamonti, M.S. et al., "Increase in Activity and Level of $pp60^{c-src}$ in Progressive Stages of Human Colorectal Cancer," *J. Clin. Invest.* 91:53–60 (1993).

Tamura, S. et al., "Sequence motif in control regions of the $H^+/K^+$ ATPase α and β subunit genes recognized by gastric specific nuclear protein(s)," *FEBS Lett.* 298(2,3):137–141 (1992).

Tanizawa, Y. et al., "Human Glucokinase Gene: Isolation, Structural Characterization, and Identification of a Microsatellite Repeat Polymorphism," *Mol. Endocrin.* 6(7):1070–1081 (1992).

Thean, E.T. et al., "Serum human α–lactalbumin as a marker for breast cancer," *Br. J. Cancer* 61:773–775 (1990).

Thimmappaya, B. et al., "Adenovirus VAI RNA Is Required for Efficient Translation of Viral mRNAs at Late Times after Infection," *Cell* 31:543–551 (1982).

Vairo, G. et al., "Functional interaction between E2F–4 and p130: evidence for distinct mecahnisms underlying growth suppression by different retinoblastoma protein family members," *Genes & Devel.* 9:869–881 (1995).

Weintraub, S.J. et al., "Retinoblastoma protein switches the E2F site from positive to negative element," *Nature* 358:259–261 (1992).

Wen, S.F. et al., "Retinoblastoma protein monoclonal antibodies with novel charateristics," *J. Immunol. Meth.* 169:231–240 (1994).

Willard, J.E. et al., "Genetic Modification of the Vessel Wall," *Circulation* 89(5):2190–2197 (1994).

Wills, K.N. et al., "Development and Characterization of Recombinant Adenoviruses Encoding Human p53 for Gene Therapy of Cancer," *Hum. Gene Therapy* 5:1079–1088 (1994).

Wills, K.N. et al., "Gene therapy for hepatocellular carcinoma: Chemosensitivity conferred by adenovirus–mediated transfer of the HSV–1 thymidine kinase gene," *Gene: Gene Therapy* 2(3):191–197 (1995).

Wu, C.L. et al., "In Vivo Association of E2F and DP Family Proteins," *Mol. Cell Biol.* 15(5):2536–2546 (1995).

Wu, G.Y. et al., "Receptor–mediated Gene Delivery and Expression in Vivo," *J. Biol. Chem.* 263(29):14621–14624 (1988).

Wu, K.J. et al., "Transactivation of Pancreas–Specific Gene Sequences in Somatic Cell Hybrids," *Mol. Cell Biol.* 11(9):4423–4430 (1991).

Xu, G. et al., "Multiple members of the E2F transcription factor family are the products of oncogenes," *Proc. Natl. Acad. Sci. U.S.A.* 92:1357–1361 (1995).

Shimizu, R.T. et al., "The Smooth Muscle α–Actin Gene Promoter Is Differentially Regulated in Smooth Muscle versus Non–smooth Muscle Cells," *J. Biol. Chem.* 270(13):7631–7643 (1995).

```
         10         20         30         40         50         60
MALAGAPAGG PCAPALEALL GAGALRLLDS SQIVIISAAQ DASAPPAPTG PAAPAAGPCD 70         80         90        100        110        120
PDLLLFATPQ APRPTPSAPR PALGRPPVKR RLDLETDHQY LAESSGPARG RGRHPGKGVK 130        140        150        160        170        180
SPGEKSRYET SLNLTTKRFL ELLSHSADGV VDLNWAAEVL KVQKRRIYDI TNVLEGIQLI 190        200        210        220        230        240
AKKSKNHIQW LGSHTTVGVG GRLEGLTQDL RQLQESEQQL DHLMNICTTQ LRLLSEDTDS 250        260        270        280        290        300
QRLAYVTCQD LRSIADPAEQ MVMVIKAPPE TQLQAVDSSE NFQISLKSKQ GPIDVFLCPE 310        320        330        340        350        360
ETVGGISPGK TPSQEVTSEE ENRATDSATI VSPPPSSPPS SLTTDPSQSL LSLEQEPLLS 370        380        390        400        410        420
RMGSLRAPVD EDRLSPLVAA DSLLEHVRED FSGLLPEEFI SLSPPHEALD YHFGLEEGEG 430        440        450        460        470        480
IRDLFDCDFG DLTPLDF*..  .......... .......... .......... ..........
```

FIG. 1A

|  10 | 20 | 30 | 40 | 50 | 60 |
|---|---|---|---|---|---|
| GGAATTCCGT | GGCCGGGACT | TTGCAGGCAG | CGGCGGCCGG | GGGCGGAGCG | GGATCGAGCC |
| 70 | 80 | 90 | 100 | 110 | 120 |
| CTCGCCGAGG | CCTGCCGCCA | TGGGCCCGCG | CCGCCGCCGC | CGCCTGTCAC | CCGGGCCGCG |
| 130 | 140 | 150 | 160 | 170 | 180 |
| CGGGCCGTGA | GCGTCATGGC | CTTGGCCGGG | GCCCCTGCGG | GCGGCCCATG | CGCGCCGGCG |
| 190 | 200 | 210 | 220 | 230 | 240 |
| CTGGAGGCCC | TGCTCGGGGC | CGGCGCGCTG | CGGCTGCTCG | ACTCCTCGCA | GATCGTCATC |
| 250 | 260 | 270 | 280 | 290 | 300 |
| ATCTCCGCCG | CGCAGGACGC | CAGCGCCCCG | CCGGCTCCCA | CCGGCCCCGC | GGCGCCCGCC |
| 310 | 320 | 330 | 340 | 350 | 360 |
| GCCGGCCCCT | GCGACCCTGA | CCTGCTGCTC | TTCGCCACAC | CGCAGGCGCC | CCGGCCCACA |
| 370 | 380 | 390 | 400 | 410 | 420 |
| CCCAGTGCGC | CGCGGCCCGC | GCTCGGCCGC | CCGCCGGTGA | AGCGGAGGCT | GGACCTGGAA |
| 430 | 440 | 450 | 460 | 470 | 480 |
| ACTGACCATC | AGTACCTGGC | CGAGAGCAGT | GGGCCAGCTC | GGGGCAGAGG | CCGCCATCCA |
| 490 | 500 | 510 | 520 | 530 | 540 |
| GGAAAAGGTG | TGAAATCCCC | GGGGGAGAAG | TCACGCTATG | AGACCTCACT | GAATCTGACC |
| 550 | 560 | 570 | 580 | 590 | 600 |
| ACCAAGCGCT | TCCTGGAGCT | GCTGAGCCAC | TCGGCTGACG | GTGTCGTCGA | CCTGAACTGG |
| 610 | 620 | 630 | 640 | 650 | 660 |
| GCTGCCGAGG | TGCTGAAGGT | GCAGAAGCGG | CGCATCTATG | ACATCACCAA | CGTCCTTGAG |
| 670 | 680 | 690 | 700 | 710 | 720 |
| GGCATCCAGC | TCATTGCCAA | GAAGTCCAAG | AACCACATCC | AGTGGCTGGG | CAGCCACACC |
| 730 | 740 | 750 | 760 | 770 | 780 |
| ACAGTGGGCG | TCGGCGGACG | GCTTGAGGGG | TTGACCCAGG | ACCTCCGACA | GCTGCAGGAG |
| 790 | 800 | 810 | 820 | 830 | 840 |
| AGCGAGCAGC | AGCTGGACCA | CCTGATGAAT | ATCTGTACTA | CGCAGCTGCG | CCTGCTCTCC |
| 850 | 860 | 870 | 880 | 890 | 900 |
| GAGGACACTG | ACAGCCAGCG | CCTGGCCTAC | GTGACGTGTC | AGGACCTTCG | TAGCATTGCA |
| 910 | 920 | 930 | 940 | 950 | 960 |
| GACCCTGCAG | AGCAGATGGT | TATGGTGATC | AAAGCCCCTC | CTGAGACCCA | GCTCCAAGCC |
| 970 | 980 | 990 | 1000 | 1010 | 1020 |
| GTGGACTCTT | CGGAGAACTT | TCAGATCTCC | CTTAAGAGCA | ACAAGGCCC | GATCGATGTT |
| 1030 | 1040 | 1050 | 1060 | 1070 | 1080 |
| TTCCTGTGCC | CTGAGGAGAC | CGTAGGTGGG | ATCAGCCCTG | GAAGACCCC | ATCCCAGGAG |
| 1090 | 1100 | 1110 | 1120 | 1130 | 1140 |
| GTCACTTCTG | AGGAGGAGAA | CAGGGCCACT | GACTCTGCCA | CCATAGTGTC | ACCACCACCA |
| 1150 | 1160 | 1170 | 1180 | 1190 | 1200 |
| TCATCTCCCC | CCTCATCCCT | CACCACAGAT | CCCAGCCAGT | CTCTACTCAG | CCTGGAGCAA |
| 1210 | 1220 | 1230 | 1240 | 1250 | 1260 |
| GAACCGCTGT | TGTCCCGGAT | GGGCAGCCTG | CGGGCTCCCG | TGGACGAGGA | CCGCCTGTCC |

FIG. 1B

```
        1270       1280       1290       1300       1310       1320
   CCGCTGGTGG CGGCCGACTC GCTCCTGGAG CATGTGCGGG AGGACTTCTC CGGCCTCCTC 1330       1340       1350       1360       1370       1380
   CCTGAGGAGT TCATCAGCCT TTCCCCACCC CACGAGGCCC TCGACTACCA CTTCGGCCTC 1390       1400       1410       1420       1430       1440
   GAGGAGGGCG AGGGCATCAG AGACCTCTTC GACTGTGACT TTGGGGACCT CACCCCCCTG 1450       1460       1470       1480       1490       1500
   GATTTCTGAC AGGGCTTGGA GGGACCAGGG TTTCCAGAGT AGCTCACCTT GTCTCTGCAG 1510       1520       1530       1540       1550       1560
   CCCTGGAGCC CCCTGTCCCT GGCCGTCCTC CCAGCCTGTT TGGAAACATT TAATTTATAC 1570       1580       1590       1600       1610       1620
   CCCTCTCCTC TGTCTCCAGA AGCTTCTAGC TCTGGGGTCT GGCTACCGCT AGGAGGCTGA 1630       1640       1650       1660       1670       1680
   GCAAGCCAGG AAGGGAAGGA GTCTGTGTGG TGTGTATGTG CATGCAGCCT ACACCCACAC 1690       1700       1710       1720       1730       1740
   GTGTGTACCG GGGGTGAATG TGTGTGAGCA TGTGTGTGTG CATGTACCGG GGAATGAAGG 1750       1760       1770       1780       1790       1800
   TGAACATACA CCTCTGTGTG TGCACTGCAG ACACGCCCCA GTGTGTCCAC ATGTGTGTGC 1810       1820       1830       1840       1850       1860
   ATGAGTCCAT CTCTGCGCGT GGGGGGGCTC TAACTGCACT TTCGGCCCTT TTGCTCGTGG 1870       1880       1890       1900       1910       1920
   GGTCCCACAA GGCCCAGGGC AGTGCCTGCT CCCAGAATCT GGTGCTCTGA CCAGGCCAGG 1930       1940       1950       1960       1970       1980
   TGGGGAGGCT TTGGCTGGCT GGGCGTGTAG GACGGTGAGA GCACTTCTGT CTTAAAGGTT 1990       2000       2010       2020       2030       2040
   TTTTCTGATT GAAGCTTTAA TGGAGCGTTA TTTATTTATC GAGGCCTCTT TGGTGAGCCT 2050       2060       2070       2080       2090       2100
   GGGGAATCAG CAAAAGGGGA GGAGGGGTGT GGGGTTGATA CCCCAACTCC CTCTACCCTT 2110       2120       2130       2140       2150       2160
   GAGCAAGGGC AGGGGTCCCT GAGCTGTTCT TCTGCCCCAT ACTGAAGGAA CTGAGGCCTG 2170       2180       2190       2200       2210       2220
   GGTGATTTAT TTATTGGGAA AGTGAGGGAG GGAGACAGAC TGACTGACAG CCATGGGTGG 2230       2240       2250       2260       2270       2280
   TCAGATGGTG GGGTGGGCCC TCTCCAGGGG GCCAGTTCAG GGCCCAGCTG CCCCCCAGGA 2290       2300       2310       2320       2330       2340
   TGGATATGAG ATGGGAGAGG TGAGTGGGGG ACCTTCACTG ATGTGGGCAG GAGGGGTGGT 2350       2360       2370       2380       2390       2400
   GAAGGCCTCC CCCAGCCCAG ACCCTGTGGT CCCTCCTGCA GTGTCTGAAG CGCCTGCCTC 2410       2420       2430       2440       2450       2460
   CCCACTGCTC TGCCCCACCC TCCAATCTGC ACTTTGATTT GCTTCCTAAC AGCTCTGTTC 2470       2480       2490       2500       2520       2520
   CCTCCTGCTT TGGTTTTAAT AAATATTTTG ATGACGTTAA AAAAAGGAAT TCGATAT
```

*FIG. 1B*
(CONTINUED)

```
   1 ttccggtttt tctcagggga cgttgaaatt attttttgtaa cgggagtcgg gagaggacgg
  61 ggcgtgcccc gcgtgcgcgc gcgtcgtcct ccccggcgct cctccacagc tcgctggctc
 121 ccgccgcgga aaggcgtcat gccgcccaaa accccccgaa aaacggccgc caccgccgcc
 181 gctgccgccg cggaaccccc ggcaccgccg ccgccgcccc ctcctgagga ggacccagag
 241 caggacagcg gcccggagga cctgcctctc gtcaggcttg agtttgaaga aacagaagaa
 301 cctgattttta ctgcattatg tcagaaatta agataccag atcatgtcag agagagagct
 361 tggttaactt gggagaaagt ttcatctgtg gatggagtat tgggaggtta tattcaaaag
 421 aaaaaggaac tgtggggaat ctgtatcttt attgcagcag ttgacctaga tgagatgtcg
 481 ttcacttttta ctgagctaca gaaaaacata gaaatcagtg tccataaatt ctttaactta
 541 ctaaaagaaa ttgataccag taccaaagtt gataatgcta tgtcaagact gttgaagaag
 601 tatgatgtat tgtttgcact cttcagcaaa ttggaaagga catgtgaact tatatatttg
 661 acacaaccca gcagttcgat atctactgaa ataaattctg cattggtgct aaaagtttct
 721 tggatcacat ttttattagc taaagggaaa gtattacaaa tggaagatga tctggtgatt
 781 tcatttcagt taatgctatg tgtccttgac tatttttatta aactctcacc tcccatgttg
 841 ctcaaagaac catataaaac agctgttata cccattaatg gttcacctcg aacacccagg
 901 cgaggtcaga acaggagtgc acggatagca aacaactag aaaatgatac aagaattatt
 961 gaagttctct gtaaagaaca tgaatgtaat atagatgagg tgaaaaatgt ttatttcaaa
1021 aattttatac cttttatgaa ttctcttgga cttgtaacat ctaatggact tccagaggtt
1081 gaaaatcttt ctaaacgata cgaagaaatt tatcttaaaa ataaagatct agatgcaaga
1141 ttattttttgg atcatgataa aactcttcag actgattcta tagacagttt tgaaacacag
1201 agaacaccac gaaaaagtaa ccttgatgaa gaggtgaatg taattcctcc acacactcca
1261 gttaggactg ttatgaacac tatccaacaa ttaatgatga ttttaaattc agcaagtgat
1321 caaccttcag aaaatctgat ttcctatttt aacaactgca cagtgaatcc aaaagaaagt
1381 atactgaaaa gagtgaagga tataggatac atcttttaaag agaaatttgc taaagctgtg
1441 ggacagggtt gtgtcgaaat tggatccacag cgatacaaac ttggagttcg cttgtattac
1501 cgagtaatgg aatccatgct taaatcagaa gaagaacgat tatccattca aaatttttagc
1561 aaacttctga atgacaacat ttttcatatg tctttattgg cgtgcgctct tgaggttgta
1621 atggccacat atagcagaag tacatctcag aatcttgatt ctggaacaga tttgtctttc
1681 ccatggattc tgaatgtgct taatttaaaa gcctttgatt tttacaaagt gatcgaaagt
1741 tttatcaaag cagaaggcaa cttgacaaga gaaatgataa aacatttaga acgatgtgaa
1801 catcgaatca tggaatccct tgcatggctc tcagattcac ctttatttga tcttattaaa
1861 caatcaaagg accgagaagg accaactgat caccttgaat ctgcttgtcc tcttaatctt
1921 cctctccaga taatcacac tgcagcagat atgtatcttt ctcctgtaag atctccaaag
1981 aaaaaaggtt caactacgcg tgtaaattct actgcaaatg cagagacaca agcaacctca
2041 gccttccaga cccagaagcc attgaaatct acctctcttt cactgttttta taaaaagtg
2101 tatcggctag cctatctccg gctaaataca ctttgtgaac gccttctgtc tgagcaccca
2161 gaattagaac atatcatctg gacccttttc cagcacaccc tgcagaatga gtatgaactc
2221 atgagagaca ggcatttgga ccaaattatg atgtgttcca tgtatggcat atgcaaagtg
2281 aagaatatag accttaaatt caaaatcatt gtaacagcat acaaggatct tcctcatgct
2341 gttcaggaga cattcaaacg tgttttgatc aaagaagagg agtatgattc tattatagta
2401 ttctataact cggtcttcat gcagagactg aaaacaaata ttttgcagta tgcttccacc
2461 aggcccccta ccttgtcacc aatacctcac attcctcgaa gcccttacaa gtttcctagt
2521 tcacccttac ggattcctgg agggaacatc tatatttcac ccctgaagag tccatataaa
2581 atttcagaag gtctgccaac accaacaaaa atgactccaa gatcaagaat cttagtatca
2641 attggtgaat cattcgggac ttctgagaag ttccagaaaa taaatcagat ggtatgtaac
2701 agcgaccgtg tgctcaaaag aagtgctgaa ggaagcaacc ctcctaaacc actgaaaaaa
2761 ctacgctttg atattgaagg atcagatgaa gcagatggaa gtaaacatct cccaggagag
2821 tccaaatttc agcagaaact ggcagaaatg acttctactc gaacacgaat gcaaaagcag
2881 aaaatgaatg atagcatgga tacctcaaac aaggaagaga atgaggatc tcaggacctt
2941 ggtggacact gtgtacacct ctggattcat tgtctctcac agatgtgact gtat
```

FIG. 2A

"MPPKTPRKTAATAAAAAAEPPAPPPPPPPEEDPEQDSGPEDLPL
VRLEFEETEEPDFTALCQKLKIPDHVRERAWLTWEKVSSVDGVLGGYIQKKKELWGIC
IFIAAVDLDEMSFTFTELQKNIEISVHKFFNLLKEIDTSTKVDNAMSRLLKKYDVLFA
LFSKLERTCELIYLTQPSSSISTEINSALVLKVSWITFLLAKGEVLQMEDDLVISFQL
MLCVLDYFIKLSPPMLLKEPYKTAVIPINGSPRTPRRGQNRSARIAKQLENDTRIIEV
LCKEHECNIDEVKNVYFKNFIPFMNSLGLVTSNGLPEVENLSKRYEEIYLKNKDLDAR
LFLDHDKTLQTDSIDSFETQRTPRKSNLDEEVNVIPPHTPVRTVMNTIQQLMMILNSA
SDQPSENLISYFNNCTVNPKESILKRVKDIGYIFKEKFAKAVGQGCVEIGSQRYKLGV
RLYYRVMESMLKSEEERLSIQNFSKLLNDNIFHMSLLACALEVVMATYSRSTSQNLDS
GTDLSFPWILNVLNLKAFDFYKVIESFIKAEGNLTREMIKHLERCEHRIMESLAWLSD
SPLFDLIKQSKDREGPTDHLESACPLNLPLQNNHTAADMYLSPVRSPKKKGSTTRVNS
TANAETQATSAFQTQKPLKSTSLSLFYKKVYRLAYLRLNTLCERLLSEHPELEHIIWT
LFQHTLQNEYELMRDRHLDQIMMCSMYGICKVKNIDLKFKIIVTAYKDLPHAVQETFK
RVLIKEEEYDSIIVFYNSVFMQRLKTNILQYASTRPPTLSPIPHIPRSPYKFPSSPLR
IPGGNIYISPLKSPYKISEGLPTPTKMTPRSRILVSIGESFGTSEKFQKINQMVCNSD
RVLKRSAEGSNPPKPLKKLRFDIEGSDEADGSKHLPGESKFQQKLAEMTSTRTRMQKQ
KMNDSMDTSNKEEK"

*FIG. 2B*

```
                                  >HincII
                                    |
                                  >AccI
                                    ||
            >BglII                >SalI
              |                    |||
       10     |    20        30    |||    40         50           60
    *    *    |    *    *     *    |||*    *    *    *    *    *    *
   GACGGATCGG GAGATCTCCC GATCCCCTAT GGTCGACTCT CAGTACAATC TGCTCTGATG >AlwNI
                     |
                     |
        70           80          90         100         110         120
    *    *    *    *    *    *    *    *    *    *    *    *
   CCGCATAGTT AAGCCAGTAT CTGCTCCCTG CTTGTGTGTT GGAGGTCGCT GAGTAGTGCG >ApoI                                     >MfeI
     |                                         |
     |130         140         150         160  |      170         180
    *|   *    *    *    *    *    *    *    *  |  *    *    *    *
   CGAGCAAAAT TTAAGCTACA ACAAGGCAAG GCTTGACCGA CAATTGCATG AAGAATCTGC >HincII
                                                                   |
                                                      >AflIII      |
                                                        |          |
                                            >NruI     >MluI        |
                                              |         |          |
        190         200         |210         220        |  230     |
    *    *    *    *    *    *  |  *    *    *    *     | *        |*
   TTAGGGTTAG GCGTTTTGCG CTGCTTCG CGA TGT ACG GGC CAG ATA TAC GCG TTG
                                    Arg Cys Thr Gly Gln Ile Tyr Ala Leu>
                                   __d___d___CMV PROMOTER___d___d___>

>SpeI      >AseI
                |         |
       240     250        | 260         270         280
    *    *    *    |*    *   |  *    *    *    *    *
   ACA TTG ATT ATT GAC TAG TTA TTA ATA GTA ATC AAT TAC GGG GTC ATT
   Thr Leu Ile Ile Asp *** Leu Leu Ile Val Ile Asn Tyr Gly Val Ile>
   __d___d___d___d___d___d_CMV PROMOTER__d___d___d___d___d___d___>

290         300         310         320         330
    *    *    *    *    *    *    *    *    *    *    *
   AGT TCA TAG CCC ATA TAT GGA GTT CCG CGT TAC ATA ACT TAC GGT AAA
   Ser Ser *** Pro Ile Tyr Gly Val Pro Arg Tyr Ile Thr Tyr Gly Lys>
   __d___d___d___d___d___d_CMV PROMOTER__d___d___d___d___d___d___>

>BglI                                         >AatII
                |                                              |
       340     350         360         370                     |
    *    *    *    *    *    *    *    *    *
   TGG CCC GCC TGG CTG ACC GCC CAA CGA CCC CCG CCC ATT GAC GTC AAT
   Trp Pro Ala Trp Leu Thr Ala Gln Arg Pro Pro Pro Ile Asp Val Asn>
   __d___d___d___d___d___d_CMV PROMOTER__d___d___d___d___d___d___>

380         390         400         410         420
    *    *    *    *    *    *    *    *    *    *
   AAT GAC GTA TGT TCC CAT AGT AAC GCC AAT AGG GAC TTT CCA TTG ACG
   Asn Asp Val Cys Ser His Ser Asn Ala Asn Arg Asp Phe Pro Leu Thr>
   __d___d___d___d___d___d_CMV PROMOTER__d___d___d___d___d___d___>
```

*FIG. 4*

```
>AatII                                          >BglI
 |                                               |
 430         440        450         460  |       470
 | *     *        *        *        *  | *         *        *
 TCA ATG GGT GGA CTA TTT ACG GTA AAC TGC CCA CTT GGC AGT ACA TCA
 Ser Met Gly Gly Leu Phe Thr Val Asn Cys Pro Leu Gly Ser Thr Ser>
 ___d___d___d___d___d___d_CMV PROMOTER__d___d___d___d___d___d___>

>NdeI                              >AatII
          |                                  |
  480     |     490        500        510|          520
    *     | *        *        *        * |  *          *
 AGT GTA TCA TAT GCC AAG TAC GCC CCC TAT TGA CGT CAA TGA CGG TAA
 Ser Val Ser Tyr Ala Lys Tyr Ala Pro Tyr * Arg Gln * Arg ***>
 ___d___d___d___d___d___d_CMV PROMOTER__d___d___d___d___d___d___>

>BglI
              |
      530     |     540        550         560        570
    *     *   | *        *        *          *        *        *
 ATG GCC CGC CTG GCA TTA TGC CCA GTA CAT GAC CTT ATG GGA CTT TCC
 Met Ala Arg Leu Ala Leu Cys Pro Val His Asp Leu Met Gly Leu Ser>
 ___d___d___d___d___d___d_CMV PROMOTER__d___d___d___d___d___d___>

>BsaAI                  >NcoI
                            |                       |
                          >SnaBI               >StyI    >MslI
                            |                   |        |
         580        590        600        610   |
       *        *        *        *        *        *        *
 TAC TTG GCA GTA CAT CTA CGT ATT AGT CAT CGC TAT TAC CAT GGT GAT
 Tyr Leu Ala Val His Leu Arg Ile Ser His Arg Tyr Tyr His Gly Asp>
 ___d___d___d___d___d___d_CMV PROMOTER__d___d___d___d___d___d___>

620          630        640         650        660
  *        *        *        *        *        *        *        *
 GCG GTT TTG GCA GTA CAT CAA TGG GCG TGG ATA GCG GTT TGA CTC ACG
 Ala Val Leu Ala Val His Gln Trp Ala Trp Ile Ala Val *** Leu Thr>
 ___d___d___d___d___d___d_CMV PROMOTER__d___d___d___d___d___d___>

>AatII                  >BanI
                                   |                       |
 670          680        690       | 700        710        |
   *        *        *        *  | *        *        *        *
 GGG ATT TCC AAG TCT CCA CCC CAT TGA CGT CAA TGG GAG TTT GTT TTG
 Gly Ile Ser Lys Ser Pro Pro His *** Arg Gln Trp Glu Phe Val Leu>
 ___d___d___d___d___d___d_CMV PROMOTER__d___d___d___d___d___d___>

720        730        740        750        760
       *        *        *        *        *        *
 GCA CCA AAA TCA ACG GGA CTT TCC AAA ATG TCG TAA CAA CTC CGC CCC
 Ala Pro Lys Ser Thr Gly Leu Ser Lys Met Ser *** Gln Leu Arg Pro>
 ___d___d___d___d___d___d_CMV PROMOTER__d___d___d___d___d_-d_-->

770        780        790        800        810
       *        *        *        *        *        *
 ATT GAC GCA AAT GGG CGG TAG GCG TGT ACG GTG GGA GGT CTA TAT AAG
 Ile Asp Ala Asn Gly Arg *** Ala Cys Thr Val Gly Gly Leu Tyr Lys>
 ___d___d___d___d___d___d_CMV PROMOTER__d___d___d___d___d___d___>
```

FIG. 4
(CONTINUED)

```
            >BanII
               |
            >SacI
               |
          >BsiHKAI
               |
       >Ecl136II
           | |
         | 820         830         840         850
        *|  |  *    *     *     *     *     *     *     *     *
        CAG AGC TCT CTG GCT AAC TAG AGA ACC CAC TGC TTA CTG GCT TAT CGA
        Gln Ser Ser Leu Ala Asn *** Arg Thr His Cys Leu Leu Ala Tyr Arg>
        ___d___d___d___d___d___d_CMV PROMOTER__d___d___d___d___d___d___>

>KpnI
                                                                 |
                          >BsaI                          >Acc65I|
                            |                                |  |
        >AseI             >SfcI        >HindIII          >BanI  |
          |                | |            |                 |   |
          >T7_PROMOTER     | |            |                 |   |
          |  |             | |            |                 |   |
        860 |    | 870     || 880        890        900 |   | 910
          *  |*     *    *|   *      *     *     *     *|     *
        AAT T AATACGA CTCACTATAG GGAGACCCAA GCTTCGCGCG GGTACCACTC
        Asn Xxx>
        ___d _>                                                  _____>

>PflMI
                                   |
                              >PvuII|
                                 |  |
        >EarI                 >MspAII|      >BanII
           |                     |  |          |
           | 920         930     | 940 |    | 950         960         970
          *|   *     *     *    |*     |*     *     *     *     *     *
        TCTTCCGCAT CGCTGTCTGC GAGGGCCAGC TGTTGGGCTC GCGGTTGAGG ACAAACTCTT
        _____e_____TRIPARTITE LEADER SEQUENCE_____e_____>
        >EarI          >ScaI
           |              |
           |  980      | 990        1000        1010        1020        1030
           |  *     *     *     *     *     *     *     *     *     *     *
        CGCGGTCTTT CCAGTACTCT TGGATCGGAA ACCCGTCGGC CTCCGAACGG TACTCCGCCA
        _____e_____TRIPARTITE LEADER SEQUENCE_____e_____>

>SfcI
                                                                     |
                                                                >MspAII
                                                                    ||
                                                    >XhoI       >BsiEI
                                                       |           |||
                                                  >PaeR71   >EaeI| ||
                                                       |        | |||
        >PpuMI                  >BsiEI            >BsoBI   >NotI| |||
           |                       |                 |        | |||
        >Eco0109I               >BsaWI             >AvaI   >EagI| |||
           |                       ||                 |        | |||
           |1040        1050       1060        1070    | 1080   |  | 1090
          *|   *     *     *     *||*     *     *     *     *   |*  || *
        CCGAGGGACC TGAGCGAGTC CGCATCGACC GGATCGGAAA ACCTCTCGAG GCGGCCGCTG
        _____TRIPARTITE LEADER SEQUENCE_____e___>

FIG. 4
                          (CONTINUED)
```

```
                                            >ApaI
                                              |
                          >ClaI    >EcoO109I
                            |        | | |
     >XbaI  >ApoI          >EcoRV|  >Bsp120I    >SfcI
       |      |              | |   | | |         |
    >PstI  >EcoRI  >BsiWI      >BspDI | |>BanII              >MslI
      | |    |      |        | |    | | |                     |
      | |  1100  |  1110     | 1120 | | |1130    |   1140     |
      | |*     * |      *    |    * | |  *  |      *        *
    CAGTCTAGAC GAATTCGCGT ACGATATCGA TGGGCCCTAT T CTA TAG TGT CAC CTA
                                                 Leu *** Cys His Leu>
                                                  ___SP6 PROMOTER___>

>BanII
                    |
                 >BsiHKAI
                    |
                  >SacI
                    |
        >Ecl136II| >BclI
            | |    |
    >BGH_POLY_A |  |
          |   | |  |
        1150  | |1160 |     1170       1180       1190       1200
           *  |  * | | *      |  *        *         *         *
    AAT G CTAGAGCTCG CTGATCAGCC TCGACTGTGC CTTCTAGTTG CCAGCCATCT
    Asn>
    ___>
                                                >BanI
                                                  |
         1210       1220       1230       1240  | 1250       1260
           *    *     *    *     *    *     *    *     *    *
    GTTGTTTGCC CCTCCCCCGT GCCTTCCTTG ACCCTGGAAG GTGCCACTCC CACTGTCCTT 1270       1280       1290       1300       1310       1320
           *    *     *    *     *    *     *    *     *    *     *
    TCCTAATAAA ATGAGGAAAT TGCATCGCAT TGTCTGAGTA GGTGTCATTC TATTCTGGGG
                                                >BbsI
                                                  |
         1330       1340       1350       1360  | 1370       1380
           *    *     *    *     *    *     *    |*    *    *    *
    GGTGGGGTGG GGCAGGACAG CAAGGGGGAG GATTGGGAAG ACAATAGCCG AAATGACCGA

>BsssI
                           |
                         >BspMI
                           |
         1390       1400 | 1410       1420       1430       1440
           *    *    *   * |*    *      *    *     *    *     *
    CCAAGCGACG CCCAACCTGC CATCACGAGA TTTCGATTCC ACCGCCGCCT TCTATGAAAG >NaeI
                                  |
                                >BsrFI
                                  | |
                                >BpmI|
                                  | |

>NgoMI
                                  | |
         1450       1460       1470 |      1480       1490       1500
           *    *    *    *     |*  |        *    *     *    *     *
    GTTGGGCTTC GGAATCGTTT TCCGGGACGC CGGCTGGATG ATCCTCCAGC GCGGGGATCT
```

FIG. 4
(CONTINUED)

```
                                    >BpmI
                                     |
                         >SV40_early_poly_A
                                     |
         1510        1520     |1530        1540        1550        1560
       *     *     *     *    *|    *     *     *     *     *     *     *
    CATGCTGGAG  TTCTTCGCCC  ACCCCAACTT  GTTTATTGCA  GCTTATAATG  GTTACAAATA >ApoI                                  >BsmI
               |                                      |
         1570  |1580        1590        1600        |1610        1620
       *    *  *|   *     *     *     *     *     *|    *     *     *
    AAGCAATAGC  ATCACAAATT  TCACAAATAA  AGCATTTTTT  TCACTGCATT  CTAGTTGTGG >HincII
                                                |
                                    >Bst1107I  >AccI
                                         |      ||
                                      >AccI    >SalI
                                         ||    |||
         1630        1640        1650       1660  |||  1670        1680
       *     *     *     *     *     *    *  ||*   ||*    *     *     *
    TTTGTCCAAA  CTCATCAATG  TATCTTATCA  TGTCTGTATA  CCGTCGACCT  CTAGCTAGAG
                                                                        ___>
                                                      >BsrBI
                                                         |
         1690        1700        1710        1720        1730        1740
       *     *     *     *     *     *     *     *     *    |*    *     *
    CTTGGCGTAA  TCATGGTCAT  AGCTGTTTCC  TGTGTGAAAT  TGTTATCCGC  TCACAATTCC
    _____c_____PUC19 BACKBONE H3 TO AATII_____c_____>

>BanI
                                                      |
         1750        1760        1770        1780   |  1790        1800
       *     *     *     *     *     *     *     *  |   *     *     *
    ACACAACATA  CGAGCCGGAA  GCATAAAGTG  TAAAGCCTGG  GGTGCCTAAT  GAGTGAGCTA
    _____c_____PUC19 BACKBONE H3 TO AATII_____c_____>

>AseI
       |
         1810        1820        1830        1840        1850        1860
       *   |*    *     *     *     *     *     *     *     *     *     *
    ACTCACATTA  ATTGCGTTGC  GCTCACTGCC  CGCTTTCCAG  TCGGGAAACC  TGTCGTGCCA
    _____c_____PUC19 BACKBONE H3 TO AATII_____c_____>

>PvuII
     |
    >MspAlI   >AseI       >EaeI                                    >HaeII
     |         |           |                                         |
     |   1870  |1880        1890        1900        1910        |  1920
     |   *   | *   *|   *     *     *     *     *     *     *     *
    GCTGCATTAA  TGAATCGGCC  AACGCGCGGG  GAGAGGCGGT  TTGCGTATTG  GGCGCTCTTC
               _____c_____PUC19 BACKBONE H3 TO AATII_____c_____>

>EarI
     |
    >SapI                            >BsiEI                 >BsrBI
     |                                 |                       |
     |   1930        1940        1950  |  1960        1970        1980
     |   *     *     *     *     *   | *     *     *     *     *     *
    CGCTTCCTCG  CTCACTGACT  CGCTGCGCTC  GGTCGTTCGG  CTGCGGCGAG  CGGTATCAGC
               _____c_____PUC19 BACKBONE H3 TO AATII_____c_____>

FIG. 4
                                  (CONTINUED)
```

```
                                                          >AflIII
                                                            |
       1990        2000        2010        2020        2030      | 2040
     *    *      *    *      *    *      *    *      *    *    * |  *
   TCACTCAAAG  GCGGTAATAC  GGTTATCCAC  AGAATCAGGG  GATAACGCAG  GAAAGAACAT
   _____c_____PUC19 BACKBONE H3 TO AATII_____c_____>

2050        2060        2070        2080        2090        2100
     *    *      *    *      *    *      *    *      *    *      *    *
   GTGAGCAAAA  GGCCAGCAAA  AGGCCAGGAA  CCGTAAAAAG  GCCGCGTTGC  TGGCGTTTTT
   _____c_____PUC19 BACKBONE H3 TO AATII_____c_____>

>DrdI
                                                  |
       2110        2120        2130        2140   | 2150        2160
     *    *      *    *      *    *      *    *   *   *      *    *
   CCATAGGCTC  CGCCCCCCTG  ACGAGCATCA  CAAAAATCGA  CGCTCAAGTC  AGAGGTGGCG
   _____c_____PUC19 BACKBONE H3 TO AATII_____c_____>

>BsssI
                                                            |
       2170        2180        2190        2200        2210        2220
     *    *      *    *      *    *      *    *      *    *      *    *
   AAACCCGACA  GGACTATAAA  GATACCAGGC  GTTTCCCCCT  GGAAGCTCCC  TCGTGCGCTC
   _____c_____PUC19 BACKBONE H3 TO AATII_____c_____>

>BsaWl
                        |
       2230        2240 | 2250        2260        2270        2280
     *    *      *    * | *    *      *    *      *    *      *    *
   TCCTGTTCCG  ACCCTGCCGC  TTACCGGATA  CCTGTCCGCC  TTTCTCCCTT  CGGGAAGCGT
   _____c_____PUC19 BACKBONE H3 TO AATII_____c_____>

>HaeII        >SfcI
     |            |
     | 2290        2300  | 2310        2320        2330        2340
   * |  *      *    *    | *    *      *    *      *    *      *    *
   GGCGCTTTCT  CAATGCTCAC  GCTGTAGGTA  TCTCAGTTCG  GTGTAGGTCG  TTCGCTCCAA
   _____c_____PUC19 BACKBONE H3 TO AATII_____c_____>

>BsiHKAI            >MspAlI
                 |                    |
     >ApaLI|                   >BsiEI        >BsaWI
        |  |                    |  |            |
       2350 |  | 2360        2370   2380        2390        2400
     *    * |  *    *      *    *  * |  |*      *    *      *    *
   GCTGGGCTGT  GTGCACGAAC  CCCCCGTTCA  GCCCGACCGC  TGCGCCTTAT  CCGGTAACTA
   _____c_____PUC19 BACKBONE H3 TO AATII_____c_____>

>AlwNI
                                                            |
       2410        2420        2430        2440        2450 | 2460
     *    *      *    *      *    *      *    *      *    * |*   *
   TCGTCTTGAG  TCCAACCCGG  TAAGACACGA  CTTATCGCCA  CTGGCAGCAG  CCACTGGTAA
   _____c_____PUC19 BACKBONE H3 TO AATII_____c_____>

>SfcI
                                        |
       2470        2480        2490     | 2500        2510        2520
     *    *      *    *      *    *     |*   *      *    *      *    *
   CAGGATTAGC  AGAGCGAGGT  ATGTAGGCGG  TGCTACAGAG  TTCTTGAAGT  GGTGGCCTAA
   _____c_____PUC19 BACKBONE H3 TO AATII_____c_____>
```

FIG. 4
(CONTINUED)

```
              2530        2540        2550        2560        2570        2580
                *           *           *           *           *           *
           CTACGGCTAC  ACTAGAAGGA  CAGTATTTGG  TATCTGCGCT  CTGCTGAAGC  CAGTTACCTT
           _____c_____PUC19 BACKBONE H3 TO AATII_____c_____>

>Eco57I                                   >MspAlI
            |                                         |
            | 2590       2600        2610        2620 | 2630       2640
            *  *         *  *        *  *        *  * |*  *        *  *
           CGGAAAAAGA  GTTGGTAGCT  CTTGATCCGG  CAAACAAACC  ACCGCTGGTA  GCGGTGGTTT
           _____c_____PUC19 BACKBONE H3 TO AATII_____c_____>

2650        2660        2670        2680        2690        2700
                *           *           *           *           *           *
           TTTTGTTTGC  AAGCAGCAGA  TTACGCGCAG  AAAAAAAGGA  TCTCAAGAAG  ATCCTTTGAT
           _____c_____PUC19 BACKBONE H3 TO AATII_____c_____>

>BspHI
                                                                            |
              2710        2720        2730        2740        2750        | 2760
                *           *           *           *           *         | *
           CTTTTCTACG  GGGTCTGACG  CTCAGTGGAA  CGAAAACTCA  CGTTAAGGGA  TTTTGGTCAT
           _____c_____PUC19 BACKBONE H3 TO AATII_____c_____>

>DraI                  >DraI
                                          |                      |
              2770        2780        2790 |2800        2810    | 2820
                *           *           * | *           *        *  *
           GAGATTATCA  AAAAGGATCT  TCACCTAGAT  CCTTTTAAAT  TAAAAATGAA  GTTTTAAATC
           _____c_____PUC19 BACKBONE H3 TO AATII_____c_____>

>BanI
                                                                            |
              2830        2840        2850        2860        2870        | 2880
                *           *           *           *           *         | *
           AATCTAAAGT  ATATATGAGT  AAACTTGGTC  TGACAGTTAC  CAATGCTTAA  TCAGTGAGGC
                                                                  a     AMP-ORF  >
           _____c_____PUC19 BACKBONE H3 TO AATII_____c_____>

>Ahdl
                                                               |
              2890        2900        2910        2920        2930        2940
                *           *           *           *           *           *
           ACCTATCTCA  GCGATCTGTC  TATTTCGTTC  ATCCATAGTT  GCCTGACTCC  CCGTCGTGTA
           _____a_____a_____AMP-ORF_____a_____a_____>
           _____c_____PUC19 BACKBONE H3 TO AATII_____c_____>

>BsaI
                                                                   |
                                                          >BsrDI   >BpmI
                                                            |       |
              2950        2960        2970        2980        2990 |    3000
                *           *           *           *           *  | *
           GATAACTACG  ATACGGGAGG  GCTTACCATC  TGGCCCCAGT  GCTGCAATGA  TACCGCGAGA
           _____a_____a_____AMP-ORF_____a_____a_____>
           _____c_____PUC19 BACKBONE H3 TO AATII_____c_____>

>BsrFl                                            >BGlI
            |                                                 |
            | 3010       3020        3030        3040        3050        3060
            *  *         *  *        *  *        *  *        *  *        *  *
           CCCACGCTCA  CCGGCTCCAG  ATTTATCAGC  AATAAACCAG  CCAGCCGGAA  GGGCCGAGCG
           _____a_____a_____AMP-ORF_____a_____a_____>
           _____c_____PUC19 BACKBONE H3 To AATII_____c_____>
```

*FIG. 4*
(CONTINUED)

```
                                            >AseI
                                             |
          3070        3080        3090        3100  |     3110        3120
            *           *           *           *   |       *           *
      CAGAAGTGGT  CCTGCAACTT  TATCCGCCTC  CATCCAGTCT ATTAATTGTT  GCCGGGAAGC
      _____a_____a_____AMP-ORF_____a_____a_____>
      _____c_____PUC19 BACKBONE H3 TO AATII_____c_____>

>Psp1406I
                                     |
                            >FspI   |             >BsrDl   >SfcI
                             |      |               |       |
          3130        3140        3150  |    |3160  |     3170  |    3180
            *           *           *   |      *|     *       *   |      *
      TAGAGTAAGT  AGTTCGCCAG  TTAATAGTTT  GCGCAACGTT  GTTGCCATTG  CTACAGGCAT
      _____a_____a_____AMP-ORF_____a_____a_____>
      _____c_____PUC19 BACKBONE H3 TO AATII_____c_____>

>MslI                                               >BsaWI
  |                                                  |
  |       3190        3200        3210        3220  |    3230        3240
  |  *      *           *           *           *   |      *           *
      CGTGGTGTCA  CGCTCGTCGT  TTGGTATGGC  TTCATTCAGC  TCCGGTTCCC  AACGATCAAG
      _____a_____a_____AMP-ORF_____a_____a_____>
      _____c_____PUC19 BACKBONE H3 TO AATII_____c_____>

>PvuI
                                                                     |
                                                                   >BsiEI
                                                                     |
          3250        3260        3270        3280        3290        3300
            *           *           *           *           *           *
      GCGAGTTACA  TGATCCCCCA  TGTTGTGCAA  AAAAGCGGTT  AGCTCCTTCG  GTCCTCCGAT
      _____a_____a_____AMP-ORF_____a_____a_____>
      _____c_____PUC19 BACKBONE H3 TO AATII_____c_____>

>EaeI                        >MslI
                       |                            |
          3310        3320        3330        3340  |     3350        3360
            *           *        |  *           *   |       *           *
      CGTTGTCAGA  AGTAAGTTGG  CCGCAGTGTT  ATCACTCATG  GTTATGGCAG  CACTGCATAA
      _____a_____a_____AMP-ORF_____a_____a_____>
      _____c_____PUC19 BACKBONE H3 TO AATII_____c_____>

>ScaI
                                                             |
          3370        3380        3390        3400        3410        3420
            *           *           *           *           *           *
      TTCTCTTACT  GTCATGCCAT  CCGTAAGATG  CTTTTCTGTG  ACTIGGTGAGT ACTCAACCAA
      _____a_____a_____AMP-ORF_____a_____a_____>
      _____c_____PUC19 BACKBONE H3 TO AATII_____c_____>

>BsiEI
                           |
          3430        3440        3450        3460        3470        3480
            *           *           *        |  *           *           *
      GTCATTCTGA  GAATAGTGTA  TGCGGCGACC  GAGTTGCTCT  TGCCCGGCGT  CAATACGGGA
      _____a_____a_____AMP-ORF_____a_____a_____>
      _____c_____PUC19 BACKBONE H3 TO AATII_____c_____>
```

FIG. 4
(CONTINUED)

```
                                                  >XmnI
                                                   |
                  >DraI     >BsiHKAI     >Pspl406I
                   |           |            |
     3490      3500        3510       |3520        3530         3540
       *    *     *    *     *  | *     *| *       *  |*       *    *
     TAATACCGCG CCACATAGCA GAACTTTAAA AGTGCTCATC ATTGGAAAAC GTTCTTCGGG
     _____a_____a_____AMP-ORF_____a_____a_____>
              _____c_____PUC19 BACKBONE H3 TO AATII_____c_____>

>Eco57I
                                                                     |
                                                                   >ApaLI
                                                                     |
                              >MspAlI                              >BsssI
                                 |                                 | |
     3550        3560       | 3570        3580        3590         |  3600
       *    *     *    *     *    *     *    *     *    *        |*  |  *
     GCGAAAACTC TCAAGGATCT TACCGCTGTT GAGATCCAGT TCGATGTAAC CCACTCGTGC
     _____a_____a_____AMP-ORF_____a_____a_____>
              _____c_____PUC19 BACKBONE H3 TO AATII_____c_____>

>BsiHKAI
   |
   |    3610        3620        3630        3640        3650         3660
   | *    *     *    *     *    *     *    *     *    *       *    *
   ACCCAACTGA TCTTCAGCAT CTTTTACTTT CACCAGCGTT TCTGGGTGAG CAAAAACAGG
   _____a_____a_____AMP-ORF_____a_____a_____>
            _____c_____PUC19 BACKBONE H3 To AATII_____c_____>

>MslI
                                                  |
         3670        3680        3690        3700        3710         3720
           *    *     *    *     *    *     *    *     *    *       *    *
     AAGGCAAAAT GCCGCAAAAA AGGGAATAAG GGCGACACGG AAATGTTGAA TACTCATACT
     _____a_____a_____AMP-ORF_____a_____a_____>
              _____c_____PUC19 BACKBONE H3 TO AATII_____c_____>

>EarI    >SspI                              >BspHI    >BsrBI
       |        |                                  |         |
       | 3730   | 3740        3750        3760   | 3770    | 3780
       |  *     |*    *     *    *     *    *     *    *    |  *    *
     CTTCCTTTTT CAATATTATT GAAGCATTTA TCAGGGTTAT TGTCTCATGA GCGGATACAT
              _____c_____PUC19 BACKBONE H3 TO AATII_____c_____>

3790        3800        3810        3820        3830         3840
           *    *     *    *     *    *     *    *     *    *       *    *
     ATTTGAATGT ATTTAGAAAA ATAAACAAAT AGGGGTTCCG CGCACATTTC CCCGAAAAGT
              _____c_____PUC19 BACKBONE H3 TO AATII_____c_____>

>HincII
                 |
              >AccI
                 ||
              >AatII
                 |||
              >SalI
                 ||||
         3850  ||||
           *    *  ||||
     GCCACCTGAC GTC
              __c___>
```

FIG. 4
(CONTINUED)

```
                           >HincII
                            |
                           >AccI
                            ||
          >BglII           >SalI
           |               |||
     10    |    20    30   |||   40         50         60
  *    *   |*    *    *    |||*   *    *    *    *    *    *
GACGGATCGG GAGATCTCCC GATCCCCTAT GGTCGACTCT CAGTACAATC TGCTCTGATG >AlwNI
                 |
                 |
      70         80         90        100        110        120
  *    *    *    *    *    *    *    *    *    *    *    *
CCGCATAGTT AAGCCAGTAT CTGCTCCCTG CTTGTGTGTT GGAGGTCGCT GAGTAGTGCG >ApoI                                  >MfeI
    |                                      |
    |130        140        150        160  |    170        180
  * | *    *    *    *    *    *    * | *    *    *    *
CGAGCAAAAT TAAGCTACA ACAAGGCAAG GCTTGACCGA CAATTGCATG AAGAATCTGC >HincII
                                                            |
                                                    >AflIII |
                                                     |      |
                                 >NruI              >MluI   |
                                  |                  |      |
      190        200        |210        220         |230    |
  *    *    *    *    *    |*    *    *    *    *   |*    |*
TTAGGGTTAG GCGTTTTGCG CTGCTTCG CGA TGT ACG GGC CAG ATA TAC GCG TTG
                             Arg Cys Thr Gly Gln Ile Tyr Ala Leu>
                            ___e___e___CMV PROMOTER___e___e___>

>SpeI     >AseI
            |        |
    240    250      |260        270        280
  *    *   |*    *  |  *    *    *    *    *
ACA TTG ATT ATT GAC TAG TTA TTA ATA GTA ATC AAT TAC GGG GTC ATT
Thr Leu Ile Ile Asp *** Leu Leu Ile Val Ile Asn Tyr Gly Val Ile>
___e___e___e___e___e_CMV PROMOTER_e___e___e___e___e___>

290        300        310        320        330
  *    *    *    *    *    *    *    *    *    *
AGT TCA TAG CCC ATA TAT GGA GTT CCG CGT TAC ATA ACT TAC GGT AAA
Ser Ser *** Pro Ile Tyr Gly Val Pro Arg Tyr Ile Thr Tyr Gly Lys>
___e___e___e___e___e___e_CMV PROMOTER_e___e___e___e___e___>

>BglI                                           >AatII
       |                                               |
      340        350        360        370            |
  *    *    *    *    *    *    *    *    *    *
TGG CCC GCC TGG CTG ACC GCC CAA CGA CCC CCG CCC ATT GAC GTC AAT
Trp Pro Ala Trp Leu Thr Ala Gln Arg Pro Pro Pro Ile Asp Val Asn>
___e___e___e___e___e___e_CMV PROMOTER_e___e___e___e___e___>

380        390        400        410        420
  *    *    *    *    *    *    *    *    *    *
AAT GAC GTA TGT TCC CAT AGT AAC GCC AAT AGG GAC TTT CCA TTG ACG
Asn Asp Val Cys Ser His Ser Asn Ala Asn Arg Asp Phe Pro Leu Thr>
___e___e___e___e___e___e_CMV PROMOTER_e___e___e___e___e___>
```

FIG. 6

```
     >AatII                                            >BglI
     |                                                 |
     430           440           450           460    |     470
     |  *      *      *      *      *      *      *      *      *      *
     TCA ATG GGT GGA CTA TTT ACG TAA AAC TGC CCA CTT GGC AGT ACA TCA
     Ser Met Gly Gly Leu Phe Thr Val Asn Cys Pro Leu Gly Ser Thr Ser>
     ___e___e___e___e___e___e_CMV PROMOTER__e___e___e___e___e___e___>

>NdeI                                    >AatII
              |                                        |
     480      |     490           500           510|        520
     *        | *      *      *      *      *      *|    *      *
     AGT GTA TCA TAT GCC AAG TAC GCC CCC TAT TGA CGT CAA TGA CGG TAA
     Ser Val Ser Tyr Ala Lys Tyr Ala Pro Tyr * Arg Gln * Arg ***>
     ___e___e___e___e___e___e_CMV PROMOTER__e___e___e___e___e___e___>

>BglI
              |
     530      |     540           550           560           570
     *      * | *      *      *      *      *      *      *      *
     ATG GCC CGC CTG GCA TTA TGC CCA GTA CAT GAC CTT ATG GGA CTT TCC
     Met Ala Arg Leu Ala Leu Cys Pro Val His Asp Leu Met Gly Leu Ser>
     ___e___e___e___e___e___e_CMV PROMOTER__e___e___e___e___e___e___>

>BsaAI                 >NcoI
                              |                      |
                           >SnaBI                 >StyI  >MsII
                              |                      |     |
              580           590           600           610   |
     *      *      *      *      *      *      *      *      *      *
     TAC TTG GCA GTA CAT CTA CGT ATT AGT CAT CGC TAT TAC CAT GGT GAT
     Tyr Leu Ala Val His Leu Arg Ile Ser His Arg Tyr Tyr His Gly Asp>
     ___e___e___e___e___e___e_CMV PROMOTER__e___e___e___e___e___e___>

620           630           640           650           660
     *      *      *      *      *      *      *      *      *      *
     GCG GTT TTG GCA GTA CAT CAA TGG GCG TGG ATA GCG GTT TGA CTC ACG
     Ala Val Leu Ala Val His Gln Trp Ala Trp Ile Ala Val *** Leu Thr>
     ___e___e___e___e___e___e_CMV PROMOTER__e___e___e___e___e___e___>

>AatII                 >BanI
                                          |                      |
     670           680           690     | 700           710     |
     *      *      *      *      *      *| *      *      *      *
     GGG ATT TCC AAG TCT CCA CCC CAT TGA CGT CAA TGG GAG TTT GTT TTG
     Gly Ile Ser Lys Ser Pro Pro His *** Arg Gln Trp Glu Phe Val Leu>
     ___e___e___e___e___e___e_CMV PROMOTER__e___e___e___e___e___e___>

720           730           740           750           760
     *      *      *      *      *      *      *      *      *
     GCA CCA AAA TCA ACG GGA CTT TCC AAA ATG TCG TAA CAA CTC CGC CCC
     Ala Pro Lys Ser Thr Gly Leu Ser Lys Met Ser *** Gln Leu Arg Pro>
     ___e___e___e___e___e___e_CMV PROMOTER__e___e___e___e___e___e___>

770           780           790           800           810
     *      *      *      *      *      *      *      *      *      *
     ATT GAC GCA AAT GGG CGG TAG GCG TGT ACG GTG GGA GGT CTA TAT AAG
     Ile Asp Ala Asn Gly Arg *** Ala Cys Thr Val Gly Gly Leu Tyr Lys>
     ___e___e___e___e___e___e_CMV PROMOTER__e___e___e___e___e___e___>
```

FIG. 6
(CONTINUED)

```
          >SacI
           |
          BanII
           |
        >BsiHKAI
           |
      >Ecl136II
       |  |
       |  |  820          830         840         850
       *|  | *    *    *    *    *    *    *    *    *
      CAG AGC TCT CTG GCT AAC TAG AGA ACC CAC TGC TTA CTG GCT TAT CGA
      Gln Ser Ser Leu Ala Asn *** Arg Thr His Cys Leu Leu Ala Tyr Arg>
      ___e___e___e___e___e___e_CMV PROMOTER__e___e___e___e___e___e___>

>KpnI
                                                               |
                         >BsaI                      >Acc65I|
                          |                              |  |  |
   >AseI         >SfcI          >HindIII           >BanI  |  |
      |           ||               |                  |   |  |
     >T7_PROMOTER ||               |                  |   |  |
      |  |        ||               |                  |   |  |
  860 |  |   870  ||  880         890          900    |   |  910
    * |  |  *    *|   *   *    *   |*    *    *   *   |  *    *
   AAT T AATACGA CTCACTATAG GGAGACCCAA GCTTCGCGCG GGTACCACTC
   Asn Xxx>
   ___e_>
                                                            ___>

>PflMI
                                  |
                         >PvuII|      >BanII
    >EarI                  |   |        |
     |                     |   |        |
     | 920         930    940  |   950         960         970
    *|   *    *    *    *    |*   |*   |*    *    *    *    *
   TCTTCCGCAT CGCTGTCTGC GAGGGCCAGC TGTTGGGCTC GCGGTTGAGG ACAAACTCTT
   _____f_____f_TRIPARTITE LEADER __f_____f_____>

>EarI         >ScaI
   |             |
   |   980      |  990      1000        1010        1020        1030
   |    *    *    *    *    *    *    *    *    *    *    *    *
   CGCGGTCTTT CCAGTACTCT TGGATCGGAA ACCCGTCGGC CTCCAACGG TACTCCGCCA
   _____f_____f_TRIPARTITE LEADER __f_____f_____>

>BsoBI
                                                             |
                                                           >AvaI
                                                             |
    >EcoO109I                        >BsiEI            >XhoI
      |                                 |                |
     >PpuMI                          >BsaWI          >PaeR7I
      |                                 ||              |
      |1040        1050        1060     ||  1070    | 1080        1090
     *|    *    *    *    *    *    *  ||*   *    *   |*    *    *    *
    CCGAGGGACC TGAGCGAGTC CGCATCGACC GGATCGGAAA ACCTCTCGAG GAACTGAAAA
                                                                  ___>
    _____f___TRIPARTITE LEADER _____f____>

FIG. 6
                             (CONTINUED)
```

```
        >HincII                                      >EcoO109I      >BsaWI
         |                                            |              |
        >HpaI                                        >PpuMI        >BamHI
         |                                            |            | | |
      1100  |    1110       1120       1130        1140       |  1150
   *      * |      *   *        *    *       *    *        * |  |*  |   *
ACCAGAAAGT TAACTGGTAA GTTTAGTCTT TTTGTCTTTT TATTTCAGGT CCCGGATCCG
         b          HYBRID SV40 LATE INTRON          b         >
```

```
              >BseRI                                              >StuI
               |                                                   |
       1160    |1170       1180       1190       1200       |  1210
    *     *   *|    *       *    *        *    *        *   *    *
GTGGTGGTGC AAATCAAAGA ACTGCTCCTC AGTGGATGTT GCCTTTACTT CTAGGCCTGT
         b           HYBRID SV40 LATE INTRON          b         >
```

```
                                                    >BsiEI
                                                     |
                                                    >EagI|
                                                     |  |
                                                    >EaeI|        >XbaI
                                                     |  |          |
                                                    >SacII        >PstI
                                                     |  |         | |
                                                    >NotI | >SfcI | |
                                                     |  | |   |   | |
       1220        1230        1240       1250     | 1260 |   | 1270
     *     *    *     *     *     *    *     *    * |*  |   *|  *
ACGGAAGTGT TACTTCTGCT CTAAAAGCTG CGGAATTGTA CCCGCGGCCG CTGCAGTCTA
             HYBRID SV40 LATE INTRON          b   >
```

```
                            >ApaI
                             |
                    >BspDI  >EcoO109I
                     |       | |
   >ApoI            >EcoRV| >Bsp120I
    |                |   | || |
  >EcoRI  >BsiWI    >ClaI |>BanII    >SfcI         >MslI
    |       |        |    | |         |              |
    |    1280  |   1290  | |1300    | 1310        1320
    |*    *  |    *  |  *  *|  |*     *    *     *  |  *
GACGAATTCG CGTACGATAT CGATGGGCCC TATT CTA TAG TGT CAC CTA AAT
                                     Leu *** Cys His Leu Asn>
                                       c_SP6 PROMOTER__c___>
```

```
        >SacI
         |
        >BanII
         |
        >BsiHKAI
         |
 >Ecl136II | >BclI
    |    |   |
 >BGH_POLY_A |   |
    |    |   |
    |  1330  |  | 1340       1350       1360       1370       1380
   |*    |*  |    *    *       *    *       *    *       *    *
GCTAGAGC TCGCTGATCA GCCTCGACTG TGCCTTCTAG TTGCCAGCCA TCTGTTGTTT
```

```
                                 >BanI
                                  |
        1390       1400       1410  |   1420       1430       1440
      *     *    *     *    *     *|    *     *    *     *    *     *
GCCCCTCCCC CGTGCCTTCC TTGACCCTGG AAGGTGCCAC TCCCACTGTC CTTTCCTAAT
```

FIG. 6
(CONTINUED)

```
           1450       1460       1470       1480       1490       1500
         *    *     *    *     *    *     *    *     *    *     *    *
       AAAATGAGGA AATTGCATCG CATTGTCTGA GTAGGTGTCA TTCTATTCTG GGGGGTGGGG
                                                  >BbsI
                                                   |
           1510       1520       1530       1540       1550       1560
         *    *     *    *     *    *     *  | *     *    *     *    *
       TGGGGCAGGA CAGCAAGGGG GAGGATTGGG AAGACAATAG CCGAAATGAC CGACCAAGCG
                        >BspMI
                         |
                        >BssSI
                         |
           1570       1580       1590       1600       1610       1620
         *    *     * |  *     *    *     *    *     *    *     *    *
       ACGCCCAACC TGCCATCACG AGATTTCGAT TCCACCGCCG CCTTCTATGA AAGGTTGGGC
                            >NaeI
                             |
                            >NgoMI
                            | |
                            >BpmI
                            | |
                            >BsrFI
                            | |
           1630       1640  | | 1650       1660       1670       1680
         *    *     *    *  | | *    *     *    *     *    *     *    *
       TTCGGAATCG TTTTCCGGGA CGCCGGCTGG ATGATCCTCC AGCGCCGGGA TCTCATGCTG

>BpmI
                         |
                        >SV40_early_poly_A
                         |
           1690       1700       1710       1720       1730       1740
         *    *     *    *     * |*     *    *     *    *     *    *
       GAGTTCTTCG CCCACCCCAA CTTGTTTATT GCAGCTTATA ATGGTTACAA ATAAAGCAAT
            >ApoI                              >BsmI
             |                                  |
           1750       1760       1770       1780       1790       1800
         *  |  *     *    *     *    *     *  | *     *    *     *    *
       AGCATCACAA ATTTCACAAA TAAAGCATTT TTTTCACTGC ATTCTAGTTG TGGTTTGTCC
                                                         >HincII
                                                          |
                                       >Bst1107I  >AccI
                                        |         | |
                                       >AccI|    >SalI
                                        | |      |||
           1810       1820       1830 |   |1840  |||  1850       1860
         *    *     *    *     *    * |   * ||| *    *    *     *    *
       AAACTCATCA ATGTATCTTA TCATGTCTGT ATACCGTCGA CCTCTAGCTA GAGCTTGGCG
                                                                       >
                                                                _____
                                      >BsrBI
                                       |
           1870       1880       1890       1900  | 1910       1920
         *    *     *    *     *    *     *    * |  *    *     *    *
       TAATCATGGT CATAGCTGTT TCCTGTGTGA AATTGTTATC CGCTCACAAT TCCACACAAC
       _____d_____d___PUC19 BACKBONE____d_____d_____>
```

*FIG. 6*
(CONTINUED)

```
                                          >BanI
                                            |
         1930       1940       1950       | 1960       1970       1980
           *          *          *         |*           *          *
      ATACGAGCCG GAAGCATAAA GTGTAAAGCC TGGGGTGCCT AATGAGTGAG CTAACTCACA
      _____d_____d___PUC19 BACKBONE____d_____d_____>

>AseI
                                              >PvuII    |
     >AseI                                       |      |
       |                                         |      |
       |   1990       2000       2010       2020 |    2030     | 2040
       |    *          *          *          *          *      |*    *
      TTAATTGCGT TGCGCTCACT GCCCGCTTTC CAGTCGGGAA ACCTGTCGTG CCAGCTGCAT
      _____d_____d___PUC19 BACKBONE____d_____d_____>

>EarI
                                                            |
              >EaeI                             >HaeII   >SapI
                |                                  |       |
             2050       2060       2070       2080       2090    | 2100
               *  |*      *          *          *          *  | *  |*   *
      TAATGAATCG GCCAACGCGC GGGGAGAGGC GGTTTGCGTA TTGGGCGCTC TTCCGCTTCC
      _____d_____d___PUC19 BACKBONE____d_____d_____>

>BsiEI                 >BsrBI
                         |                      |
         2110       2120 |    2130       2140   |   2150       2160
           *          *    *|   *          *          *  |  *    *
      TCGCTCACTG ACTCGCTGCG CTCGGTCGTT CGGCTGCGGC GAGCGGTATC AGCTCACTCA
      _____d_____d___PUC19 BACKBONE____d_____d_____>

>AflIII
                                                         |
         2170       2180       2190       2200       2210       2220
           *          *          *          *          *          *
      AAGGCGGTAA TACGGTTATC CACAGAATCA GGGGATAACG CAGGAAAGAA CATGTGAGCA
      _____d_____d___PUC19 BACKBONE____d_____d_____>

2230       2240       2250       2260       2270       2280
           *          *          *          *          *          *
      AAAGGCCAGC AAAAGGCCAG GAACCGTAAA AAGGCCGCGT TGCTGGCGTT TTTCCATAGG
      _____d_____d___PUC19 BACKBONE____d_____d_____>

>DrdI
                                                |
         2290       2300       2310       2320       2330       2340
           *          *          *          *  |  *      *          *
      CTCCGCCCCC CTGACGAGCA TCACAAAAAT CGACGCTCAA GTCAGAGGTG GCGAAACCCG
      _____d_____d___PUC19 BACKBONE____d_____d_____>

>BssSI
                                                         |
         2350       2360       2370       2380       |  2390       2400
           *          *          *          *          |*  *          *
      ACAGGACTAT AAAGATACCA GGCGTTTCCC CCTGGAAGCT CCCTCGTGCG CTCTCCTGTT
      _____d_____d___PUC19 BACKBONE____d_____d_____>
```

FIG. 6
(CONTINUED)

```
                     >BsaWI                                                                      >HaeII
                     |                                                                           |
       2410         |2420         2430         2440         2450         2460
    *     *       * |   *       *    *       *    *       *    *       * | *
CCGACCCTGC CGCTTACCGG ATACCTGTCC GCCTTTCTCC CTTCGGGAAG CGTGGCGCTT
_____d_____d___PUC19 BACKBONE___d_____d_____>

>SfcI
              |
       2470   |     2480         2490         2500         2510         2520
    *     *  | *       *       *    *       *    *       *    *       *    *
TCTCAATGCT CACGCTGTAG GTATCTCAGT TCGGTGTAGG TCGTTCGCTC CAAGCTGGGC
_____d_____d___PUC19 BACKBONE___d_____d_____>

>BsiHKAI
        |
>ApaLI|
   |  |
   | 2530         2540         >BsiEI        >BsaWI
   |               |           |             |
   |* | *       *    *       * |  *       * |  *       *    *       *
   | 2530         2540         2550         2560         2570         2580
TGTGTGCACG AACCCCCCGT TCAGCCCGAC CGCTGCGCCT TATCCGGTAA CTATCGTCTT
_____d_____d___PUC19 BACKBONE___d_____d_____>

>AlwNI
                                                    |
       2590         2600         2610         2620         |2630         2640
    *     *       *    *       *    *       *    *       * |  *       *    *
GAGTCCAACC CGGTAAGACA CGACTTATCG CCACTGGCAG CAGCCACTGG TAACAGGATT
_____d_____d___PUC19 BACKBONE___d_____d_____>

>SfcI
                          |
       2650         2660  |     2670         2680         2690         2700
    *     *       *    *  * |    *       *    *       *    *       *    *
AGCAGAGCGA GGTATGTAGG CGGTGCTACA GAGTTCTTGA AGTGGTGGCC TAACTACGGC
_____d_____d___PUC19 BACKBONE___d_____d_____>

>Eco57I
                                                                       |
       2710         2720         2730         2740         2750         2760
    *     *       *    *       *    *       *    *       *    *       * | *
TACACTAGAA GGACAGTATT TGGTATCTGC GCTCTGCTGA AGCCAGTTAC CTTCGGAAAA
_____d_____d___PUC19 BACKBONE___d_____d_____>

2770         2780         2790         2800         2810         2820
    *     *       *    *       *    *       *    *       *    *       *    *
AGAGTTGGTA GCTCTTGATC CGGCAAACAA ACCACCGCTG GTAGCGGTGG TTTTTTTGTT
_____d_____d___PUC19 BACKBONE___d_____d_____>

2830         2840         2850         2860         2870         2880
    *     *       *    *       *    *       *    *       *    *       *    *
TGCAAGCAGC AGATTACGCG CAGAAAAAAA GGATCTCAAG AAGATCCTTT GATCTTTTCT
_____d_____d___PUC19 BACKBONE___d_____d_____>

>BspHI
                                                                |
       2890         2900         2910         2920         2930         2940
    *     *       *    *       *    *       *    *       *    *       *    *
ACGGGGTCTG ACGCTCAGTG GAACGAAAAC TCACGTTAAG GGATTTTGGT CATGAGATTA
_____d_____d___PUC19 BACKBONE___d_____d_____>
```

FIG. 6
(CONTINUED)

```
                      >DraI                              >DraI
                       |                                   |
     2950      2960    |  2970      2980      2990      |  3000
  *     *   *     *   *|    *    *     *    *    |*    *     *
TCAAAAAGGA TCTTCACCTA GATCCTTTTA AATTAAAAAT GAAGTTTTAA ATCAATCTAA
_____d_____d____PUC19 BACKBONE____d_____d_____>

>BanI
                                                         |
     3010      3020      3030      3040      3050      | 3060
  *     *   *     *   *     *   *     *   *     *   *  |  *   *
AGTATATATG AGTAAACTTG GTCTGACAGT TACCAATGCT TAATCAGTGA GGCACCTATC
                                        a          AMP-ORF   a           >
_____d_____d____PUC19 BACKBONE____d_____d_____>

>AhdI
                                          |
     3070      3080      3090      3100   | 3110      3120
  *     *   *     *   *     *   *     *   |*    *    *    *
TCAGCGATCT GTCTATTTCG TTCATCCATA GTTGCCTGAC TCCCCGTCGT GTAGATAACT
____a_____a_____AMP-ORF_____a_____a_____>
_____d_____d____PUC19 BACKBONE____d_____d_____>

>BsaI
                                          |
                               >BsrDI    >BpmI
                                |          |
     3130      3140      3150   | 3160    | 3170    | 3180
  *     *   *     *   *     *   |*    *   |*    *   |*    *
ACGATACGGG AGGGCTTACC ATCTGGCCCC AGTGCTGCAA TGATACCGCG AGACCCACGC
____a_____a_____AMP-ORF_____a_____a_____>
_____d_____d____PUC19 BACKBONE____d_____d_____>

>BsrFI                                   >BglI
 |                                        |
 |   3190      3200      3210      3220   | 3230      3240
 |*    *   *     *   *     *   *     *   |*    *    *    *
TCACCGGCTC CAGATTTATC AGCAATAAAC CAGCCAGCCG GAAGGGCCGA GCGCAGAAGT
____a_____a_____AMP-ORF_____a_____a_____>
_____d_____d____PUC19 BACKBONE____d_____d_____>

>AseI
                                 |
     3250      3260      3270    | 3280      3290      3300
  *     *   *     *   *     *   *|    *   *     *   *     *
GGTCCTGCAA CTTTATCCGC CTCCATCCAG TCTATTAATT GTTGCCGGGA AGCTAGAGTA
____a_____a_____AMP-ORF_____a_____a_____>
_____d_____d____PUC19 BACKBONE____d_____d_____>

>PspI406I
                     |
           >FspI    | >BsrDI   >SfcI        >MslI
            |   |    |          |            |
     3310   |  3320 | 3330      3340      | 3350      | 3360
  *     *   *     *   *     *|  *    *|  *|    *   *     *
AGTAGTTCGC CAGTTAATAG TTTGCGCAAC GTTGTTGCCA TTGCTACAGG CATCGTGGTG
____a_____a_____AMP-ORF_____a_____a_____>
_____d_____d____PUC19 BACKBONE____d_____d_____>
```

FIG. 6
(CONTINUED)

```
                                       >BsaWI
                                         |
    3370       3380       3390       |  3400       3410       3420
      *          *          *        |*   *          *          *
  TCACGCTCGT CGTTTGGTAT GGCTTCATTC AGCTCCGGTT CCCAACGATC AAGGCGAGTT
_____a_____a_____AMP-ORF_____a_____a_____>
_____d_____d___PUC19 BACKBONE_____d_____d_____>

>BsiEI
                                                            |
                                                         >PvuI
                                                            |
    3430       3440       3450       3460       3470     |  3480
      *          *          *          *          *      |*   *
  ACATGATCCC CCATGTTGTG CAAAAAAGCG GTTAGCTCCT TCGGTCCTCC GATCGTTGTC
_____a_____a_____AMP-ORF_____a_____a_____>
_____d_____d___PUC19 BACKBONE_____d_____d_____>

>EaeI                    >MslI
             |                        |
    3490   | 3500       3510       | 3520       3530       3540
      *    |*   *          *       |*   *          *          *
  AGAAGTAAGT TGGCCGCAGT GTTATCACTC ATGGTTATGG CAGCACTGCA TAATTCTCTT
_____a_____a_____AMP-ORF_____a_____a_____>
_____d_____d___PUC19 BACKBONE_____d_____d_____>

>ScaI
                                                   |
    3500       3560       3570       3580       | 3590       3600
      *          *          *          *        |*   *          *
  ACTGTCATGC CATCCGTAAG ATGCTTTTCT GTGACTGGTG AGTACTCAAC CAAGTCATTC
_____a_____a_____AMP-ORF_____a_____a_____>
_____d_____d___PUC19 BACKBONE_____d_____d_____>

>BsiEI
                 |
    3610       3620     | 3630       3640       3650       3660
      *          *      |*   *          *          *          *
  TGAGAATAGT GTATGCGGCG ACCGAGTTGC TCTTGCCCGG CGTCAATACG GGATAATACC
_____a_____a_____AMP-ORF_____a_____a_____>
_____d_____d___PUC19 BACKBONE_____d_____d_____>

>Psp1406I
                                                |
              >DraI     >BsiHKAI             >XmnI
                |         |                     |
    3670       3680     | 3690       3700    |  3710       3720
      *          *      |*   *          *    |*   *          *
  GCGCCACATA GCAGAACTTT AAAAGTGCTC ATCATTGGAA AACGTTCTTC GGGGCGAAAA
_____a_____a_____AMP-ORF_____a_____a_____>
_____d_____d___PUC19 BACKBONE_____d_____d_____>

>ApaLI
                                                            |
                                                         >Eco57I
                                                            |
                                                  >BsssSI | >BsiHKAI
                                                    |    |  |
    3730       3740       3750       3760       3770   | 3780
      *          *          *          *         *   |* |*   *
  CTCTCAAGGA TCTTACCGCT GTTGAGATCC AGTTCGATGT AACCCACTCG TGCACCCAAC
_____a_____a_____AMP-ORF_____a_____a_____>
_____d_____d___PUC19 BACKBONE_____d_____d_____>
```

*FIG. 6*
(CONTINUED)

```
            3790         3800         3810         3820         3830         3840
         *    *       *    *       *    *       *    *       *    *       *    *
        TGATCTTCAG  CATCTTTTAC  TTTCACCAGC  GTTTCTGGGT  GAGCAAAAAC  AGGAAGGCAA
              a           a         AMP-ORF       a           a                >
        _____d_____d____PUC19 BACKBONE____d_____d_____>

>MslI                              >EarI
                                              |                                  |
            3850         3860         3870    |    3880         3890         3900
         *    *       *    *       *    *     | *    *       *    *       *  | *
        AATGCCGCAA  AAAAGGGAAT  AAGGGCGACA  CGGAAATGTT  GAATACTCAT  ACTCTTCCTT
              a           a         AMP-ORF       a                            >
        _____d_____d____PUC19 BACKBONE____d_____d_____>

>SspI                                  >BspHI      >BsrBI
            |                                      |          |
            3910         3920         3930         3940    |  3950         3960
         *  | *       *    *       *    *       *    *    |*    *       *    *
        TTTCAATATT  ATTGAAGCAT  TTATCAGGGT  TATTGTCTCA  TGAGCGGATA  CATATTTGAA
                d           d    PUC19 BACKBONE     d           d            >

3970         3980         3990         4000         4010         4020
         *    *       *    *       *    *       *    *       *    *       *    *
        TGTATTTAGA  AAAATAAACA  AATAGGGGTT  CCGCGCACAT  TTCCCCGAAA  AGTGCCACCT
                d           d    PUC19 BACKBONE     d           d            >

>HincII
           |
         >AatII
           ||
         >AccI
           ||
         >SalI
           |||
           |*|
        GACGTC
        _____>
```

*FIG. 6*
(CONTINUED)

```
                              >HincII
                              |
                              >AccI
                              ||
         >BglII               >SalI
         |                    |||
       10  |     20        30 |||    40          50          60
  *    *   | *    *    *    * |||*   *    *    *    *    *    *
GACGGATCGG GAGATCTCCC GATCCCCTAT GGTCGACTCT CAGTACAATC TGCTCTGATG >AlwNI
                |
      70        80        90       100       110       120
  *    *    *    *    *    *    *    *    *    *    *    *
CCGCATAGTT AAGCCAGTAT CTGCTCCCTG CTTGTGTGTT GGAGGTCGCT GAGTAGTGCG >ApoI                                 >MfeI
   |                                     |
   |130       140       150       160 |   170       180
  *|   *    *    *    *    *    *    *|   *    *    *    *
CGAGCAAAAT TTAAGCTACA ACAAGGCAAG GCTTGACCGA CAATTGCATG AAGAATCTGC >HincII
                                                              |
                                                     >AflIII  |
                                                     |        |
                       >NruI                         >MluI    |
                       |                             |        |
     190       200     |210       220          |230           |
  *    *    *    *    *|   *    *    *    *    |*   *         |*
TTAGGGTTAG GCGTTTTGCG CTGCTTCG CGA TGT ACG GGC CAG ATA TAC GCG TTG
                                 Arg Cys Thr Gly Gln Ile Tyr Ala Leu>
                                 __f___f___CMV PROMOTER___f___f___>

>SpeI      >AseI
           |          |
   240     |  250     | 260       270          280
  *    *   |*    *    | *    *    *    *    *    *
ACA TTG ATT ATT GAC TAG TTA TTA ATA GTA ATC AAT TAC GGG GTC ATT
Thr Leu Ile Ile Asp *** Leu Leu Ile Val Ile Asn Tyr Gly Val Ile>
  f   f   f   f   f   f_CMV PROMOTER__f___f___f___f___f___f___>

290       300       310       320          330
  *    *    *    *    *    *    *    *    *    *
AGT TCA TAG CCC ATA TAT GGA GTT CCG CGT TAC ATA ACT TAC GGT AAA
Ser Ser *** Pro Ile Tyr Gly Val Pro Arg Tyr Ile Thr Tyr Gly Lys>
  f   f   f   f   f   f_CMV PROMOTER__f   f___f___f___f___f___>

>BglI                                         >AatII
         |                                             |
         340       350       360          370          |
  *    *    *    *    *    *    *    *    *
TGG CCC GCC TGG CTG ACC GCC CAA CGA CCC CCG CCC ATT GAC GTC AAT
Trp Pro Ala Trp Leu Thr Ala Gln Arg Pro Pro Pro Ile Asp Val Asn>
  f   f   f   f   f   f_CMV PROMOTER__f___f___f___f___f___f___>

380         390          400           410          420
  *    *    *    *    *    *    *    *    *    *    *
AAT GAC GTA TGT TCC CAT AGT AAC GCC AAT AGG GAC TTT CCA TTG ACG
Asn Asp Val Cys Ser His Ser Asn Ala Asn Arg Asp Phe Pro Leu Thr>
  f   f   f   f   f   f_CMV PROMOTER__f___f___f___f___f___f___>
```

*FIG. 8*

```
        >AatII                                              >BglI
         |                                                   |
         430            440           450           460      |    470
         | *      *      *      *      *      *      * |  *      *     *
         TCA ATG GGT GGA CTA TTT ACG GTA AAC TGC CCA CTT GGC AGT ACA TCA
         Ser Met Gly Gly Leu Phe Thr Val Asn Cys Pro Leu Gly Ser Thr Ser>
         ___f___f___f___f___f___f_CMV PROMOTER__f___f___f___f___f___f___>

>NdeI                                      >AatII
                  |                                          |
            480   |     490           500           510|          520
              *   | *      *      *      *      *      * |   *      *
         AGT GTA TCA TAT GCC AAG TAC GCC CCC TAT TGA CGT CAA TGA CGG TAA
         Ser Val Ser Tyr Ala Lys Tyr Ala Pro Tyr * Arg Gln * Arg ***>
         ___f___f___f___f___f___f_CMV PROMOTER__f___f___f___f___f___f___>

>BglI
                   |
            530    |     540           550           560          570
            *      | *      *      *      *      *      *      *      *
         ATG GCC CGC CTG GCA TTA TGC CCA GTA CAT GAC CTT ATG GGA CTT TCC
         Met Ala Arg Leu Ala Leu Cys Pro Val His Asp Leu Met Gly Leu Ser>
         ___f___f___f___f___f___f_CMV PROMOTER__f___f___f___f___f___f___>

>BsaAI                        >StyI
                               |                             |
                           >SnaBI                         >NcoI    >MslI
                               |                             |       |
                  580         590           600           610        |
              *      *      *      *      *      *      *      *      *
         TAC TTG GCA GTA CAT CTA CGT ATT AGT CAT CGC TAT TAC CAT GGT GAT
         Tyr Leu Ala Val His Leu Arg Ile Ser His Arg Tyr Tyr His Gly Asp>
         ___f___f___f___f___f___f_CMV PROMOTER__f___f___f___f___f___f___>

620           630           640           650           660
           *      *      *      *      *      *      *      *      *      *
         GCG GTT TTG GCA GTA CAT CAA TGG GCG TGG ATA GCG GTT TGA CTC ACG
         Ala Val Leu Ala Val His Gln Trp Ala Trp Ile Ala Val *** Leu Thr>
         ___f___f___f___f___f___f_CMV PROMOTER__f___f___f___f___f___f___>

>AatII               >BanI
                                                      |                    |
         670           680           690        | 700           710        |
           *      *      *      *      *      * |   *      *      *        |
         GGG ATT TCC AAG TCT CCA CCC CAT TGA CGT CAA TGG GAG TTT GTT TTG
         Gly Ile Ser Lys Ser Pro Pro His *** Arg Gln Trp Glu Phe Val Leu>
         ___f___f___f___f___f___f_CMV PROMOTER__f___f___f___f___f___f___>

720           730           740           750           760
              *      *      *      *      *      *      *      *      *
         GCA CCA AAA TCA ACG GGA CTT TCC AAA ATG TCG TAA CAA CTC CGC CCC
         Ala Pro Lys Ser Thr Gly Leu Ser Lys Met Ser *** Gln Leu Arg Pro>
         ___f___f___f___f___f___f_CMV PROMOTER__f___f___f___f___f___f___>

770           780           790           800           810
              *      *      *      *      *      *      *      *      *      *
         ATT GAC GCA AAT GGG CGG TAG GCG TGT ACG GTG GGA GGT CTA TAT AAG
         Ile Asp Ala Asn Gly Arg *** Ala Cys Thr Val Gly Gly Leu Tyr Lys>
         ___f___f___f___f___f___f_CMV PROMOTER__f___f___f___f___f___f___>
```

FIG. 8
(CONTINUED)

```
                    >BsiHKAI
                       |
                     SacI
                       |
                    BanII
                       |
     >Ecl136II
         |   |          820           830          840          850
       *|   |*     *         *    *         *    *         *    *         *
        CAG AGC TCT CTG GCT AAC TAG AGA ACC CAC TGC TTA CTG GCT TAT CGA
        Gln Ser Ser Leu Ala Asn *** Arg Thr His Cys Leu Leu Ala Tyr Arg>
         ___f___f___f___f___f___f_CMV PROMOTER__f___f___f___f___f___f___>

>KpnI
                                                                |
                              >BsaI                          >BanI  |
                                 |                              |   |
     >AseI              >SfcI         >HindIII         >Acc65I|
        |                 ||              |                |  |
        | >T7_PROMOTER    ||              |                |  |
        |  |  |           ||              |                |  |
     860|  |  | 870       || 880         890             900 |  |  910
       *|  |  |*     *    *|     *    *         *    *    |*     *    *
        AAT T AATACGA CTCACTATAG GGAGACCCAA GCTTCGCGCG GGTACCACTC
        Asn Xxx>
         ___f_>
                                                                           ___>

>PflMI
                                              |
              >EarI                >PvuII|    >BanII
                 |                    |  |       |
                 | 920          930   940 |    950         960         970
               *|     *    *         *    *|  *    |*     *    *         *    *
                TCTTCCGCAT CGCTGTCTGC GAGGGCCAGC TGTTGGGCTC GCGGTTGAGG ACAAACTCTT
                _____g_____TRIPARTITE LEADER SEQUENCE_____g_____>
     >EarI           >ScaI
        |               |
        |  980         | 990        1000        1010        1020        1030
        |   *     *    |    *    *         *    *         *    *         *    *
        CGCGGTCTTT CCAGTACTCT TGGATCGGAA ACCCGTCGGC CTCCGAACGG TACTCCGCCA
        _____g_____TRIPARTITE LEADER SEQUENCE_____g_____>

>XhoI
                                                                |
                                                             >AvaI
                                                                |
     >EcoO109I                       >BsiEI              >BsoBI
         |                              |                   |
      >PpuMI                         >BsaWI              >PaeR7I
         |                             ||                   |
         |1040         1050           1060        1070     | 1080        1090
        *|    *     *         *    *       ||*     *    *         *    *         *
        CCGAGGGACC TGAGCGAGTC CGCATCGACC GGATCGGAAA ACCTCTCGAG GAACTGAAAA
```

FIG. 8
(CONTINUED)

```
          _____TRIPARTITE LEADER SEQUENCE_____g___>    _____>
              >HpaI                                    >PpuMI
               |                                        |
              >HincII                                  >EcoO109I
               |                                        |
     1100  |      1110        1120        1130        1140        1150
       *    *  |   *    *      *    *      *    *      *  | *      *    *
     ACCAGAAAGT TAACTGGTAA GTTTAGTCTT TTTGTCTTTT TATTTCAGGT CCCGGATCTG
     _____b_____ HYBRID SV40 LATE lNTRON__b_____b_____>

>Ppu10I
                                                                 |
                 >21_bp_tandem_repeat_III_[110],[102],[112]       |
                                           |                     |
         1160        1170        1180     |1190        1200        1210
          *    *      *    *      *    *   *|   *      *    *      *   |*
     AGTTAGGGCG GGACATGGGC GGAGTTAGGG GCGGGACTAT GGTTGCTGAC TAATTGAGAT
                 <_____h_____h_EARLY MRNA_____h_____

>SphI
          |
     >NsiI
     | |
     | |                              <72_bp_tandem_repeat_enhancer_sequence_
     | |                                                                   |
     | | 1220        1230        1240        1250        1260  |    1270
     | *    *         *    *      *    *      *    *      *    * |  *    *
     GCATGCTTTG CATACTTCTG CCTGCTGGGG AGCCTGGGGA CTTTCCACAC CTGGTTGCTG
     <_____h_____h_____EARLY MRNA_____h_____h_____

>NsiI
                   |
          >Ppu10I  |>SphI
           |       | |
         1280  |   | 1290        1300        1310        1320        1330
          *    *  | * |  *        *    *      *    *      *    *      *    *
     ACTAATTGAG ATGCATGCTT TGCATACTTC TGCCTGCTGG GGAGCCTGGG GACTTTCCAC
     <_____h_____h_____EARLY MRNA_____h_____h_____

>PvuII       >BsaWI                >BseRI
                                      |            |                     |
     <72_bp_tandem_repeat_enhancer_sequence_B_
                                         <T_antigen_binding_site_II_     |
                                         |         |    |                |
      |        1340        1350      |  1360     |1370        1380        1390
      | *        *    *      *    *   |   *    *   *|   *      *    *      *   |*
     ACCCTAACTG ACACACATTC CACAGCTGGT TCTTTCAGAT CCGGTGGTGG TGCAAATCAA
                                                           ___ HYBRID SV40 ____>
     <_____h__EARLY MRNA_____h__
                       ___MINOR LATE 19S____>

>StuI
                                           |
         1400        1410        1420        1430        1440        1450
          *    *      *    *      *    *      *  | *      *    *      *    *
     AGAACTGCTC CTCAGTGGAT GTTGCCTTTA CTTCTAGGCC TGTACGGAAG TGTTACTTCT
         _____c_____ HYBRID SV40 LATE INTRON _____c_____>
```

FIG. 8
(CONTINUED)

```
                                    >BsiEI
                                      |
                      >NotI           |
                        |  |          |
                      >EaeI |     >XbaI
                        |  |       |
                      >SacII|  >PstI       >EcoRI
                        |  | |  |            |
                      >EagI |>SfcI |    >ApoI      >BsiWI
                        |  | |  | |     |           |
       1460         1470   1480  |  1490      1500     |  1510
         *     *      *     *  |*| |*  |*       *   |   *  |*   *
       GCTCTAAAAG CTGCGGAATT GTACCCGCGG CCGCTGCAGT CTAGACGAAT TCGCGTACGA
       ___ HYBRID SV40 LATE INT____>
```

```
                  >ApaI                                      >SacI
                    |                                          |
      >BspDI    >BanII                                     >BsiHKAI
         |        |                                           |
      >ClaI   >Eco0109I                                    >BanII
         |        |                                           |
   >EcoRV|    >Bsp120I       >SfcI          >MslI    >Ecl136II|  >BclI
     |  |  |   |  |            |              |         |   | |   |
     |  |  |   |  |            |              |  >BGH_POLY_A| |   |
     |  |  |   |  |            |              |         |   | |   |
     |  |  |  1520 |         1530           1540|     1550   | | 1560
     |  |  |*  ||*  |    *     |*     *       *|    *   |  * | |*  | *
     TATCGATGGG CCCTATT CTA TAG TGT CAC CTA AAT GCTAG AGCTCGCTGA
                        Leu *** Cys His Leu Asn>
                        ___d_SP6 PROMOTER__d___>

1570       1580       1590       1600       1610       1620
         *    *      *    *      *    *      *    *     *     *     *
       TCAGCCTCGA CTGTGCCTTC TAGTTGCCAG CCATCTGTTG TTTGCCCCTC CCCCGTGCCT
```

```
                  >BanI
                    |
       1630        |1640       1650       1660       1670       1680
         *    *   *|    *      *    *      *    *      *    *      *
       TCCTTGACCC TGGAAGGTGC CACTCCCACT GTCCTTTCCT AATAAAATGA GGAAATTGCA 1690       1700       1710       1720       1730       1740
         *    *      *    *      *    *      *    *      *    *      *
       TCGCATTGTC TGAGTAGGTG TCATTCTATT CTGGGGGGTG GGGTGGGGCA GGACAGCAAG
```

```
                                                                >BspMI
                                                                  |
                       >BbsI                                   >BssSI
                         |                                        |
       1750       1760       1770       1780       1790       1800
         *    *      *    *      *    *      *    *      *    *      *
       GGGGAGGATT GGGAAGACAA TAGCCGAAAT GACCGACCAA GCGACGCCCA ACCTGCCATC 1810       1820       1830       1840       1850       1860
         *    *      *    *      *    *      *    *      *    *      *
       ACGAGATTTC GATTCCACCG CCGCCTTCTA TGAAAGGTTG GGCTTCGGAA TCGTTTTCCG
```

FIG. 8
(CONTINUED)

```
      >NaeI
       |
   >BpmI
    | |
   >BsrFI
    | |
    NgoMI
    | |
    |  1870       1880       1890       1900       1910       1920
   *|   *     *     *     *     *     *     *     *     *     *     *
   GGACGCCGGC TGGATGATCC TCCAGCGCGG GGATCTCATG CTGGAGTTCT TCGCCCACCC

>BpmI                                                       >ApoI
 |                                                           |
>SV40_early_poly_A                                           |
 |                                                           |
 |    1930       1940       1950       1960       1970     | 1980
 |*    *     *     *     *     *     *     *     *     *  |  *     *
  CAACTTGTTT ATTGCAGCTT ATAATGGTTA CAAATAAAGC AATAGCATCA CAAATTTCAC >BsmI
                        |
      1990       2000  | 2010       2020       2030       2040
   *     *     *     *|   *     *     *     *     *     *     *
   AAATAAAGCA TTTTTTTCAC TGCATTCTAG TTGTGGTTTG TCCAAACTCA TCAATGTATC >HincII
                        |
       >Bst1107I    >AccI
          |         | |
          >AccI     >SalI
          ||        || |
      2050 ||   2060 |   2070       2080       2090       2100
   *     * ||*   |*  |   *     *     *     *     *     *     *
   TTATCATGTC TGTATACCGT CGACCTCTAG CTAGAGCTTG GCGTAATCAT GGTCATAGCT
                                              PUC19 BACKBONE        >

>BsrBI
                           |
      2110       2120    | 2130       2140       2150       2160
   *     *     *     *   |  *     *     *     *     *     *     *
   GTTTCCTGTG TGAAATTGTT ATCCGCTCAC AATTCCACAC AACATACGAG CCGGAAGCAT
   _____e_____e___PUC19 BACKBONE____e_____e_____>

>BanI                            >AseI
                 |                                |
      2170       2180       2190       2200     | 2210       2220
   *     *     *  |  *     *     *     *     * |*   *     *     *
   AAAGTGTAAA GCCTGGGGTG CCTAATGAGT GAGCTAACTC ACATTAATTG CGTTGCGCTC
   _____e_____e___PUC19 BACKBONE____e_____e_____>

>PvuII   >AseI      >EaeI
                                     |       |          |
      2230       2240       2250    2260   | 2270     | 2280
   *     *     *     *     *     * |*   * |*   *     *|  *
   ACTGCCCGCT TTCCAGTCGG GAAACCTGTC GTGCCAGCTG CATTAATGAA TCGGCCAACG
   _____e_____e___PUC19 BACKBONE____e_____e_____>
```

*FIG. 8*
(CONTINUED)

```
                                          >SapI
                                            |
                       >HaeII      >EarI
                         |           |
     2290       2300       2310   |  2320       2330       2340
       *          *          *    | *  *          *          *
CGCGGGGAGA GGCGGTTTGC GTATTGGGCG CTCTTCCGCT TCCTCGCTCA CTGACTCGCT
_____e_____e___PUC19 BACKBONE____e_____e_____>

>BsiEI                  >BsrBI
     |                       |
     2350       2360       |2370       2380       2390       2400
       * |*       *          * |*         *          *          *
GCGCTCGGTC GTTCGGCTGC GGCGAGCGGT ATCAGCTCAC TCAAAGGCGG TAATACGGTT
_____e_____e___PUC19 BACKBONE____e_____e_____>

>AflIII
                                  |
     2410       2420       2430 | 2440       2450       2460
       *          *          * | *  *          *          *
ATCCACAGAA TCAGGGGATA ACGCAGGAAA GAACATGTGA GCAAAAGGCC AGCAAAAGGC
_____e_____e___PUC19 BACKBONE____e_____e_____>

2470       2480       2490       2500       2510       2520
       *          *          *          *          *          *
CAGGAACCGT AAAAAGGCCG CGTTGCTGGC GTTTTTCCAT AGGCTCCGCC CCCCTGACGA
_____e_____e___PUC19 BACKBONE____e_____e_____>

>DrdI
               |
     2530       2540  |    2550       2560       2570       2580
       *          *   |      *          *          *          *
GCATCACAAA AATCGACGCT CAAGTCAGAG GTGGCGAAAC CCGACAGGAC TATAAAGATA
_____e_____e___PUC19 BACKBONE____e_____e_____>

>BssSI                      >BsaWI
                                  |                            |
     2590       2600       |2610       2620       2630       2640
       *          *         *|*          *          *        *|*
CCAGGCGTTT CCCCCTGGAA GCTCCCTCGT GCGCTCTCCT GTTCCGACCC TGCCGCTTAC
_____e_____e___PUC19 BACKBONE____e_____e_____>

>HaeII              >SfcI
                                            |                   |
     2650       2660       2670       2680 | 2690       2700
       *          *          *          * | *  *          * |*
CGGATACCTG TCCGCCTTTC TCCCTTCGGG AAGCGTGGCG CTTTCTCAAT GCTCACGCTG
_____e_____e___PUC19 BACKBONE____e_____e_____>

>BsiHKAI
                                                      |
                                           >ApaLI     |
                                              |       |
     2710       2720       2730       2740       2750 |    2760
       *          *          *          *        * | * |    *
TAGGTATCTC AGTTCGGTGT AGGTCGTTCG CTCCAAGCTG GGCTGTGTGC ACGAACCCCC
_____e_____e___PUC19 BACKBONE____e_____e_____>
```

*FIG. 8*
(CONTINUED)

```
          >BsiEI          >BsaWI
            |               |
    2770    |    2780     | 2790       2800        2810        2820
      *    *  | *     *    *|   *      *     *     *     *     *     *
CGTTCAGCCC GACCGCTGCG CCTTATCCGG TAACTATCGT CTTGAGTCCA ACCCGGTAAG
_____e_____e___PUC19 BACKBONE____e_____e_____>

>AlwNI
                                |
    2830        2840         2850        2860        2870        2880
      *     *     *     *     *|  *      *     *     *     *     *     *
ACACGACTTA TCGCCACTGG CAGCAGCCAC TGGTAACAGG ATTAGCAGAG CGAGGTATGT
_____e_____e___PUC19 BACKBONE____e_____e_____>

>SfcI
        |
    2890|       2900        2910        2920        2930        2940
      * |*      *     *     *     *     *     *     *     *     *     *
AGGCGGTGCT ACAGAGTTCT TGAAGTGGTG GCCTAACTAC GGCTACACTA GAAGGACAGT
_____e_____e___PUC19 BACKBONE____e_____e_____>

>Eco57I
                                            |
    2950        2960        2970        2980|       2990        3000
      *     *     *     *     *     *     * |   *   *     *     *     *
ATTTGGTATC TGCGCTCTGC TGAAGCCAGT TACCTTCGGA AAAAGAGTTG GTAGCTCTTG
_____e_____e___PUC19 BACKBONE____e_____e_____>

3010        3020        3030        3040        3050        3060
      *     *     *     *     *     *     *     *     *     *     *     *
ATCCGGCAAA CAAACCACCG CTGGTAGCGG TGGTTTTTTT GTTTGCAAGC AGCAGATTAC
_____e_____e___PUC19 BACKBONE____e_____e_____>

3070        3080        3090        3100        3110        3120
      *     *     *     *     *     *     *     *     *     *     *     *
GCGCAGAAAA AAAGGATCTC AAGAAGATCC TTTGATCTTT TCTACGGGGT CTGACGCTCA
_____e_____e___PUC19 BACKBONE____e_____e_____>

>BspHI
                                        |
    3130        3140        3150        | 3160      3170        3180
      *     *     *     *     *     *   |  *  *     *     *     *     *
GTGGAACGAA AACTCACGTT AAGGGATTTT GGTCATGAGA TTATCAAAAA GGATCTTCAC
_____e_____e___PUC19 BACKBONE____e_____e_____>

>DraI             >DraI
        |                 |
    3190|       3200    3210|       3220        3230        3240
      * |*      *     *    *|  *    *     *     *     *     *     *
CTAGATCCTT TTAAATTAAA AATGAAGTTT TAAATCAATC TAAAGTATAT ATGAGTAAAC
_____e_____e___PUC19 BACKBONE____e_____e_____>

>BanI
                                |
    3250        3260        3270|       3280        3290        3300
      *     *     *     *     * |*      *     *     *     *     *     *
TTGGTCTGAC AGTTACCAAT GCTTAATCAG TGAGGCACCT ATCTCAGCGA TCTGTCTATT
_____a_____a_____a_AMP-ORF_a_____a_____>
_____e_____e___PUC19 BACKBONE____e_____e_____>
```

FIG. 8
(CONTINUED)

```
                    >AhdI
                    |
    3310       3320 | 3330      3340       3350       3360
  *    *    *    * *|  *    *    *    *    *    *    *    *
TCGTTCATCC ATAGTTGCCT GACTCCCCGT CGTGTAGATA ACTACGATAC GGGAGGGCTT
_____a_____ _____a_____ AMP-ORF _____a_____ _____a_____>
_____e_____ _____e_____PUC19 BACKBONE_____e_____ _____e_____>

>BsaI
                     |
                     >BsrDI    >BpmI       >BsrFI
                     |         |           |
    3370       3380       3390 |   3400    |3410       3420
  *    *    *    *    *  | *    *| *    *  |  *    *    *
ACCATCTGGC CCCAGTGCTG CAATGATACC GCGAGACCCA CGCTCACCGG CTCCAGATTT
_____a_____ _____a_____ AMP-ORF _____a_____ _____a_____>
_____e_____ _____e_____PUC19 BACKBONE_____e_____ _____e_____>

>BglI
                |
    3430     3440|  3450      3460       3470       3480
  *    *    *  | *    *    *    *    *    *    *    *
ATCAGCAATA AACCAGCCAG CCGGAAGGGC CGAGCGCAGA AGTGGTCCTG CAACTTTATC
_____a_____ _____a_____ AMP-ORF _____a_____ _____a_____>
_____e_____ _____e_____PUC19 BACKBONE_____e_____ _____e_____>

>AseI
           |
    3490   3500        3510       3520       3530       3540
  *    *    *  | *    *    *    *    *    *    *    *
CGCCTCCATC CAGTCTATTA ATTGTTGCCG GGAAGCTAGA GTAAGTAGTT CGCCAGTTAA
_____a_____ _____a_____ AMP-ORF _____a_____ _____a_____>
_____e_____ _____e_____PUC19 BACKBONE_____e_____ _____e_____>

>Psp1406I
        |
>FspI   |     >BsrDI    >SfcI      >MslI
|       |     |         |          |
    3550|     3560 |        3570   |    3580       3590       3600
  *  | *    *  | *    *  | *    *    *  | *    *    *    *    *
TAGTTTGCGC AACGTTGTTG CCATTGCTAC AGGCATCGTG GTGTCACGCT CGTCGTTTGG
_____a_____ _____a_____ AMP-ORF _____a_____ _____a_____>
_____e_____ _____e_____PUC19 BACKBONE_____e_____ _____e_____>

>BsaWI
            |
    3610    3620|       3630       3640       3650       3660
  *    *    *  | *    *    *    *    *    *    *    *
TATGGCTTCA TTCAGCTCCG GTTCCCAACG ATCAAGGCGA GTTACATGAT CCCCCATGTT
_____a_____ _____a_____ AMP-ORF _____a_____ _____a_____>
_____e_____ _____e_____PUC19 BACKBONE_____e_____ _____e_____>

>BsiEI
                                |
                                >PvuI                      >EaeI
                                |                          |
    3670       3680       3690  |     3700       3710      | 3720
  *    *    *    *    *    *  |*    *    *    *    *    |*    *
GTGCAAAAAA GCGGTTAGCT CCTTCGGTCC TCCGATCGTT GTCAGAAGTA AGTTGGCCGC
_____a_____ _____a_____ AMP-ORF _____a_____ _____a_____>
_____e_____ _____e_____PUC19 BACKBONE_____e_____ _____e_____>
```

FIG. 8
(CONTINUED)

```
                    >MslI
                     |
    3730     3740    |    3750         3760         3770         3780
 *      *    *  | *     *       *    *       *    *       *    *       *
AGTGTTATCA CTCATGGTTA TGGCAGCACT GCATAATTCT CTTACTGTCA TGCCATCCGT
           a          a          AMP-ORF    a          a               >
_____e_____e_____PUC19 BACKBONE___e_____e_____>

>ScaI
                               |
    3790         3800         |3810         3820         3830         3840
 *      *    *       *    *  | *     *       *    *       *    *       *
AAGATGCTTT TCTGTGACTG GTGAGTACTC AACCAAGTCA TTCTGAGAAT AGTGTATGCG
           a          a          AMP-ORF    a          a               >
_____e_____e_____PUC19 BACKBONE___e_____e_____>

>BsiEI
   |
   | 3850         3860         3870         3880         3890         3900
 * |  *    *       *    *       *    *       *    *       *    *       *
GCGACCGAGT TGCTCTTGCC CGGCGTCAAT ACGGGATAAT ACCGCGCCAC ATAGCAGAAC
           a          a          AMP-ORF    a          a               >
_____e_____e_____PUC19 BACKBONE___e_____e_____>

>Pspl406I
                           |
 >DraI    >BsiHKAI         >XmnI
   |        |               |
   | 3910   | 3920          |3930         3940         3950         3960
 * |  *    *|  *       *    *     *       *    *       *    *       *
TTTAAAAGTG CTCATCATTG GAAAACGTTC TTCGGGGCGA AAACTCTCAA GGATCTTACC
           a          a          AMP-ORF    a          a               >
_____e_____e_____PUC19 BACKBONE___e_____e_____>

>Eco57I
                                              |
                                           >ApaLI
                                              |
                     >BssSI     |>BsiHKAI
                         |       |  |
    3970         3980         3990 |        4000         4010         4020
 *      *    *       *    *       *| *  | *    *       *    *       *
GCTGTTGAGA TCCAGTTCGA TGTAACCCAC TCGTGCACCC AACTGATCTT CAGCATCTTT
           a          a          AMP-ORF    a          a               >
_____e_____e_____PUC19 BACKBONE___e_____e_____>

4030         4040         4050         4060         4070         4080
 *      *    *       *    *       *    *       *    *       *    *       *
TACTTTCACC AGCGTTTCTG GGTGAGCAAA AACAGGAAGG CAAAATGCCG CAAAAAAGGG
           a          a          AMP-ORF    a          a               >
_____e_____e_____PUC19 BACKBONE___e_____e_____>

>MslI                              >EarI    >SspI
                |                                  |        |
    4090       |4100         4110         4120  |  4130    4140
 *      *    * | *    *       *    *       *    * | *    *       *
AATAAGGGCG ACACGGAAAT GTTGAATACT CATACTCTTC CTTTTTCAAT ATTATTGAAG
           a          AMP-ORF             a      >
_____e_____e_____PUC19 BACKBONE___e_____e_____>
```

FIG. 8
(CONTINUED)

```
                    >BspHI     >BsrBI
                       |          |
         4150       4160 |     4170        4180         4190         4200
     *      *    *      * |   * |  *     *       *    *       *    *       *
    CATTTATCAG GGTTATTGTC TCATGAGCGG ATACATATTT GAATGTATTT AGAAAAATAA
    _____e_____e___PUC19 BACKBONE____e_____e_____>
                                                              >HincII
                                                                 |
                                                              >AccI
                                                                 ||
                                                              >AatII
                                                                 ||
                                                              >SalI
                                                                 |||
         4210         4220         4230         4240             |||
     *       *    *       *    *       *    *       *    *      |||
    ACAAATAGGG GTTCCGCGCA CATTTCCCCG AAAAGTGCCA CCTGACGTC
    _____e_____PUC19 BACKBONE_____e_____>
```

RETINOBLASTOMA FUSION POLYPEPTIDES

This application is a continuation-in-part of U.S. Ser. No. 08/751,517, filed Nov. 15, 1996, abandoned.

BACKGROUND OF THE INVENTION

Both the retinoblastoma gene (RB) and transcription factor E2F play a critical role in cell growth control (for a review, see Adams, P. & Kaelin, W. *Seminars in Cancer Biology* 6:99–108 (1995)). The RB locus is frequently inactivated in a variety of human tumor cells. Reintroduction of a wild-type RB gene (e.g., Bookstein et al. *Science* 247:712–715 (1990)) or RB protein (pRB) (e.g., Antelman et al. *Oncogene* 10:697–704(1995)) into RBneg/RBmut cells can suppress growth in culture and tumorigenicity in vivo.

While E2F serves to activate transcription of S-phase genes, its activity is kept in check by RB. RB arrests cells by blocking exit from G into S-phase (for example, Dowdy et al. *Cell* 73:499–511 (1993)) but the precise pathway of the arrest remains unclear.

Although E2F forms complexes with RB, complex formation is more efficient if an E2F-related protein, DP-1, is present. E2F-1 and DP-1 form stable heterodimers which bind to DNA (for example, Qin et al. *Genes and Dev.* 6-:953–964 (1992)). DP-1-E2F complexes serve to cooperatively activate transcription of E2F-dependent genes. Such transcription can be repressed by pRB in the same manner as E2F-1 or DP-1 activated transcription.

Transcriptional repression of genes by RB in some instances can be achieved by tethering pRB to a promoter. For example, GAL4-pRB fusions bind to GAL4 DNA binding domains and repress transcription from p53, Sp-1 or AP-1 elements (Adnane, et al. *J. Biol. Chem.* 270:8837–8843 (1995); Weintraub, et al. *Nature* 358:259–261 (1995)). Sellers, et al. (*Proc. Natl. Acad. Sci.* 92:11544–11548 (1995)) disclosed fusions of amino acid residues 1–368 of E2F with amino acids 379–792 or 379–928 of RB.

Chang, et al. (*Science* 267:518–522 (1995)) disclosed the use of a replication-defective adenovirus-RB construct in the reduction of neointima formation in two animal models of restenosis, a hyperproliferative disorders.

SUMMARY OF THE INVENTION

The instant invention provides the surprising result that a fusion of an E2F polypeptide with an RB polypeptide is more efficient in repressing transcription of the E2F promoter than RB alone, and that such fusions can cause cell cycle arrest in a variety of cell types. Such fusions can thus address the urgent need for therapy of hyperproliferative disorders, including cancer.

One aspect of the invention is a polypeptide comprising a fusion of a transcription factor, the transcription factor comprising a DNA binding domain, and a retinoblastoma (RB) polypeptide, the RB polypeptide comprising a growth suppression domain. Another aspect of the invention is DNA encoding such a fusion polypeptide. The DNA can be inserted in an adenovirus vector.

In some embodiments of the invention, the transcription factor is E2F. The cyclin A binding domain of the E2F can be deleted or nonfunctional. The E2F can comprise amino acid residues about 95 to about 194 or about 95 to about 286 in some embodiments.

The retinoblastoma polypeptide can be wild-type RB, RB56, or a variant or fragment thereof. In some embodiments, the retinoblastoma polypeptide comprises amino acid residues of about 379 to about 928. Preferred amino acid substitutions of the RB polypeptide include residues 2, 608, 788, 807, and 811.

Another aspect of the invention is an expression vector comprising DNA encoding a polypeptide, the polypeptide comprising a fusion of a transcription factor, the transcription factor comprising a DNA binding domain, and a retinoblastoma (RB) polypeptide, the RB polypeptide comprising a growth suppression domain. In some embodiments a tissue-specific promoter is operatively linked to DNA encoding the fusion polypeptide. The tissue-specific promoter can be a smooth muscle alpha actin promoter.

Another aspect of the invention is a method for treatment of hyperproliferative disorders comprising administering to a patient a therapeutically effective dose of an E2F-RB fusion polypeptide. The hyperproliferative disorder can be cancer. In some embodiments the hyperproliferative disorder is restenosis. The fusion polypeptide and nucleic acid encoding the fusion polypeptide can be used to coat devices used for angioplasty.

BRIEF DESCRIPTION OF THE DRAWINGS

The file of this patent contains at least one drawing executed in color. Copies of this patent with color drawings (s) will be provided by the Patent and Trademark Office upon request and payment of the necessary fee.

FIG. 1A (SEQ ID NO:1) depicts the predicted amino acid sequence of E2F.

FIG. 1B (SEQ ID NO:2) depicts the nucleotide sequence of transcription factor E2F.

FIG. 2A (SEQ ID NO:3) depicts the nucleotide sequence of pRB as disclosed by Lee, et al. (*Nature* 329:642–645 (1987).

FIG. 2B (SEQ ID NO:4) depicts the predicted amino acid sequence of pRB.

FIG. 4 (SEQ ID NOS:5–18) depicts the nucleotide sequence of plasmid pCTM.

FIG. 6 (SEQ ID NO:19–32) depicts the nucleotide sequence of pCTMI.

FIG. 8 (SEQ ID NOS:33–46) depicts the nucleotide sequence of pCTMIE.

DESCRIPTION OF THE PREFERRED EMBODIMENT

Figure 3:
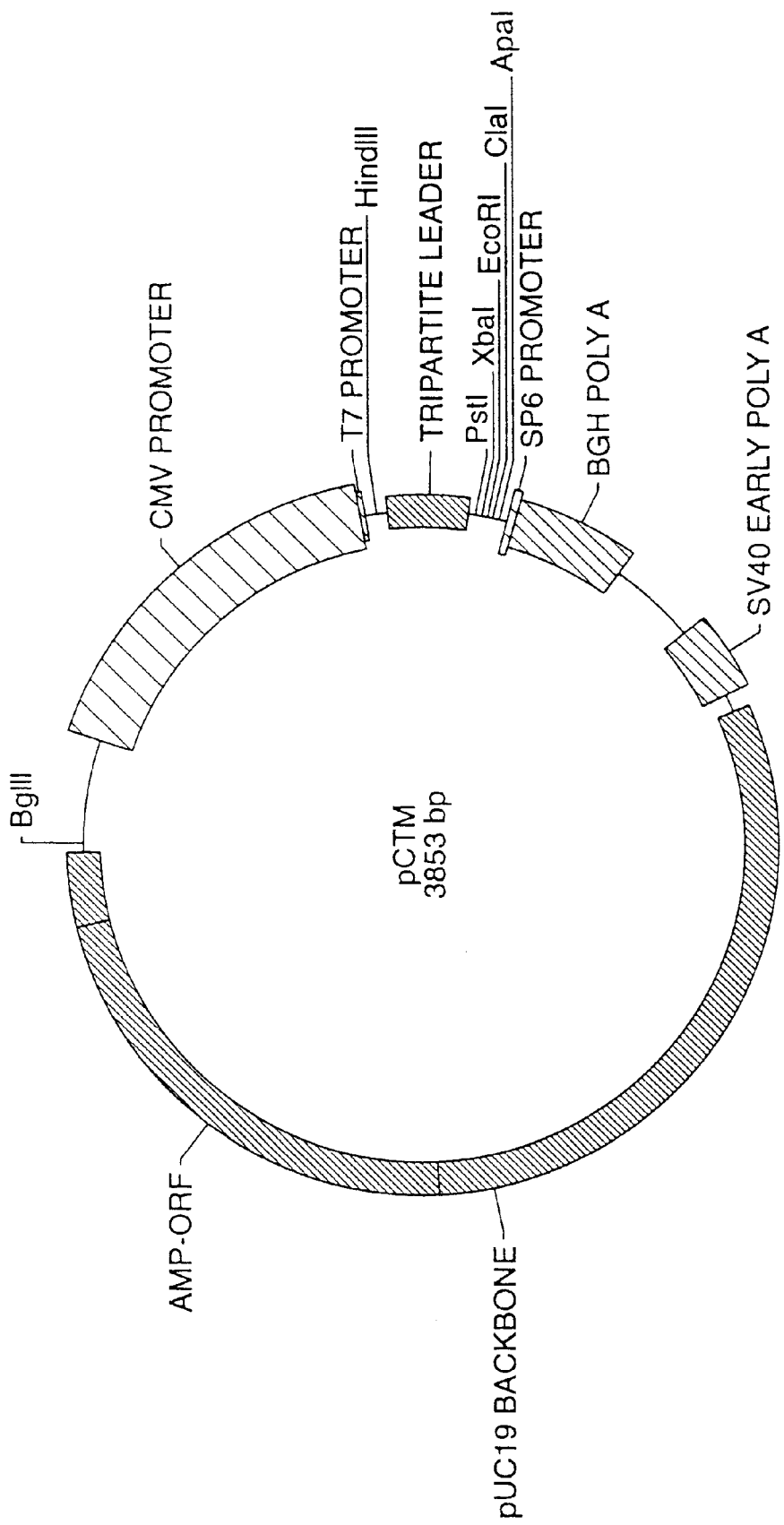
FIG. 3 is a diagrammatic representation of pCTM.

The instant invention provides RB fusion constructs including fusion polypeptides and vectors encoding them, and methods for the use of such constructs in the treatment of hyperproliferative diseases. In some preferred embodiments of the invention, an RB polypeptide is fused to an E2F polypeptide. Any E2F species can be used, typically E2F-1, -2, -3, -3, or -5 (see, e.g., Wu et al. *Mol Cell. Biol.* 15:2536–2546 (1995); Ivey-Hoyle et al. *Mol. Cell. Biol.* 13:7802 (1993); Vairo et al. *Genes and Dev.* 9:869 (1995); Beijersbergen et al. *Genes and Dev.* 8:2680 (1994)); Ginsberg et al. *Genes and Dev.* 8:2665 (1994); Buck et al. Oncogene 11:31 (1995)), more typically E2F-1. Typically, the E2F polypeptide comprises at least the DNA binding domain of E2F, and may optionally include the cyclin A binding domain, the heterodimerization domain, and/or the transactivation domain. Preferably, the cyclin A binding domain is not functional. The nucleotide and amino acid sequence of E2F referred to herein are those of Genbank HUME2F, shown in FIGS. 1A and 1B. Nucleic acid, preferably DNA, encoding such an EF2 polypeptide is fused in reading frame to an RB polypeptide. The RB polypeptide can be any RB polypeptide, including conservative amino acid variants, allelic variants, amino acid substitution, deletion, or insertion mutants, or fragments thereof. Preferably, the growth suppression domain, i.e., amino acids residues 379–928, of the RB polypeptide is functional (Hiebert, et al. *MCB* 13:3384–3391 (1993); Qin, et al. *Genes and Dev.* 6:953–964 (1992)). In some embodiments, wild-type pRB110 is used. More preferably, a truncated version of RB, RB56, is used. RB56 comprises amino acid residues 379–928 of pRB110 (Hiebert, et al. *MCB* 13:3384–3391 (1993); Qin, et al. *Genes and Dev.* 6:953–964 (1992)). In some embodiments, amino acid variants of RB at positions 2, 608, 612, 788, 807, or 811, are used singly or in combination. The variant RB56-5s comprises wild-type RB56 having alanine substitutions at 608, 612, 788, 807, and 811.

Numbering of RB amino acids and nucleotides is according to the RB sequence disclosed by Lee, et al. (*Nature* 329:642–645 (1987)), hereby incorporated by reference in its entirety for all purposes. (FIG. 2).

Nucleic acids encoding the polypeptides of the invention can be DNA or RNA. The phrase "nucleic acid sequence encoding" refers to a nucleic acid which directs the expression of a specific protein or peptide. The nucleic acid sequences include both the DNA strand sequence that is transcribed into RNA and the RNA sequence that is translated into protein. The nucleic acid sequences include both the full length nucleic acid sequences as well as non-full length sequences derived from the full length protein. It is further understood that the sequence includes the degenerate codons of the native sequence or sequences which may be introduced to provide codon preference in a specific host cell.

The term "vector" as used herein refers to viral expression systems, autonomous self-replicating circular DNA (plasmids), and includes both expression and nonexpression plasmids. Where a recombinant microorganism or cell culture is described as hosting an "expression vector," this includes both extrachromosomal circular DNA and DNA that has been incorporated into the host chromosome(s). Where a vector is being maintained by a host cell, the vector may either be stably replicated by the cells during mitosis as an autonomous structure, or is incorporated within the host's genome. A vector contains multiple genetic elements positionally and sequentially oriented, i.e., operatively linked with other necessary elements such that nucleic acid in the vector encoding the constructs of the invention can be transcribed, and when necessary, translated in transfected cells.

The term "gene" as used herein is intended to refer to a nucleic acid sequence which encodes a polypeptide. This definition includes various sequence polymorphisms, mutations, and/or sequence variants wherein such alterations do not affect the function of the gene product. The term "gene" is intended to include not only coding sequences but also regulatory regions such as promoters, enhancers, and termination regions. The term further includes all introns and other DNA sequences spliced from the mRNA transcript, along with variants resulting from alternative splice sites.

The term "plasmid" refers to an autonomous circular DNA molecule capable of replication in a cell, and includes both the expression and nonexpression types. Where a recombinant microorganism or cell culture is described as hosting an "expression plasmid", this includes both extrachromosomal circular DNA molecules and DNA that has been incorporated into the host chromosome(s). Where a plasmid is being maintained by a host cell, the plasmid is either being stably replicated by the cells during mitosis as an autonomous structure or is incorporated within the host's genome.

The phrase "recombinant protein" or "recombinantly produced protein" refers to a peptide or protein produced using non-native cells that do not have an endogenous copy of DNA able to express the protein. The cells produce the protein because they have been genetically altered by the introduction of the appropriate nucleic acid sequence. The recombinant protein will not be found in association with proteins and other subcellular components normally associated with the cells producing the protein. The terms "protein" and "polypeptide" are used interchangeably herein.

In general, a construct of the invention is provided in an expression vector comprising the following elements linked sequentially at appropriate distances for functional expression: a tissue-specific promoter, an initiation site for transcription, a 3' untranslated region, a 5' mRNA leader sequence, a nucleic acid sequence encoding a polypeptide of the invention, and a polyadenylation signal. Such linkage is termed "operatively linked." Enhancer sequences and other sequences aiding expression and/or secretion can also be included in the expression vector. Additional genes, such as those encoding drug resistance, can be included to allow selection or screening for the presence of the recombinant vector. Such additional genes can include, for example, genes encoding neomycin resistance, multi-drug resistance, thymidine kinase, beta-galactosidase, dihydrofolate reductase (DHFR), and chloramphenicol acetyl transferase.

In the instant invention, tissue-specific expression of the RB constructs of the invention is preferably accomplished by the use of a promoter preferentially used by a tissue of interest. Examples of tissue-specific promoters include the promoter for creatine kinase, which has been used to direct the expression of dystrophin cDNA expression in muscle and cardiac tissue (Cox, et al. *Nature* 364:725–729 (1993)) and immunoglobulin heavy or light chain promoters for the expression of suicide genes in B cells (Maxwell, et al. *Cancer Res.* 51:4299–4304 (1991)). An endothelial cell-specific regulatory region has also been characterized (Jahroudi, et al. *Mol. Cell. Biol.* 14:999–1008 (1994)). Amphotrophic retroviral vectors have been constructed carrying a herpes simplex virus thymidine kinase gene under the control of either the albumin or alpha-fetoprotein promoters (Huber, et al. *Proc. Natl. Acad. Sci. U.S.A.* 88:8039–8043 (1991)) to target cells of liver lineage and hepatoma cells, respectively. Such tissue specific promoters can be used in retroviral vectors (Harzoglou, et al. *J. Biol. Chem*, 265:17285–17293 (1990)) and adenovirus vectors (Friedman, et al. *Mol. Cell. Biol.* 6:3791–3797 (1986); Wills et al. *Cancer Gene Therapy* 3:191–197 (1995)) and still retain their tissue specificity.

In the instant invention, a preferred promoter for tissue-specific expression of exogenous genes is the human smooth muscle alpha-actin promoter. Reddy, et al. (*J. Cell Biology* 265:1683–1687 (1990)) disclosed the isolation and nucleotide sequence of this promoter, while Nakano, et al. (*Gene* 99:285–289 (1991)) disclosed transcriptional regulatory elements in the 5' upstream and the first intron regions of the human smooth muscle (aortic type) alpha-actin gene.

Petropoulos, et al. (*J. Virol.* 66:3391–3397 (1992)) disclosed a comparison of expression of bacterial chloramphenicol transferase (CAT) operatively linked to either the chicken skeletal muscle alpha actin promoter or the cytoplasmic beta-actin promoter. These constructs were provided in a retroviral vector and used to infect chicken eggs.

Exemplary tissue-specific expression elements for the liver include but are not limited to HMG-COA reductase promoter (Luskey, *Mol. Cell. Biol.* 7(5):1881–1893 (1987)); sterol regulatory element 1 (SRE-1; Smith et al. *J. Biol. Chem.* 265(4):2306–2310 (1990); phosphoenol pyruvate carboxy kinase (PEPCK) promoter (Eisenberger et al. *Mol. Cell Biol.* 12(3):1396–1403 (1992)); human C-reactive protein (CRP) promoter (Li et al. *J. Biol. Chem.* 265(7):4136–4142 (1990)); human glucokinase promoter (Tanizawa et al. *Mol. Endocrinology* 6(7):1070–81 (1992); cholesterol 7-alpha hydroylase (CYP-7) promoter (Lee et al. *J. Biol. Chem.* 269(20):14681–9 (1994)); beta-galactosidase alpha-2,6 sialyltransferase promoter (Svensson et al. *J. Biol. Chem.* 265(34):20863–8 (1990); insulin-like growth factor binding protein (IGFBP-1) promoter (Babajko et al. *Biochem Biophys. Res. Comm.* 196 (1):480–6 (1993)); aldolase B promoter (Bingle et al. *Biochem J.* 294(Pt2):473–9 (1993)); human transferrin promoter (Mendelzon et al. *Nucl. Acids Res.* 18(19):5717–21 (1990); collagen type I promoter (Houglum et al. *J. Clin. Invest.* 94(2):808–14 (1994)).

Exemplary tissue-specific expression elements for the prostate include but are not limited to the prostatic acid phosphatase (PAP) promoter (Banas et al. *Biochim. Biophys. Acta.* 1217(2):188–94 (1994); prostatic secretory protein of 94 (PSP 94) promoter (Nolet et al. *Biochim. Biophys. ACTA* 1089(2):247–9 (1991)); prostate specific antigen complex promoter (Kasper et al. *J. Steroid Biochem. Mol. Biol.* 47 (1–6):127–35 (1993)); human glandular kallikrein gene promoter (hgt-1) (Lilja et al. *World J. Urology* 11(4):188–91 (1993).

Exemplary tissue-specific expression elements for gastric tissue include but are not limited to the human $H^+/K^+$-ATPase alpha subunit promoter (Tamura et al. *FEBS Letters* 298: (2–3):137–41 (1992)).

Exemplary tissue-specific expression elements for the pancreas include but are not limited to pancreatitis associated protein promoter (PAP) (Dusetti et al. *J. Biol. Chem.* 268(19):14470–5 (1993)); elastase 1 transcriptional enhancer (Kruse et al. *Genes and Development* 7(5):774–86 (1993)); pancreas specific amylase and elastase enhancer promoter (Wu et al. *Mol. Cell. Biol.* 11(9):4423–30 (1991); Keller et al. *Genes & Dev.* 4(8):1316–21 (1990)); pancreatic cholesterol esterase gene promoter (Fontaine et al. *Biochemistry* 30(28):7008–14 (1991)).

Exemplary tissue-specific expression elements for the endometrium include but are not limited to the uteroglobin promoter (Helftenbein et al. *Annal. NY Acad. Sci.* 622:69–79 (1991)).

Exemplary tissue-specific expression elements for adrenal cells include but are not limited to cholesterol side-chain cleavage (SCC) promoter (Rice et al. *J. Biol. Chem.* 265:11713–20 (1990).

Exemplary tissue-specific expression elements for the general nervous system include but are not limited to gamma-gamma enolase (neuron-specific enolase, NSE) promoter (Forss-Petter et al. *Neuron* 5(2):187–97 (1990)).

Exemplary tissue-specific expression elements for the brain include but are not limited to the neurofilament heavy chain (NF-H) promoter (Schwartz et al. *J. Biol. Chem.* 269(18):13444–50 (1994)).

Exemplary tissue-specific expression elements for lymphocytes include but are not limited to the human CGL-1/granzyme B promoter (Hanson et al. *J. Biol. Chem.* 266 (36):24433–8 (1991)); the terminal deoxy transferase (TdT), lambda 5, VpreB, and lck (lymphocyte specific tyrosine protein kinase p56lck) promoter (Lo et al. *Mol. Cell. Biol.* 11(10):5229–43 (1991)); the humans CD2 promoter and its 3'transcriptional enhancer (Lake et al. *EMBO J.* 9(10):3129–36 (1990)), and the human NK and T cell specific activation (NKG5) promoter (Houchins et al. *Immunogenetics* 37(2):102–7 (1993)).

Exemplary tissue-specific expression elements for the colon include but are not limited to pp60c-src tyrosine kinase promoter (Talamonti et al. *J. Clin. Invest* 91(1):53–60 (1993)); organ-specific neoantigens (OSNs), mw 40 kDa (p40) promoter (Ilantzis et al. *Microbiol. Immunol.* 37(2):119–28 (1993)); colon specific antigen-P promoter (Sharkey et al. *Cancer* 73(3 supp.) 864–77 (1994)).

Exemplary tissue-specific expression elements for breast cells include but are not limited to the human alpha-lactalbumin promoter (Thean et al. *British J. Cancer.* 61(5):773–5 (1990))

Other elements aiding specificity of expression in a tissue of interest can include secretion leader sequences, enhancers, nuclear localization signals, endosmolytic peptides, etc. Preferably, these elements are derived from the tissue of interest to aid specificity.

Techniques for nucleic acid manipulation of the nucleic acid sequences of the invention such as subcloning nucleic acid sequences encoding polypeptides into expression vectors, labelling probes, DNA hybridization, and the like are described generally in Sambrook et al., *Molecular Cloning—A Laboratory Manual* (2nd Ed.), Vol. 1–3, Cold Spring Harbor Laboratory, Cold Spring Harbor, N.Y., (1989), which is incorporated herein by reference. This manual is hereinafter referred to as "Sambrook et al.,"

Once DNA encoding a sequence of interest is isolated and cloned, one can express the encoded proteins in a variety of recombinantly engineered cells. It is expected that those of skill in the art are knowledgeable in the numerous expression systems available for expression of DNA encoding. No attempt to describe in detail the various methods known for the expression of proteins in prokaryotes or eukaryotes is made here.

In brief summary, the expression of natural or synthetic nucleic acids encoding a sequence of interest will typically be achieved by operably linking the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of polynucleotide sequence of interest. To obtain high level expression of a cloned gene, it is desirable to construct expression plasmids which contain, at the minimum, strong promoter to direct transcription, a ribosome binding site for translational initiation, and a transcription/translation terminator. The expression vectors may also comprise generic expression cassettes containing at least one independent terminator sequence, sequences permitting replication of the plasmid in both eukaryotes and prokaryotes, i.e., shuttle vectors, and selection markers for both prokaryotic and eukaryotic systems. See Sambrook et al.

The E2F-RB fusion constructs of the invention can be introduced into the tissue of interest in vivo or ex vivo by a variety of methods. In some embodiments of the invention, the nucleic acid, preferably DNA, is introduced to cells by such methods as microinjection, calcium phosphate precipitation, liposome fusion, or biolistics. In further embodiments, the DNA is taken up directly by the tissue of interest. In other embodiments, the constructs are packaged into a viral vector system to facilitate introduction into cells.

Viral vector systems useful in the practice of the instant invention include adenovirus, herpesvirus, adeno-associated virus, minute virus of mice (MVM), HIV, sindbis virus, and retroviruses such as Rous sarcoma virus, and MoMLV. Typically, the constructs of the instant invention are inserted into such vectors to allow packaging of the E2F-RB expression construct, typically with accompanying viral DNA, infection of a sensitive host cell, and expression of the E2F-RB gene. A particularly advantageous vector is the adenovirus vector disclosed in Wills, et al. *Human Gene Therapy* 5:1079–1088 (1994).

In still other embodiments of the invention, the recombinant DNA constructs of the invention are conjugated to a cell receptor ligand for facilitated uptake (e.g., invagination of coated pits and internalization of the endosome) through a DNA linking moiety (Wu, et al. *J. Biol. Chem.* 263:14621–14624 (1988); WO 92/06180). For example, the DNA constructs of the invention can be linked through a polylysine moiety to asialo-oromucocid, which is a ligand for the asialoglycoprotein receptor of hepatocytes.

Similarly, viral envelopes used for packaging the constructs of the invention can be modified by the addition of receptor ligands or antibodies specific for a receptor to permit receptor-mediated endocytosis into specific cells (e.g., WO 93/20221, WO 93/14188; WO 94/06923). In some embodiments of the invention, the DNA constructs of the invention are linked to viral proteins, such as adenovirus particles, to facilitate endocytosis (Curiel, et al. *Proc. Natl. Acad. Sci. U.S.A.* 88:8850–8854 (1991)). In other embodiments, molecular conjugates of the instant invention can include microtubule inhibitors (WO 94/06922); synthetic peptides mimicking influenza virus hemagglutinin (Plank, et al. *J. Biol. Chem.* 269:12918–12924 (1994)); and nuclear localization signals such as SV40 T antigen (WO 93/19768).

In some embodiments of the invention, the RB polypeptides of the invention are administered directly to a patient in need of treatment. A "therapeutically effective" dose is a dose of polypeptide sufficient to prevent or reduce severity of a hyperproliferative disorder. As used herein, the term "hyperproliferative cells" includes but is not limited to cells having the capacity for autonomous growth, i.e., existing and reproducing independently of normal regulatory mechanisms. Hyperproliferative diseases may be categorized as pathologic, i.e., deviating from normal cells, characterizing for constituting disease, or may be categorized as non-pathologic, i.e., deviation from normal but not associated with a disease state. Pathologic hyperproliferative cells are characteristic of the following disease states: restenosis, diabetic retinopathy, thyroid hyperplasia, Gravels disease, psoriasis, benign prostatic hypertrophy, Li-Fraumeni syndrome including breast cancer, sarcomas and other neoplasms, bladder cancer, colon cancer, lung cancer, various leukemias and lymphomas. Examples of non-pathological hyperproliferative cells are found, for instance, in mammary ductal epithelial cells during development of lactation and also in cells associated with wound repair. Pathological hyperproliferative cells characteristically exhibit loss of contact inhibition and a decline in their ability to selectively adhere which implies E further breakdown in intercellular communication. These changes include stimulation to divide and the ability to secrete proteolytic enzymes.

The constructs of the invention are useful in the therapy of various cancers and other conditions in which the administration of RB is advantageous, including but not limited to peripheral vascular diseases and diabetic retinopathy. Although any tissue can be targeted for which some tissue-specific expression element, such as a promoter, can be identified, of particular interest is the tissue-specific administration of an RB construct for hyperproliferative disorders such as restenosis, for which the smooth muscle actin promoter is preferable.

The compositions of the invention will be formulated for administration by manners known in the art acceptable for administration to a mammalian subject, preferably a human. In some embodiments of the invention, the compositions of the invention can be administered directly into a tissue by injection or into a blood vessel supplying the tissue of interest. In further embodiments of the invention the compositions of the invention are administered "locoregionally", i.e., intravesically, intralesionally, and/or topically. In other embodiments of the invention, the compositions of the invention are administered systemically by injection, inhalation, suppository, transdermal delivery, etc. In further embodiments of the invention, the compositions are administered through catheters or other devices to allow access to a remote tissue of interest, such as an internal organ. The compositions of the invention can also be administered in depot type devices, implants, or encapsulated formulations to allow slow or sustained release of the compositions.

The invention provides compositions for administration which comprise a solution of the compositions of the invention dissolved or suspended in an acceptable carrier, preferably an aqueous carrier. A variety of aqueous carriers may be used, e.g., water, buffered water, 0.8% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of the compositions of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

The compositions of the invention may also be administered via liposomes. Liposomes include emulsions, foams, micelles, insoluble monolayers, liquid crystals, phospholipid dispersions, lamellar layers and the like. In these preparations the composition of the invention to be delivered is incorporated as part of a liposome, alone or in conjunction with a molecule which binds to a desired target, such as antibody, or with other therapeutic or immunogenic compositions. Thus, liposomes either filled or decorated with a desired composition of the invention of the invention can delivered systemically, or can be directed to a tissue of interest, where the liposomes then deliver the selected therapeutic/immunogenic peptide compositions.

Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al. *Ann. Rev. Biophys. Bioeng.* 9:467 (1980), U.S. Pat. Nos. 4,235,871, 4,501,728, 4,837,028, and 5,019,369, incorporated herein by reference.

A liposome suspension containing a composition of the invention may be administered intravenously, locally, topically, etc. in a dose which varies according to, inter alia, the manner of administration, the composition of the invention being delivered, and the stage of the disease being treated.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient, that is, one or more compositions of the invention of the invention, and more preferably at a concentration of 25%–75%.

For aerosol administration, the compositions of the invention are preferably supplied in finely divided form along with a surfactant and propellant. Typical percentages of compositions of the invention are 0.01%–20% by weight, preferably 1%–10%. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%–20% by weight of the composition, preferably 0.25–5%. The balance of the composition is ordinarily propellant. A carrier can also be included, as desired, as with, e.g., lecithin for intranasal delivery.

The constructs of the invention can additionally be delivered in a depot-type system, an encapsulated form, or an implant by techniques well-known in the art. Similarly, the constructs can be delivered via a pump to a tissue of interest.

In some embodiments of the invention, the compositions of the invention are administered ex vivo to cells or tissues explanted from a patient, then returned to the patient. Examples of ex vivo administration of gene therapy constructs include Arteaga et al. *Cancer Research* 56(5):1098–1103 (1996); Nolta et al. *Proc Natl. Acad. Sci. USA* 93(6):2414–9 (1996); Koc et al. *Seminars in Oncology* 23 (1):46–65 (1996); Raper et al. *Annals of Surgery* 223(2):116–26 (1996); Dalesandro et al. *J. Thorac. Cardi. Surg.* 111(2):416–22 (1996); and Makarov et al. *Proc. Natl. Acad. Sci. USA* 93(1):402–6 (1996).

In some embodiments of the invention, the constructs of the invention are administered to a cardiac artery after balloon angioplasty to prevent or reduce the severity of restenosis. The constructs of the invention can be used to coat the device used for angioplasty (see, for example, Willard, et al. *Circulation* 89:2190–2197 (1994); French, et al. *Circulation* 90:2402–2413 (1994)). In further embodiments, the fusion polypeptides of the invention can be used in the same manner.

The following examples are included for illustrative purposes and should not be considered to limit the present invention.

EXAMPLES

Example I

E2F-RB Fusions

A. Introduction

In this example, expression plasmids which encode different segments of E2F fused to RB56 polypeptide were constructed. RB56 is a subfragment of full length RB which contains the "pocket" domains necessary for growth suppression (Hiebert, et al. *MCB* 13:3384–3391 (1993); Qin, et al. *Genes and Dev.* 6:953–964 (1992)). E2FI94 contains E2F amino acids 95–194. This fragment contains only the DNA binding domain of E2F. E2F286 contains the DNA binding domain and the DP-1 heterodimerization domain. Both E2F fragments lack the N-terminal cyclin A-kinase binding domain, which appears to down-regulate the DNA binding activity of E2F (Krek et al. *Cell* 83:1149–1158 (1995); Krek et al. *Cell* 78:161–172 (1994)).

B. Construction of Vectors

Figure 5:
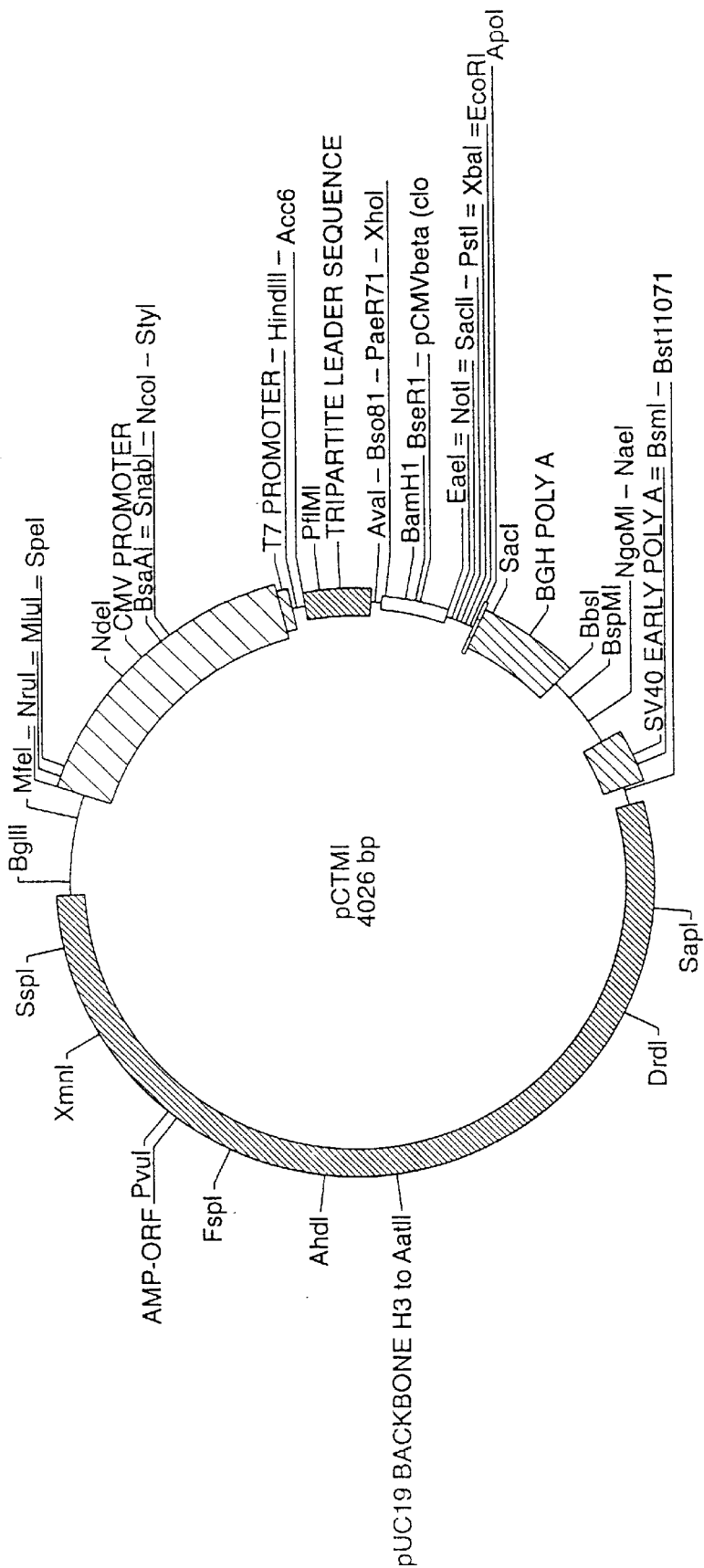
FIG. 5 is a diagrammatic representation of pCTMI.
Figure 7:
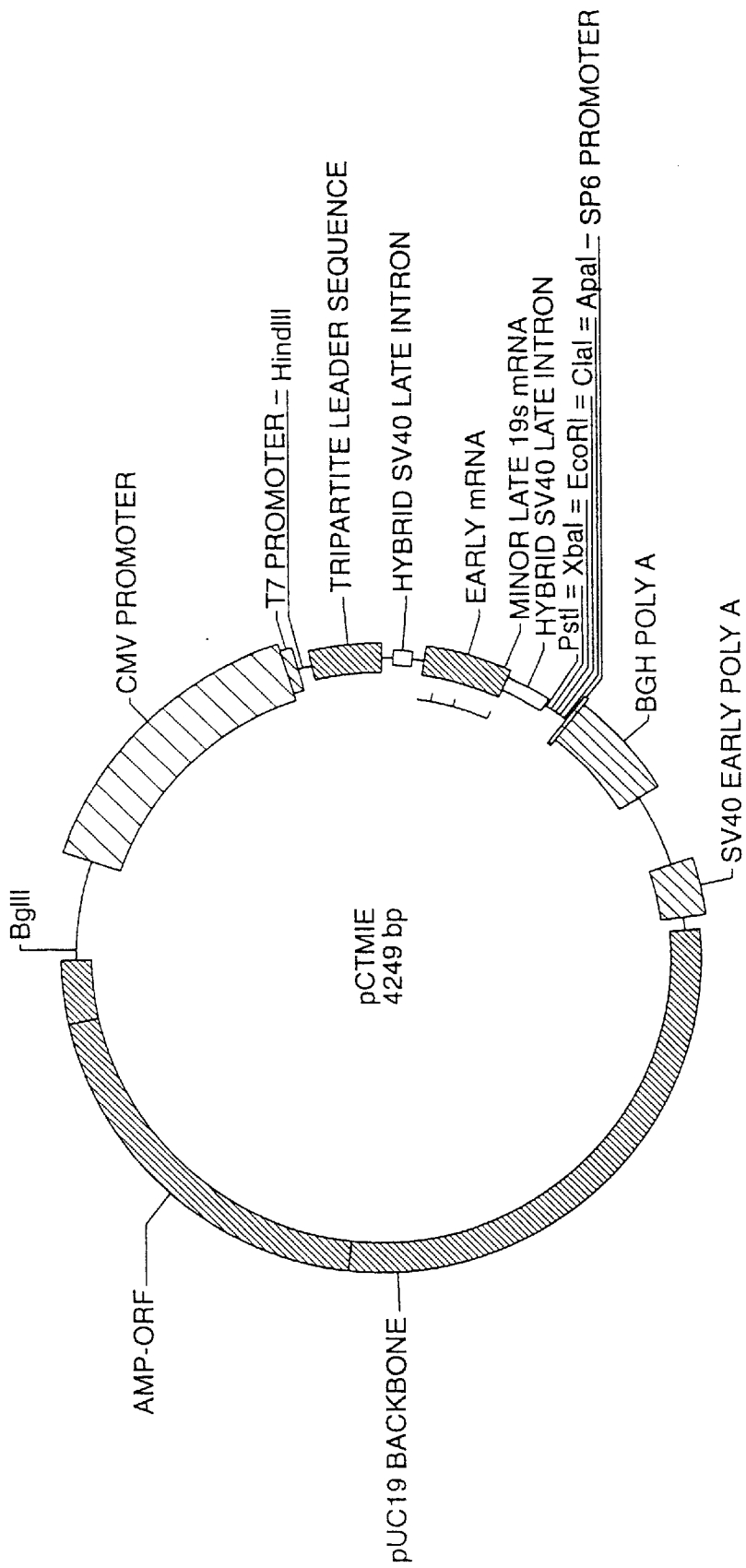
FIG. 7 is a diagrammatic representation of plasmid pCT-MIE.

Plasmid pCTM contains a CMV promoter, a tripartite adenovirus leader flanked by T7 and SP6 promoters, and a multiple cloning site with a bovine growth hormone (BGH) polyadenylation site and a SV-40 poly adenylation site downstream. A diagrammatic representation of pCTM is provided in FIG. 3. The DNA sequence for pCTM is provided in FIG. 4.

pCTMI was constructed from pCTM by digesting pCTM with Xho I and Not I and subcloning a 180 bp intron XhoI-Not I fragment from a pCMV-β-gal vector (Clonetech). A diagrammatic representation of pCTMI is provided in FIG. 5. The DNA sequence is provided in FIG. 6.

pCTMIE was constructed by amplifying the SV40 enhancer from SV40 viral DNA in a polymerase chain reaction. The amplified product was digested with BglII and inserted into BamH1-digested PCMTI and ligated in the presence of BamHI. The plasmid is depicted diagrammatically in FIG. 7. The DNA sequence is provided in FIG. 8.

pCTM-RB was prepared as follows. A 3.2 KB Xba I -Cla I fragment of pETRBc (Huang et al. *Nature* 350:160–162 (1991)) containing the full length human RB cDNA was ligated to Xba I-Cla I digested pCTM. pCTM-RB56 was prepared by ligating the digested pCTM to a 1.7 KB Xba 1-Cla I fragment containing the coding sequence for RB56. pCTMI-RB, pCTMIE-RB, pCTMI-RB56(amino acids 381–928) and pCTMIE-RB56(amino acids 381–928) were all constructed by the same methods.

C. RB-E2F Fusion Constructs

Figure 9:
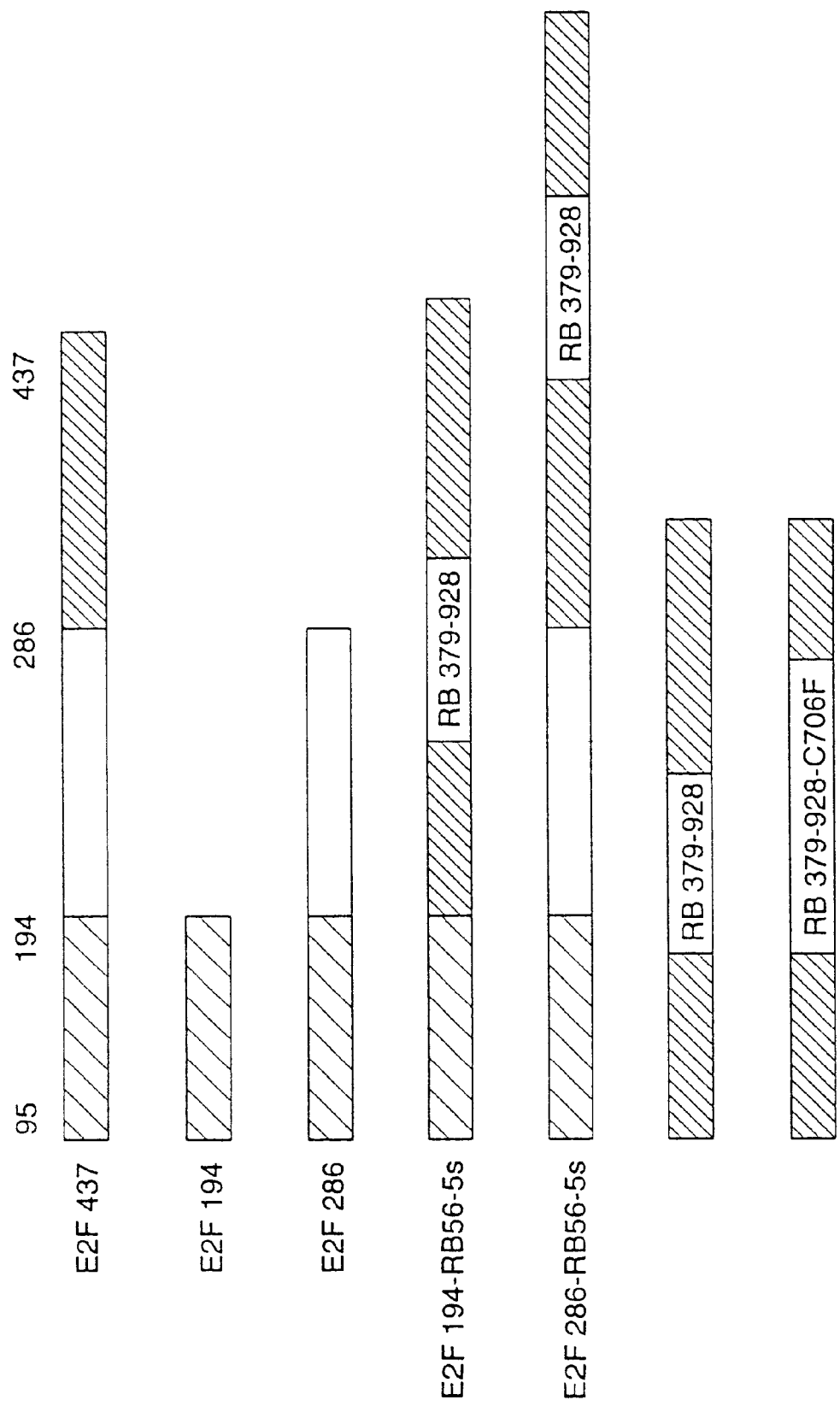
FIG. 9 is a diagram depicting E2F-RB fusion constructs used in the examples. All E2F constructs commenced at amino acid 95 and lacked part of the cyclin A binding domain. E2F-437 contained the DNA binding domain (black), heterodimerization domain (white), and the transactivation domain (stippled). E2F-194 contained solely the DNA binding domain. E2F-286 contained the DNA binding domain and the DP-1 heterodimerization domain. To generate E2F-194-RB56-5s and E2F-286-RB56-5s, the E2F constructs were fused in-frame to codon 379 of RB. Construct RB379-928-C706F has an is an inactivating point mutation.

FIG. 9 depicts the fusion constructs used in these studies. These E2F constructs commenced at amino acid 95 and lacked part of the cyclin A binding domain. E2F437 contained the DNA binding domain (black), heterodimerization domain (white) and transactivation domain (stippled). E2F194 contained solely the DNA binding domain. E2F286 contained the DNA binding domain and DP-1 heterodimerization domain. RB56-5s refers to an RB variant having alanine substitutions at amino acid residues 606, 612, 788, 807 and 811. In E2F194-RB56-5s and E2F286-RB56-5s, the E2F fragments were fused in frame to codon 379 of RB-5s. RB56-C706F contained an inactivating point mutation (Kaye et al. *Proc. Natl. Acad. Sci. U.S.A.* 87:6922–6926 (1990)).

pCMV-E2F194 and pCMV-E2F437 were constructed as follows. DNA encoding amino acids 95–194 of E2F (containing the DNA binding domain) or amino acids 95–437 was amplified in a polymerase chain reaction, digested with HindII, and ligated into SmaI/HindII digested pCMV-RB56 vectors. pCMVE2F286 was constructed by digesting pCMV-E2F437 with AflII, treating the ends with DNA pol I (Klenow fragment) and religating in the presence of AflII. The blunt end ligation created a stop codon at position 287. pCMV-E2F286-5s was constructed by ligating AflII (blunt)/HindIII digested pE2F437 to a Sal I (blunt)-HindIII fragment containing the RB56-5s coding sequence. pCTMIE-E2F194-5s and pCTMIE-E2F286-RB5s were constructed by ligating EcoRI-EcoRV digested pCTMIE (4.2 KB) to HindIII (blunt)-EcoRI fragments from either pCMV-E2F194-RB5s or pCMV-E2F286-RB5s.

D. Promoter Repression

To measure the effect of the E2F-RB fusion proteins, cervical carcinoma cell line C33A (ATCC # HTB-31) was transfected with equivalent amounts of E2F194-RB56 or E2F RB56 with an E2-CAT reporter plasmid (See, e.g., Weintraub et al. *Nature* 358:259–261 (1992)).

In the C33A assay, 250,000 C33A cells were seeded into each of well of 6-well tissue culture plates and allowed to adhere overnight. 5 4µg each of pCMV-RB56, pCMV-E2F RB56, or pCMV-E2F plasmid were cotransfected (calcium phosphate method, MBS transfection kit, Stratagene) with 5 µg of indicated reporter construct E2-CAT or SVCAT) and 2.5 µg β-gal plasmid (pCMV-β, Clontech) per well into duplicate wells. Cells were harvested 72 hour after transfection and extracts were prepared.

In the 5637 assay, 250,000 5637 cells were seeded as described above. 1 µg each of RB or E2F-RB fusion plasmid, E2-CAT or SV-CAT reporter plasmid and pCMV-β-galactosidase were cotransfected using the lipofectin reagent (BRL, Bethesda, Maryland) according to the manufacturer's instructions.

CAT assays were performed using either 20 µL (C33A) or 50 µL (5637) of cell extract (Gorman et al. *Mol. Cell. Biol.* 2:1044 (1982)). TLCs were analyzed on a Phosphoimager SF (Molecular Dynamics). CAT activities were normalized for transfection efficiency according to β-galactosidase activities of each extract. β-galactosidase activities of extracts were assayed as described by Rosenthal et al. (*Meth. Enzym.* 152:704 (1987)).

Figure 10:
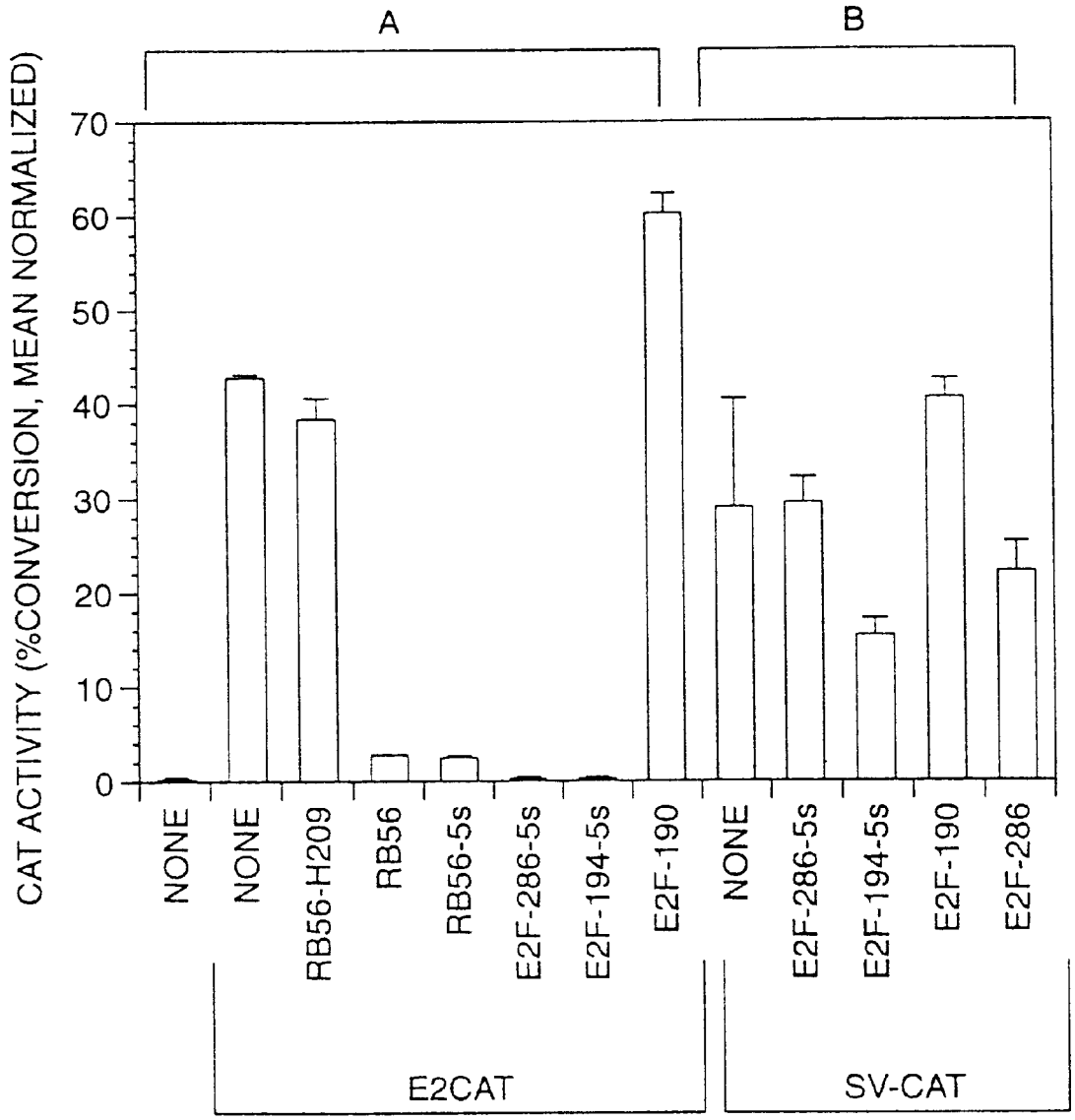
FIG. 10 is a diagram depicting transcriptional repression by E2F-RB fusion constructs.

The results of these studies were as follows. Transfection of the E2-CAT reporter alone or in the presence of the nonfunctional control RB56-H209 mutant yielded relatively high CAT activity. Cotransfection of wild-type RB56 or the variant RB56-5s resulted in a 10 to 12 fold repression of CAT activity, indicating that RB56 or RB56-5s are both capable of efficiently repressing E2F-dependent transcription. E2F194-RB5s and E2F286-RB5s repressed transcription approximately 50 fold. Transcriptional repression required both the RB56 and the E2F components of the fusion proteins, as expression of E2F194 and E2F286 did not mediate transcriptional repression. No repression of SV40-CAT transcription occurred with E2F-RB constructs, thus demonstrating the specificity of the transcriptional repression by E2FRB for the E2 promoter. These results are depicted diagrammatically in FIG. 10.

E. Cell Cycle Arrest

The ability of E2F-RB fusion polypeptides to cause G1 arrest in Saos-2 (RB−/−cells) (ATCC # HTB-85) and C33A cells was investigated. Previous studies have shown that RB-mediated E2 promoter repression and G1 arrest are linked in Saos-2 cells but dissociated in C33A (RBmut) cells (Xu, et al. *PNAS* 92:1357–1361 (1992)). Cells were washed in PBS and were fixed in 1 mL −20° C. 70% ethanol for 30 minutes. Cells were collected by centrifugation and resuspended in 0.5 mL 2% serum containing 10 µg/ml RNase A and incubated for 30 minutes at 37° C. 0.5 mL of PBS containing propidium iodide (100 µg/ml) was added to each sample, mixed and cells were filtered through a FACS tube capstrainer. FACS analysis was performed on a FACS-Scan (Becton-Dickenson) using doublet discrimination. 5,000–10,000 CD20+ events were analyzed. Percent of cells in $G_0/G_1$, S, and $G_2/M$ was determined using Modfit modeling software.

The results of this experiment were as follows. Both full length RB110 and the truncated version RB56, but not the control mutant RB-H209, caused $G_1$ arrest in Saos-2 cells (Table 1). Similarly, the RB56-5s, E2F-194-RB56-5s and E2F286-RB56-5s all were capable of arresting cells in $G_0/G_1$. Transfection of the DNA binding domain, E2F194, did not block S-phase entry in Saos-2 as previously described for rodent cells (Dobrowolski, et al. *Oncogene* 9:2605–2612 (1994)). In contrast, RB110, RB56, and E2F-RB fusion proteins were not capable of arresting C33A cell lines indicating that the transcriptional repression observed in these cells does not translate into $G_1$ arrest.

Figure 11:
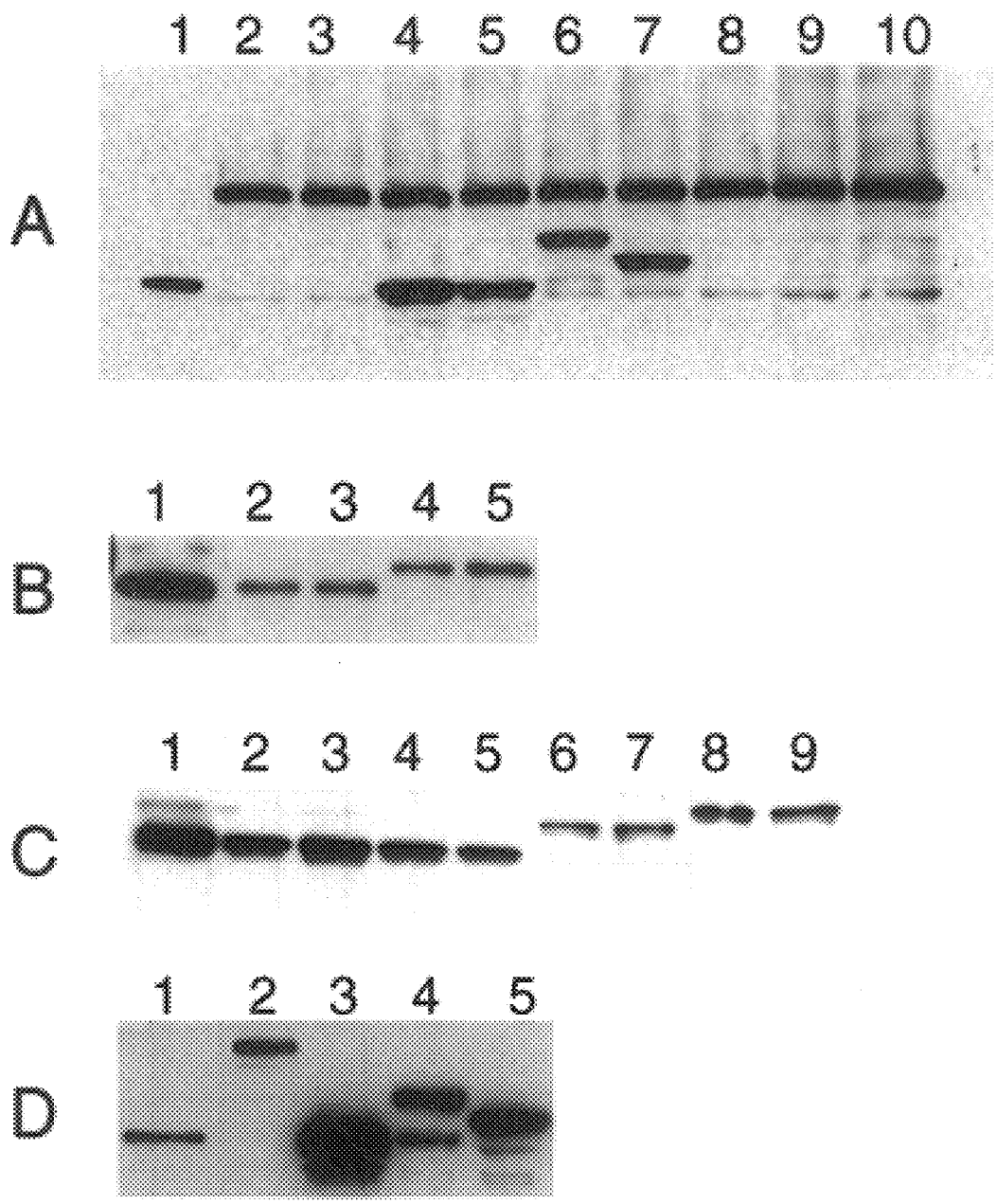
FIGS. 11 (A–D) depicts expression of E2F-RB fusion proteins in mammalian cell lines. Extracts were prepared from cells used in E2-CAT reporter assays or in FACS assays and analyzed with an anti-RB monoclonal antibody. In panel A, the results are shown from C33A cells transfected with (3) RB56-H209, (4) RB56 wild-type, (5) RB56-5s, (6) E2F286-5s, (7) E2F194-5s, (8) E2F194, (9) E2F286, (10) E2F437. Lane (1) is an RB56 protein standard. Lane (2) is a mock transfection. In panel B, results are shown for transfection of Saos-2 cells with (1) RB56, (2,3) E2F194-5s, and (4,5) E2F286-5s. In panel C, results are shown for transfection of 5637 cells with (2,3) RB56 wild-type, (4,5) RB56-5s; (6,7) E2F194-5s; (7,8) E2F286-5S. Lane (1) is an RB56 protein standard. In panel D, results are shown for NIH-3T3 transfected (3) RB56, (4) E2F286-5s, (5) E2F194-5s. Lane (1) is an RB56 standard; lane (2) is an RB110 standard.

The ability of the E2F-RB fusion proteins to arrest 5637 cells was also investigated (Table 2). RB56 and RB56-5s both efficiently arrested cells in $G_0/G_1$ (approximately 90% of cells in $G_0-G_1$), whereas E2F194-RB56-5s and E2F286-RB56-5s are slightly less efficient (about 80% of cells in $C_0/G_1$) at promoting $G_0/G_1$ arrest. Without being limited to any one theory, the less efficient arrest of both Saos-2 and 5637 cells by the E2F-RB fusion proteins appears due to the lower levels of steady-state protein produced in these cells (FIG. 11, panels b and c).

TABLE 1

Cell Cycle Regulation by RB and E2F-RB fusion proteins in RBneg cells

| | % Cells | | |
|---|---|---|---|
| | CD20+ | | |
| | $G_0/G_1$ | $G_2/M$ | S-phase |
| H209 | 52.1 | 27.1 | 20.8 |
| p56RB | 78.8 | 14.2 | 7.0 |
| p110RB | 70.9 | 14.3 | 14.8 |
| p56RB-5s | 84.8 | 13.2 | 2.0 |
| p56RB-p5 | 81.3 | 11.5 | 7.3 |
| E2F-194-5s | 77.8 | 14.9 | 7.3 |
| E2F-286-5s | 72.2 | 15.0 | 12.8 |
| E2F-194 | 49.9 | 28.0 | 22.1 |

TABLE 2

Growth Suppression of 5637 Bladder Cells by RB and E2F-RB fusion proteins

| | % Cells | | |
|---|---|---|---|
| 5637/CD20+ | $G_0/G_1$ | S | $G_2M$ |
| CD20 | 59.7 | 16.9 | 20.6 |
| RB56-C706F | 57.4 | 16.3 | 24.3 |
| RB56WT | 90.7 | 4.12 | 4.88 |
| RB56-5s | 89.91 | 3.51 | 6.1 |
| E2F1 94-5s | 80.1 | 1.31 | 0 |
| E2F-286-5s | 79.21 | 8.1 | 0 |

F. Activity of Fusion Proteins in Functional RB Background

Figure 12:
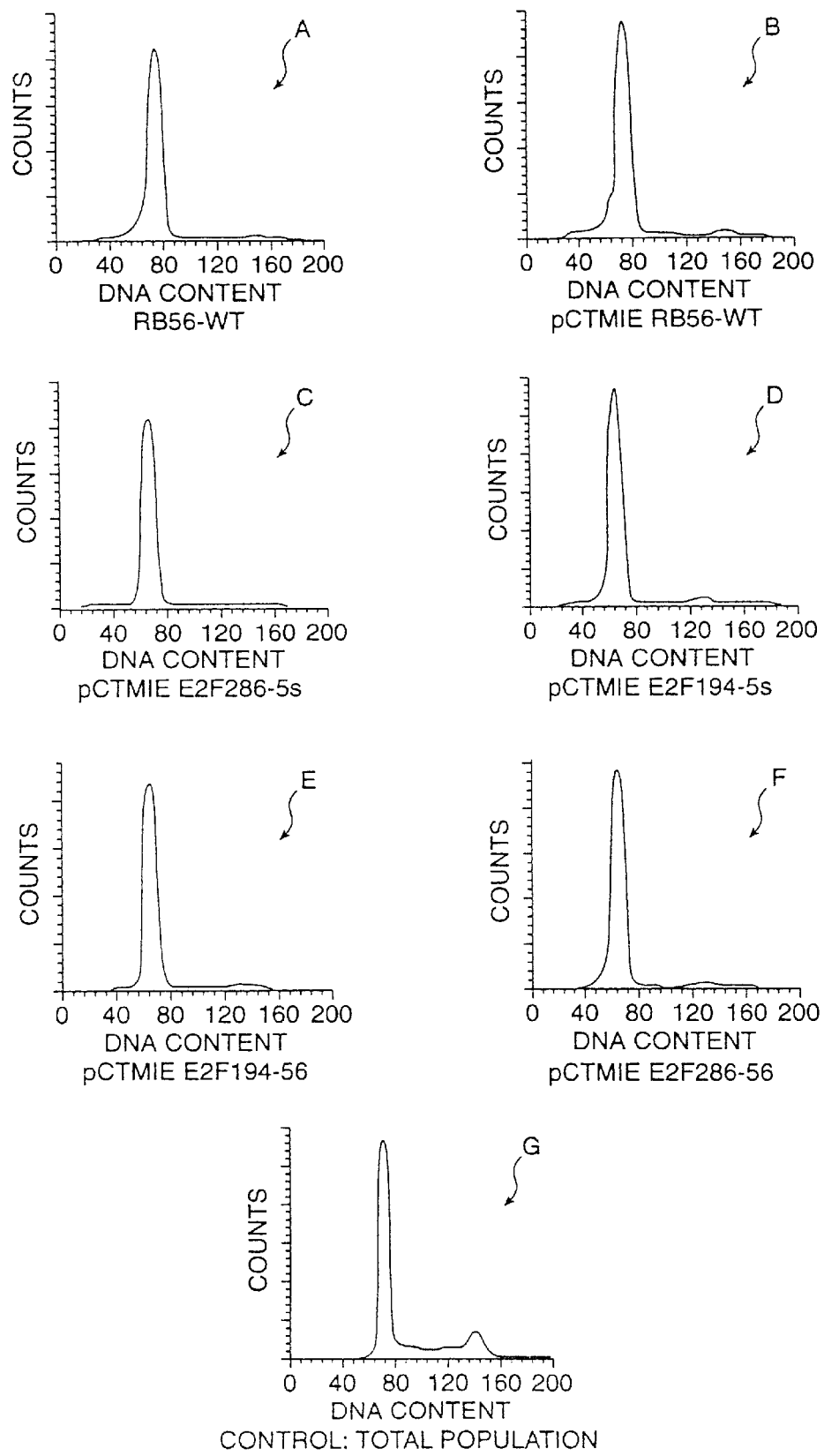
FIG. 12 depicts histogram analyses of flow cytometry of RB-expressing NIH-3T3 cells.

The activity of the E2F-RB fusion proteins in a cellular background containing functional RB was then determined. NIH-3T3 cells were transfected with RB56 or E2F-RB56 fusions and stained with anti-RB monoclonal antibody 3C8 (Wen et al. *J. Immuno. Meth.* 169:231–240 (1994)). FACS analysis was performed of the RB expressing cells. The results are shown in FIG. 12. The non-gated population (g) shows the characteristic cell cycle distribution for NIH-3T3 cells (60% GO, 28% S, 10% G2/M). In contrast, in cells transfected with RB56 (a,b) or E2F-RB fusion proteins (c-f), greater than 90% of the RB-expressing cells were arrested in $G_0/G_1$. These data demonstrate that the ability of RB and E2F-RB56 fusions to arrest cells in $G_0/G_1$ is not limited to RB negative tumor cells. The relative levels of protein expressed in transfected NIH-3T3 cells was also investigated. RB110 was not expressed efficiently in these cells.

Thus, these data demonstrate that E2F-RB fusion proteins are more efficient transcriptional repressors than either pRB or RB56 alone, and that RB can repress transcription by remaining bound to E2F rather than directly blocking the transactivation domain of E2F. These data support the use of E2F-RB fusions as RB agonists in both RB+ cells and in RB negative or RB mutant cells.

Example II

Tissue-Specific Expression of E2F-RB Fusions

A. Construction of Recombinant Adenovirus:

In this experiment, recombinant adenoviruses comprising an RB polypeptide under the control of a CMV or smooth muscle alpha actin promoter were generated.

The smooth muscle α-actin promoter (bases −670 through +5, Reddy et al. "Structure of the Human Smooth Muscle α-Actin Gene." J. Biol. Chem. 265:1683–1687 (1990), Nakano, et al. "Transcriptional Regulatory Elements In The 5' Upstream and First Intron Regions of The Human Smooth Muscle (aortic type) α-Actin-Encoding Gene." Gene 99:285–289 (1991) was isolated by PCR from a genomic library with 5' Xho I and Avr II and 3' Xba I, Cla I and Hind III restriction sites added for cloning purposes. The fragment was subcloned as an Xho 1, Hind III fragment into a plasmid for sequencing to verify base composition. A fusion construct 286–56 containing the DNA and heterodimerization domain of E2F-1 amino acids 95–286 linked to p56 (amino acids 379–928 of full length RB) was subcloned as an Xba I, Cla I fragment directly downstream of the smooth muscle α-actin promoter, and this expression cassette was digested out and cloned into the plasmid pAd/ITR/IX- as an Xba I to AvrII, and Cla I fragment to create the plasmid pASN286-56. This plasmid consisted of the adenovirus type 5 inverted terminal repeat (ITR), packaging signals and Ela enhancer, followed by the human smooth muscle α-actin promoter and 286-56 cassette, and then Ad 2 sequence 4021–10462 (which contains the Elb/protein IX poly A signal) in a pBR322 background. Recombinant adenovirus was produced by standard procedures. The plasmid pASN286-56 was linearized with Ngo MI and co-transfected into 293 cells with the large fragment of Cla I digested rAd34 which has deletions in both the E3 and E4 regions of adenovirus type 5. Ad34 was a serotype 5 derivative with a 1.9 KB deletion in early region 3 resulting from deletion of the Xba I restriction fragment extending from Ad5 coordinates 28593 to 30470 and a 1.4 KB deletion of early region 4 resulting from a Taq 1 fragment of E4 (coordinates 33055–35573) being replaced with a cDNA containing E4 ORF 6 and 6/7.

Recombinant adenovirus produced by homologous recombination was isolated and identified by restriction digest analysis and further purified by limiting dilution. Additional control recombinant adenoviruses are described elsewhere and include the control virus ACN (CMV promoter, Wills, et al. "Gene Therapy For Hepatocellular Carcinoma: Chemosensitivity Conferred By Adenovirus-Mediated Transfer of The HSV-1 Thymidine Kinase Gene." Cancer Gene Therapy 2:191–197 (1995)), and ACN56 (RB expressed under control of a CMV promoter).

ACN56 was prepared as follows. A plasmid containing p56 cDNA was constructed by replacing the p53 cDNA from the plasmid ACNP53 (Wills et al. Human Gene Therapy 5:1079–1088 (1994)) with a 1.7 KB Xba I- BamHI fragment isolated from plasmid pET 9a-Rb56 (Antelman et al. Oncogene 10:697–704 (1995)) which contains p56 cDNA. The resulting plasmid contained amino acids 381–928 of p56, the Ad5 inverted terminal repeat, viral packaging signals and Ela enhancer, followed by the human cytomegalovirus immediate early promoter (CMV) and Ad 2 tripartite leader cDNA to drive p56 expression. The p56 CDNA was followed by Ad 2 sequence 4021–10462 in a pBR322 background. This plasmid was linearized with EcoRI and cotransfected with the large fragment of bsp 106 digested DL327 (E3 deleted; Thimmappaya et al. Cell 31:543–551 (1982)) or h5ile4 (E4 deleted; Hemstrom et al. J. Virol. 62:3258–3264 (1988)). Recombinant viruses were further purified by limiting dilution.

B. Cellular Proliferation

In this experiment, cell lines were infected in culture with recombinant adenovirus RB constructs to ascertain the relative expression of the RB polypeptide and the effect on cell proliferation.

For H358 (ATCC # Crl 5807) and MDA-MB468 (ATCC # HTB 132, breast adenocarcinoma) cells, 5,000 cell/well were plated in normal growth media in a 96 well microtiter plate (Costar) and allowed to incubate overnight at 37° C., 7% $CO_2$. Viruses were serially diluted in growth media and used to infect cells at the indicated doses for 48 hours. At this point, $^3$H-thymidine was added (Amersham, 0.5 μCi/well) and the cells were incubated at 37° C. for another 3 hours prior to harvest. Both A7r5 (ATCC CRL1444, rat smooth muscle) and A10 (ATCC CRL 1476, rat smooth muscle) cells were seeded at 3,000 cells/well in either DME +0.5% FCS or DME +20% FCS respectively. Virus was serially diluted in the seeding media and used to infect the cells at the doses indicated in the Figures. The infection and labelling procedure were the same for A10 cells as with the H358 and MDA-MB468 cells except that 2 μCi/well of label was used. The A7r5 cells were not infected with virus until 48 hours after seeding. Forty eight hours after infection, the serum concentration was raised to 10% FCS and 2 μCi/well of 3H-thymidine was added and incubation continued for an additional 3 hours prior to harvest. All cells were harvested by aspirating media from the wells, trypsinization of the cells, and harvesting using a 96 well GF/C filter with a Packard Top count cell harvester. Results are plotted as the mean percentage (+/−SD) of media treated control proliferation versus dose of virus in FIGS. 13 and 14.

Figure 13A:
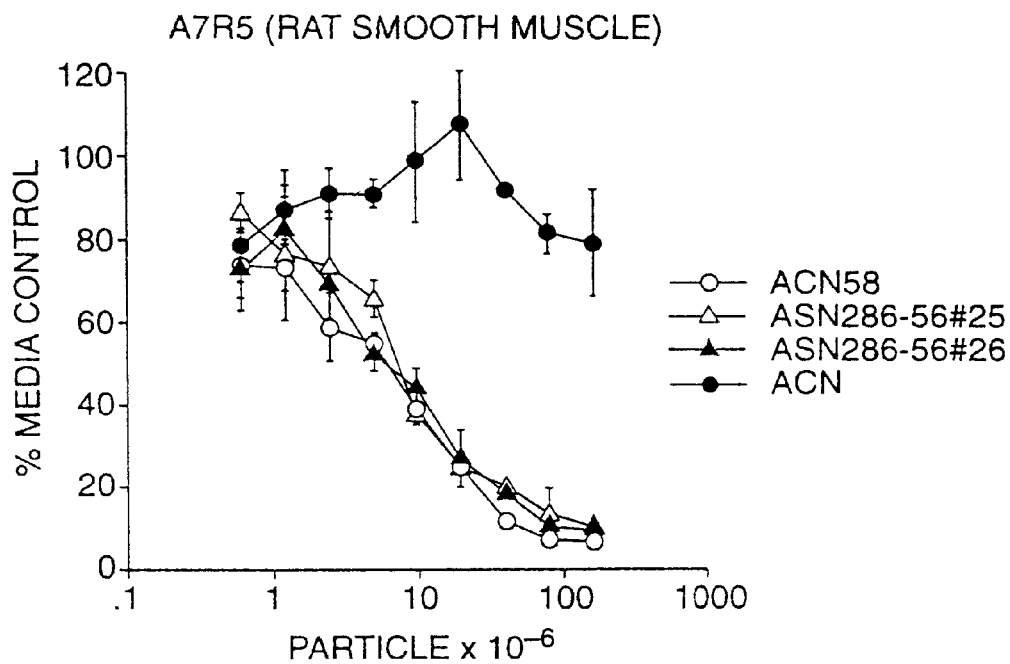
FIG. 13, panel A, depicts a comparison of the effects of a CMV-driven recombinant adenovirus (ACN56) with two isolates of a human smooth muscle alpha actin-driven E2F-p56 fusion construct consisting of amino acids 95 through 286 of E2F linked directly and in-frame to p56 (amino acids 379–928 of RB cDNA), vs. a control virus (ACN) in a $^3$H-thymidine uptake assay in the rat smooth muscle cell line A7R5. Panel (B) depicts the effects of the same constructs in the rat smooth muscle cell line A10.
Figure 13B:
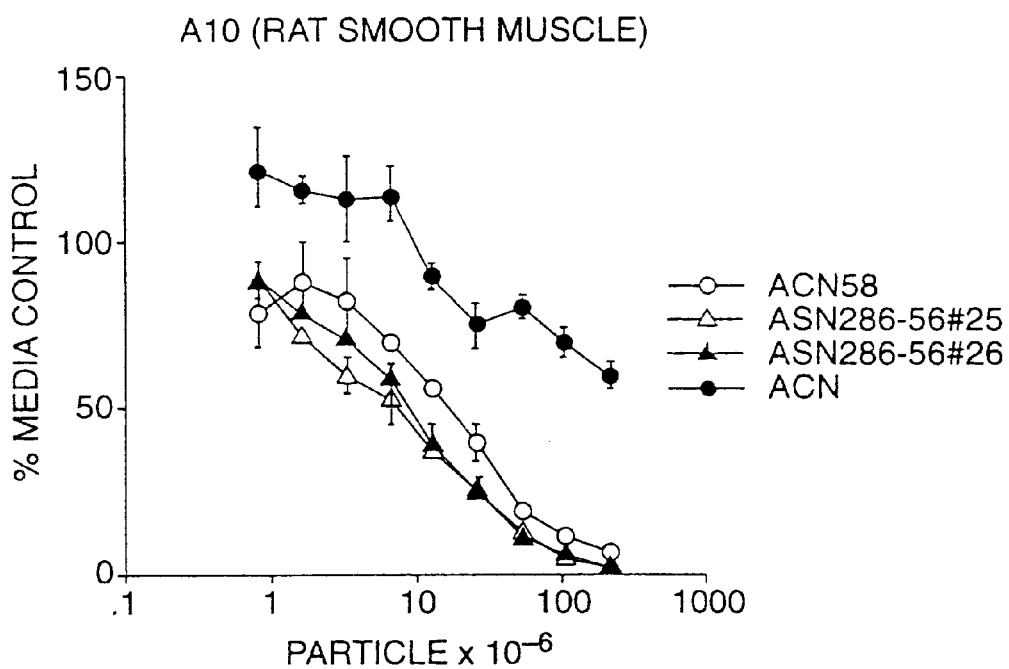
Figure 14A:
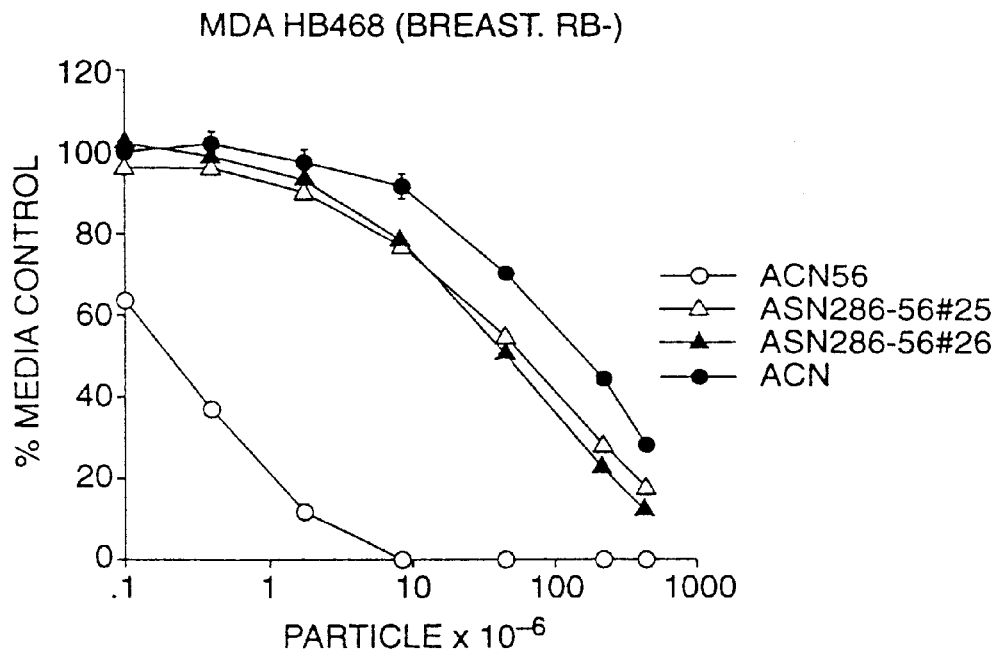
FIG. 14 depicts a comparison of the effects of the viruses described in FIG. 13 in non-muscle cells. Panel (A) depicts results in the breast carcinoma cell line MDA MB468. Panel (B) depicts results in the non-small cell lung cell carcinoma line H358.
Figure 14B:
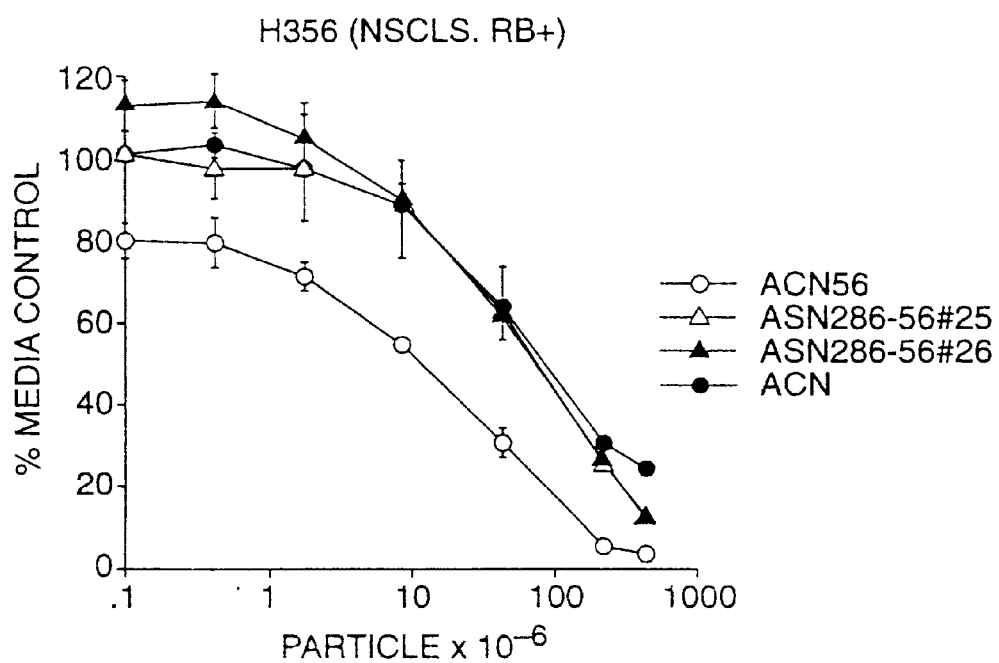

Thus, FIG. 13 depicts a comparison of the effects of adenovirus p56 constructs on muscle cells A10 and A7R5 cells. The CMV-driven p56 (ACN 56) virus inhibited A10 growth to approximately the same extent as the actin promoter-driven E2F-fusion constructs (ASN586-56 #25, 26). In FIG. 14, the effects of adenovirus constructs on inhibition of a breast cancer cell line, MDA Mβ468 and a non- small cell lung carcinoma cell line, H358, are depicted. In these experiments, actin promoter-driven E2F-p56 was ineffective, while the CMV promoter-driven p56 was effective in inhibiting growth of non-smooth muscle cells.

Figure 15:
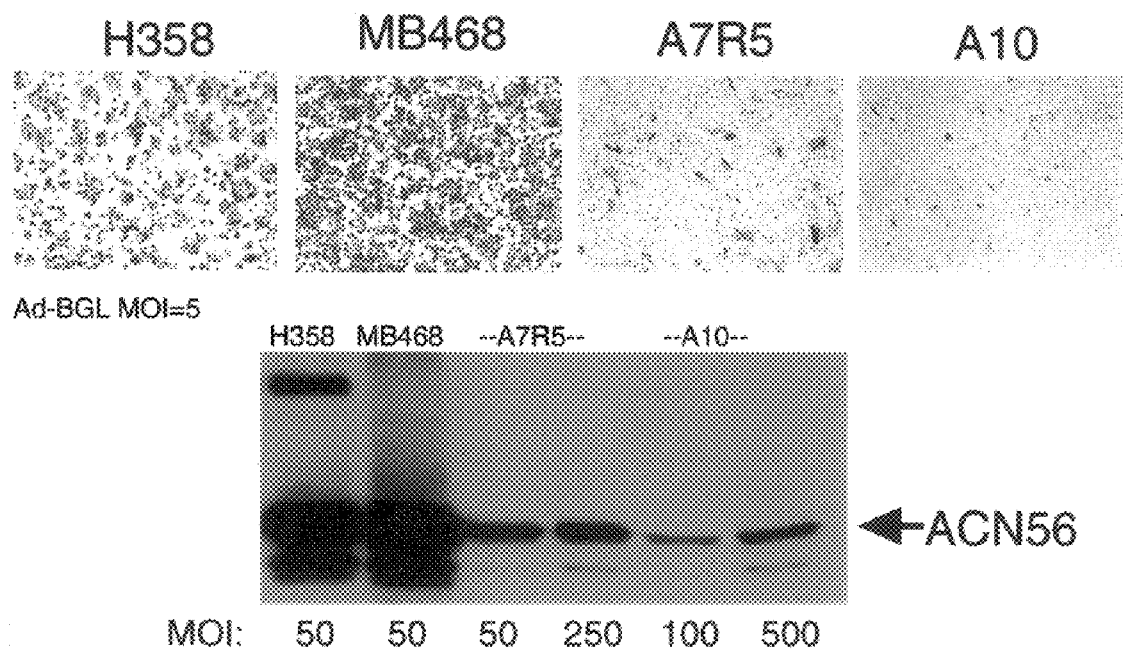
FIG. 15, top panel, depicts the relative infectivity by adenovirus of different cell lines as judged by the level of β-galactosidase (β-gal) staining following infection with equal amounts of a recombinant adenovirus expressing β-gal driven by a CMV promoter. H358 is non-small lung cell carcinoma cell line; MB468 is a breast carcinoma cell line; A7R5 and A10 are smooth muscle cell lines. The lower portion of the figure depicts the relative levels of p56 protein expressed in the same cells when infected with the recombinant adenovirus ACN56, in which the p56 cDNA is driven by the non-tissue specific CMV promoter.
Figure 16:
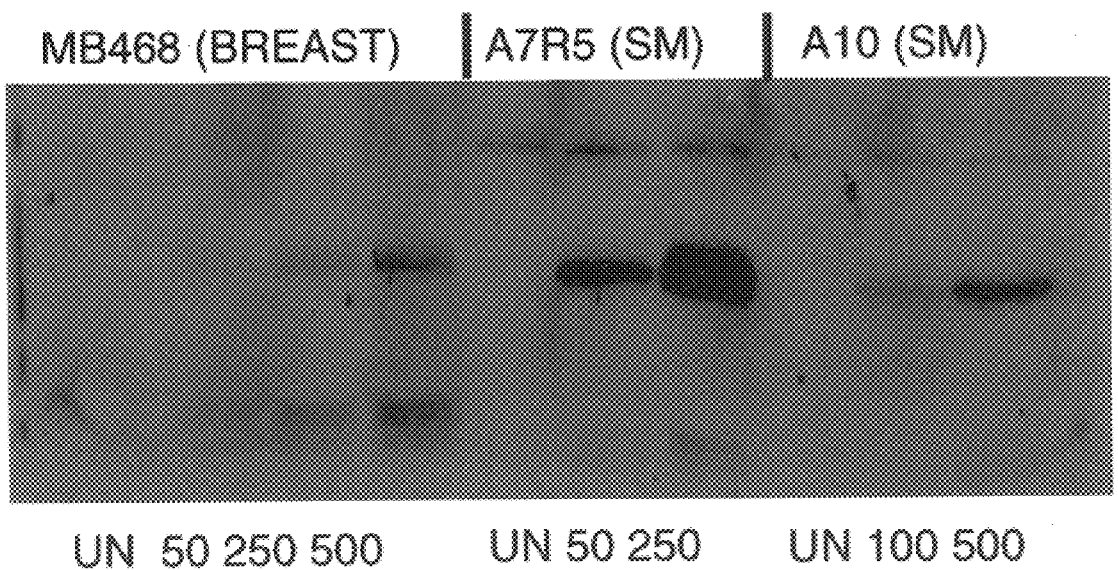
FIG. 16 depicts relative protein levels in cells infected with the smooth muscle alpha actin promoter-driven E2F-p56 fusion construct (ASN286-56). UN denoted uninfected; 50, 100, 250, and 500 refer to multiplicities of infection (MOI).

To determine whether the non-smooth muscle cells were more infectable with adenovirus than the smooth muscle cell lines used, the four cells lines, H358, MB468, A7R5, and A10 were infected at an MOI of 5 with an adenovirus expressing β-galactosidase (ACβGL; Wills, et al. Human Gene Therapy 5:1079–1088 (1994)) and degree of β-gal staining was examined. As shown in FIG. 15 (top), the non-smooth muscle cell lines were significantly more infectable than the smooth muscle cell lines. In a further test, cells were infected at higher multiplicities of infection (50, 100, 250, 500) with ACN56 and the amount of p56 present in the infected cells detected by autoradiography. As can be seen in FIG. 15 (bottom), the non-muscle cell lines had significantly more p56 present, since as a result of their greater infectivity, infected cells have a greater viral load and thus more copies of the p56 template driven by the non-tissue specific CMV promoter.

Figure 19:
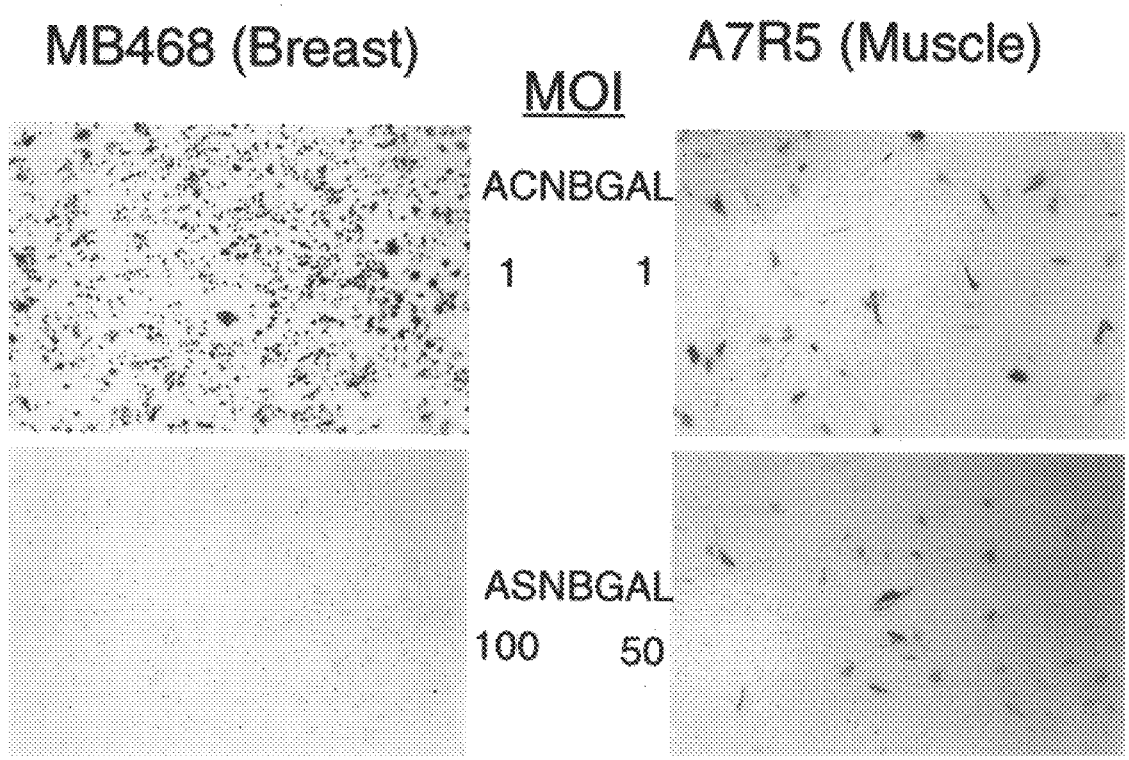
FIG. 19 depicts tissue-specificity of the smooth muscle alpha actin promoter, as demonstrated by its selective ability to express the β-gal transgene in muscle cells but not non-muscle cells. The panels on the left compare β-gal expression in the breast cell carcinoma line MB468 infected with either an MOI=1 with a CMV-driven β-gal (ACNBGAL) vs an MOI=100 with the smooth muscle promoter construct (ASNBGAL). The panels on the right show β-gal expression of the rat smooth muscle cell line A7R5 infected with either an MOI=1 of ACNBGAL or an MOI=50 of ASNBGAL. Expression from ASNBGAL is seen in the muscle cell line, but is absent in the non-muscle cell line, despite the higher degree of infectivity of the cells.

In a further experiment, the specificity of the actin smooth muscle promoter for smooth muscle tissue was ascertained. In this experiment, β-gal expression levels in cells infected with β-gal constructs driven with different promoters were measured. As can be seen in FIG. 19, despite the lower infectivity of the smooth muscle cells, expression was only evident in these cells using the smooth muscle alpha actin promoter.

Figure 21A:
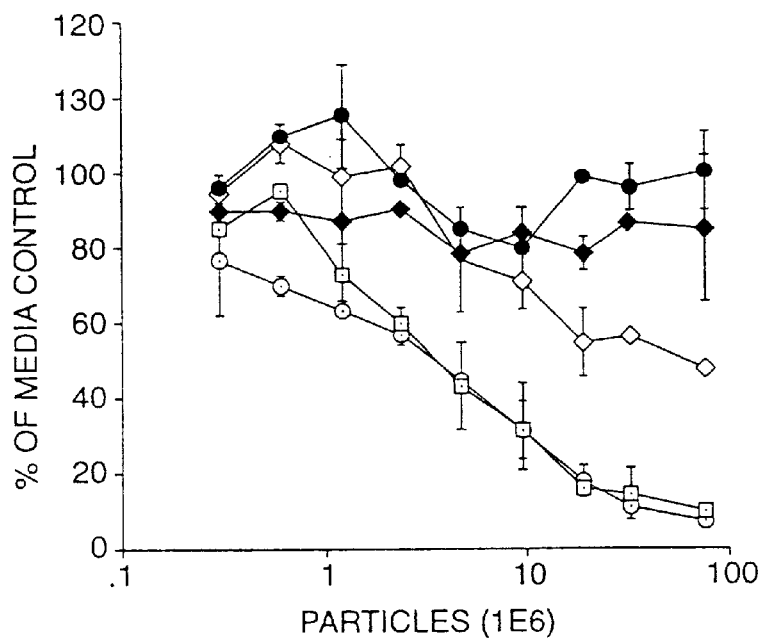
FIG. 21 depicts a comparison of the effects of a CMV-driven p56 recombinant adenovirus (ACN56E4) vs a human smooth muscle alpha-actin promoter-driven E2F-p56 fusion construct (ASN286-56) vs control adenoviral constructs containing either the CMV or smooth muscle alpha-actin promoters without a downstream transgene (ACNE3 or ASBE3-2 isolates shown, respectively). Assays were $^3$H-thymidine uptake either in a smooth muscle cell line (A7R5) or a non-muscle cell line (MDA-MB468, breast carcinoma). Results demonstrated muscle tissue specificity using the smooth muscle alpha-actin promoter and specific inhibition by both the p56 and E2F-p56 transgenes relative to their respective controls.
Figure 21B:
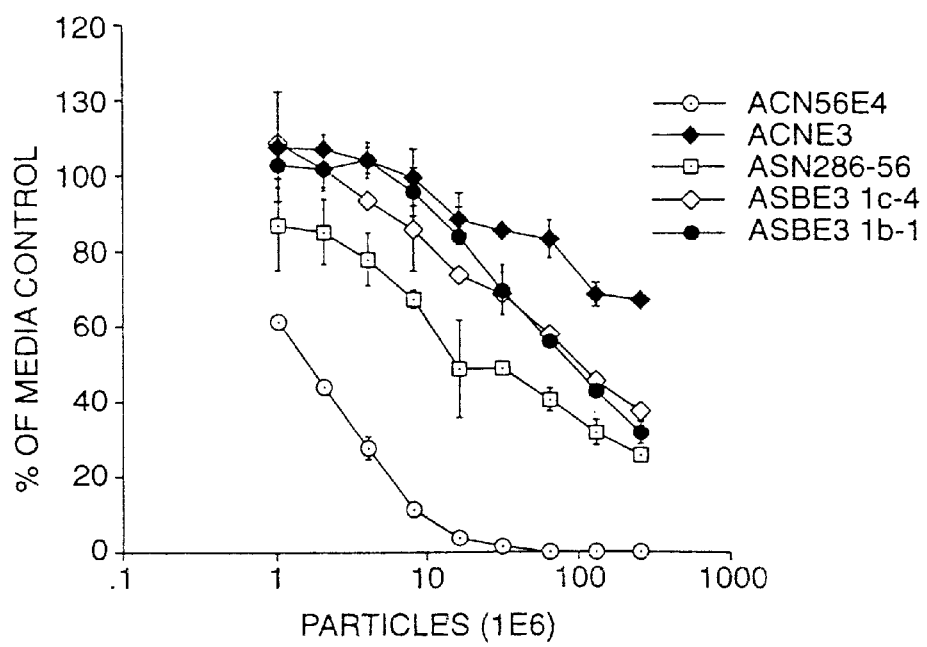

FIG. 21 depicts a comparison of the effects of a CMV driven p56 recombinant adenovirus (ACN56E4) vs a human smooth muscle alpha-actin promoter driven E2F-p56 fusion construct (ASN286-56) vs control adenoviral construct containing either the CMV or smooth muscle alpha-actin promoters without a downstream transgene (ACNE3 or ASBE3-2 isolates shown, respectively). Assays were 3H-thymidine uptake either in a smooth muscle cell line (A7R5) or a non-muscle cell line (MDA-MB468, breast carcinoma). Results demonstrated muscle tissue specificity using the smooth muscle alpha-actin promoter and specific inhibition of both the p56 and E2F-p56 transgenes relative to their respective controls.

C. Inhibition of Restenosis

The model of balloon injury was based on that described by Clowes, et al. (Clowes, *Lab. Invest.* 49:327–333 (1983)). Male Sprague-Dawley rats weighing 400–500 g were anesthetized with an intraperitoneal injection of sodium pentobarbital (45 mg/kg. Abbot Laboratories, North Chicago, Ill.). The bifurcation of the left common carotid artery was exposed through a midline incision and the left common, internal, and external carotid arteries were temporarily ligated. A 2F embolectomy catheter (Baxter Edwards Healthcare Corp., Irvine, Calif.) was introduced into the external carotid and advanced to the distal ligation of the common carotid. The balloon was inflated with saline and drawn towards the arteriotomy site 3 times to produce a distending, deendothelializing injury. The catheter was then withdrawn. Adenovirus ($1\times10^9$ pfu of Ad-RB (ACNRb) or Ad-p56 (ACN56) in a volume of 10 μl diluted to 100 μl with 15% (wt/vol) Poloxamer 407 (BASF, Parsippany, N.J.) or Ad-β-Gal ($1\times10^9$ pfu, diluted as above) was injected via a canula, inserted just proximal to the carotid bifurcation into a temporarily isolated segment of the artery. The adenovirus solution was incubated for 20 minutes after which the viral infusion was withdrawn and the cannula removed. The proximal external carotid artery was then ligated and blood flow was restored to the common carotid artery by release of the ligatures. The experimental protocol was approved by the Institutional Animal Care and Use Committee and complied with the "Guide for the Care and Use of Laboratory Animals." (NIH Publication No. 86-23, revised 1985).

Rats were sacrificed at 14 days following treatment with an intraperitoneal injection of pentobarbital (100 mg/kg.). The initially balloon injured segment of the left common carotid artery, from the proximal edge of the omohyoid muscle to the carotid bifurcation, was perfused with saline and dissected free of the surrounding tissue. The tissue was fixed in 100% methanol until imbedded in paraffin. Several 4-μm sections were cut from each tissue specimen. One section from each specimen was stained with hematoxylin and eosin and another with Richardson's combination elastic-trichrome stain conventional light microscopic analysis.

Histological images of cross sections of hematoxylin and eosin or elastic-trichrome stained arterial sections were projected onto a digitizing board (Summagraphics) and the intimal, medial and luminal areas were measured by quantitative morphometric analysis using a computerized sketching program (MACMEASURE, version 1.9, National Institute of Mental Health).

Results were expressed as the mean ± S.E.M. Differences between groups were analyzed using an unpaired two-tailed Student's t test. Statistical significance was assumed when the probability of a null effect was <0.05.

Figure 17:
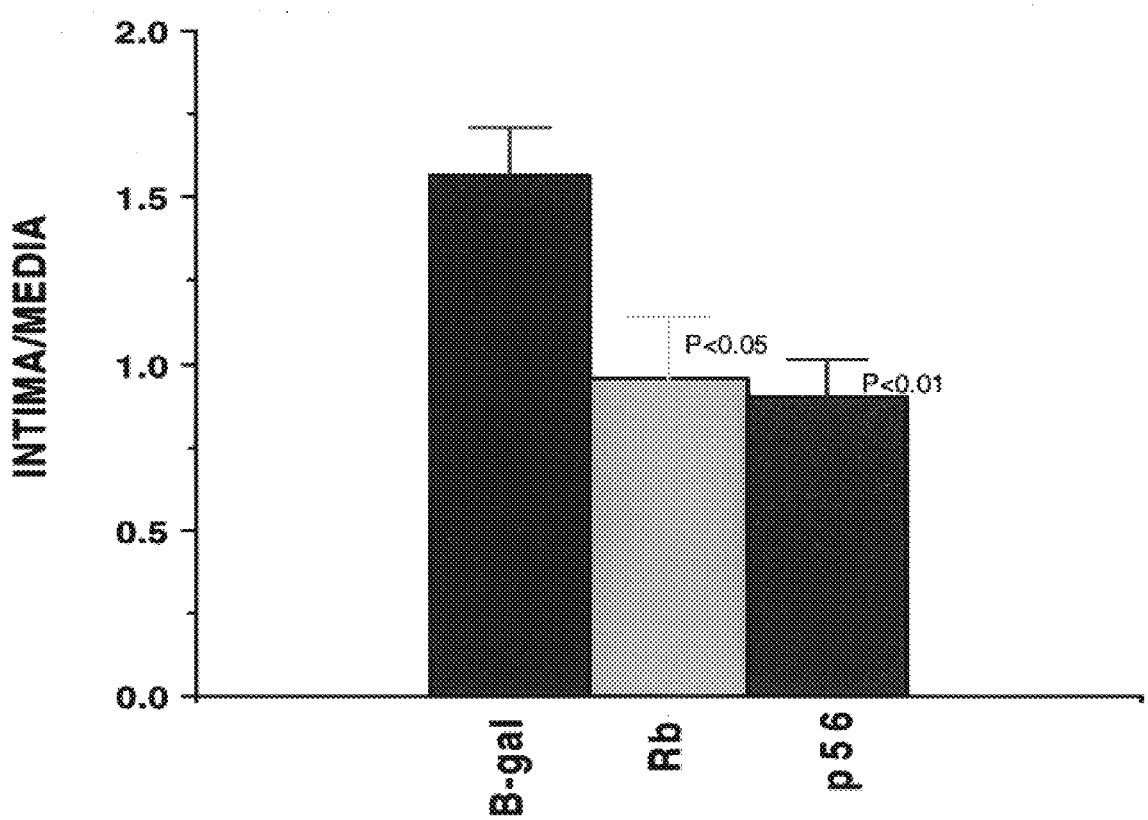
FIG. 17 is a bar graph depicting the ratio of intima to media area (as a measurement of the inhibition of neointima formation) from cross-sections (n=9) of rat carotid arteries which were injured and treated with recombinant adenoviruses expressing either β-gal, RB (ACNRB) or p56 (ACN56), all under the control of the CMV promoter.
Figure 18:
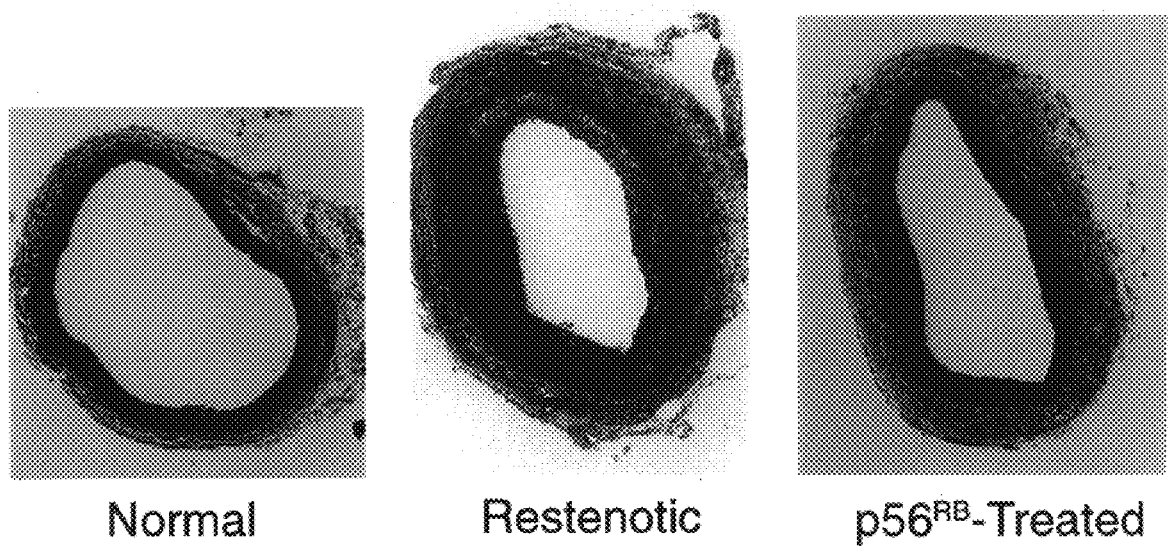
FIG. 18 is a series of three photographs depicting restenosis in a rat angioplasty model. The panel on the left depicts data from a normal animal; the central panel depicts data from an animal injured and then treated with a β-gal expressing recombinant virus; the panel on the right depicts data from an animal injured and then treated with a recombinant adenovirus expressing p56 (ACN56).

Results are shown in FIGS. 17 and 18. In FIG. 17, the relative inhibition of neointima formation is depicted graphically, demonstrating the ability of p56 and RB to inhibit neointima formation. FIG. 18 provides photographic evidence of the dramatic reduction of neointima in the presence of p56.

Figure 20:
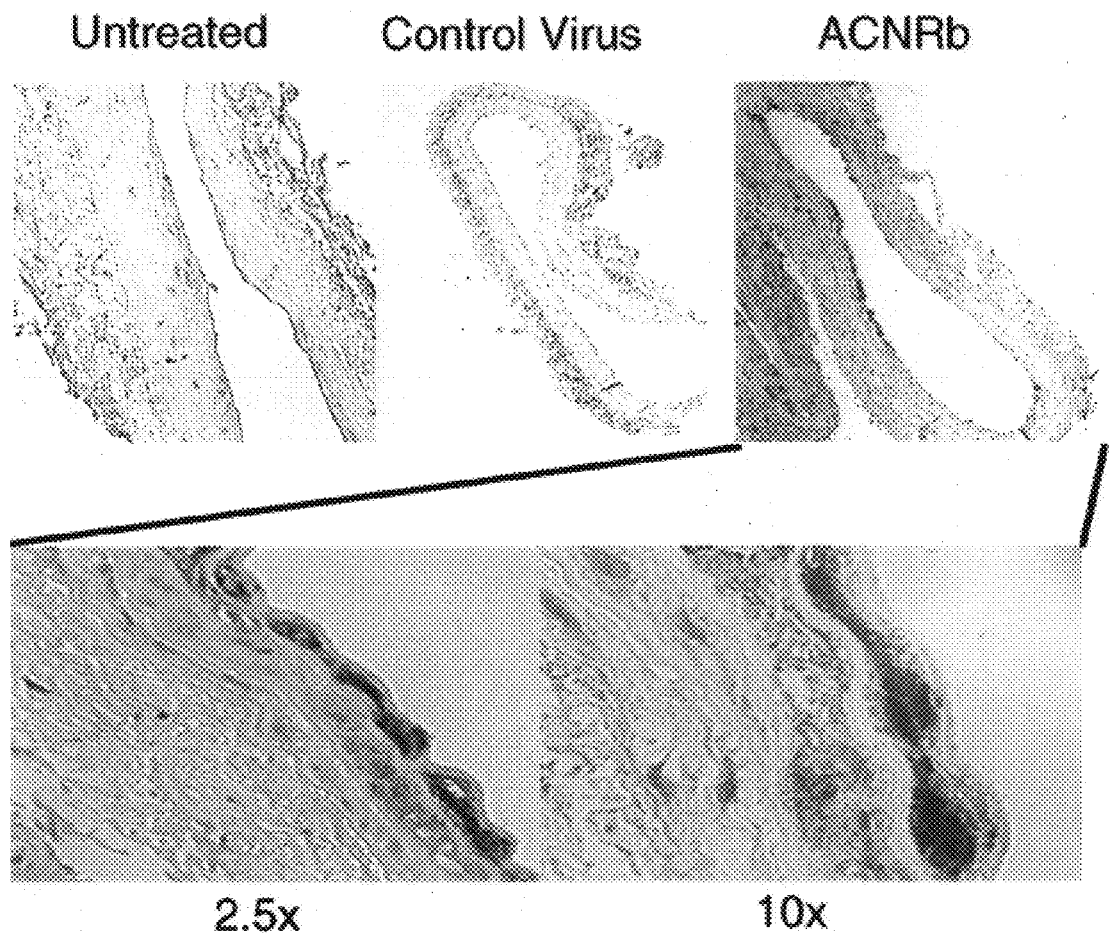
FIG. 20 depicts the ability of recombinant adenovirus expressing RB to transduce rat carotid arteries. recombinant adenovirus-treated arteries ($1 \times 10^9$ pfu) were harvested two days following balloon injury and infection. Cross sections were fixed and an RB specific antibody was used to detect the presence of RB protein in the tissue. The control virus used was ACN. RB protein staining was evident in the ACNRB treated sample, especially at higher magnifications.

Adenovirus-treated carotid arteries were harvested from rats at 2 days following balloon injury and infections. Tissue was fixed in phosphate-buffered formalin until embedded in paraffin. Tissue was cut into 4 μm cross-sections and dewaxed through xylene and graded alcohols. Endogenous peroxidase was quenched with 1% hydrogen peroxide for 30 minutes. Antigen retrieval was performed in 10 mM sodium citrate buffer, pH 6.0 at 95° C. for 10 minutes. A monoclonal anti-RB antibody (AB-5, Oncogene Sciences, Uniondale, New York) was applied 10 μg/ml in PBS in a humid chamber at 4° C. for 24 hours. Secondary antibody was applied from the Unitect Mouse Immunohistochemistry Kit (Oncogene Sciences, Uniondale, New York) according to the manufacturer's instructions. The antibody complexes were visualized using 3,3'-diaminobenzidene (DAB, Vector Laboratories, Burlingame, Calif.). Slides were thin counterstained with hematoxylin and mounted. The results are depicted in FIG. 20.

All references cited herein are hereby incorporated by reference in their entirety for all purposes.

What is claimed is:

1. A nucleic acid encoding a fusion polypeptide, the polypeptide comprising a fusion of a DNA binding domain of an E2F transcription factor and a functional growth suppression domain of a retinoblastoma(RB) polypeptide, wherein the fusion polypeptide lacks a functional cyclin A-kinase binding domain of the E2F transcription factor.

2. The nucleic acid of claim 1, wherein the nucleic acid is inserted in an adenovirus vector.

3. A expression vector comprising DNA encoding a fusion polypeptide, the polypeptide comprising a fusion of a DNA binding domain of an E2F transcription factor and a functional growth suppression domain of a retinoblastoma(RB) polypeptide, wherein the fusion polypeptide lacks a functional cyclin A-kinase binding domain of the E2F transcription factor.

4. The vector of claim 3, comprising a tissue-specific promoter operatively linked to DNA encoding the fusion.

5. The vector of claim 4, wherein the tissue specific promoter is a smooth muscle actin promoter.

6. The expression vector of claim 3, wherein the vector is a viral vector.

7. The expression vector of claim 6, wherein the vector is an adenovirus vector.

8. The vector of claim 7, wherein adenovirus vector is replication deficient.

9. The vector of claim 3, wherein the expression vector is a plasmid.

10. The vector of claim 5, wherein the actin promoter is an alpha actin promoter.

11. A nucleic acid sequence encoding a fusion polypeptide, the polypeptide comprising a fusion of about amino acids 95–194 of E2F (SEQ ID NO:1) and amino acids about 379–928 of RB (SEQ ID NO:4).

12. The nucleic acid of claim 11, further comprising vector.

13. The nucleic acid sequence of claim 12, wherein the vector is a viral vector.

14. The nucleic acid sequence of claim 13, wherein the viral vector is an adenoviral vector.

15. The nucleic acid sequence of claim 14, wherein the adenoviral vector is replication deficient.

16. The nucleic acid sequence of claim 11, wherein the nucleic acid sequence further comprises a tissue-specific promoter, wherein the fusion polypeptide is expressed under control of the tissue-specific promoter.

17. The nucleic acid sequence of claim 16, wherein the tissue-specific promoter is a smooth muscle actin promoter.

18. The nucleic acid sequence of claim 17, wherein the smooth muscle promoter is an alpha actin promoter.

* * * * *

SEQUENCE LISTING (1) GENERAL INFORMATION:

(iii) NUMBER OF SEQUENCES: 46

(2) INFORMATION FOR SEQ ID NO:1:

(i) SEQUENCE CHARACTERISTICS:
      (A) LENGTH: 437 amino acids
      (B) TYPE: amino acid
      (C) STRANDEDNESS: Not Relevant
      (D) TOPOLOGY: Not Relevant (ii) MOLECULE TYPE: peptide (xi) SEQUENCE DESCRIPTION: SEQ ID NO:1:

```
Met Ala Leu Ala Gly Ala Pro Ala Gly Gly Pro Cys Ala Pro Ala Leu
1               5                   10                  15

Glu Ala Leu Leu Gly Ala Gly Ala Leu Arg Leu Leu Asp Ser Ser Gln
                20                  25                  30

Ile Val Ile Ile Ser Ala Ala Gln Asp Ala Ser Ala Pro Pro Ala Pro
            35                  40                  45

Thr Gly Pro Ala Ala Pro Ala Ala Gly Pro Cys Asp Pro Asp Leu Leu
        50                  55                  60

Leu Phe Ala Thr Pro Gln Ala Pro Arg Pro Thr Pro Ser Ala Pro Arg
65                  70                  75                  80

Pro Ala Leu Gly Arg Pro Pro Val Lys Arg Arg Leu Asp Leu Glu Thr
                85                  90                  95

Asp His Gln Tyr Leu Ala Glu Ser Ser Gly Pro Ala Arg Gly Arg Gly
            100                 105                 110

Arg His Pro Gly Lys Gly Val Lys Ser Pro Gly Glu Lys Ser Arg Tyr
        115                 120                 125

Glu Thr Ser Leu Asn Leu Thr Thr Lys Arg Phe Leu Glu Leu Leu Ser
    130                 135                 140

His Ser Ala Asp Gly Val Val Asp Leu Asn Trp Ala Ala Glu Val Leu
145                 150                 155                 160

Lys Val Gln Lys Arg Arg Ile Tyr Asp Ile Thr Asn Val Leu Glu Gly
                165                 170                 175

Ile Gln Leu Ile Ala Lys Lys Ser Lys Asn His Ile Gln Trp Leu Gly
            180                 185                 190

Ser His Thr Thr Val Gly Val Gly Gly Arg Leu Glu Gly Leu Thr Gln
        195                 200                 205

Asp Leu Arg Gln Leu Gln Glu Ser Glu Gln Gln Leu Asp His Leu Met
    210                 215                 220

Asn Ile Cys Thr Thr Gln Leu Arg Leu Leu Ser Glu Asp Thr Asp Ser
225                 230                 235                 240

Gln Arg Leu Ala Tyr Val Thr Cys Gln Asp Leu Arg Ser Ile Ala Asp
                245                 250                 255

Pro Ala Glu Gln Met Val Met Val Ile Lys Ala Pro Pro Glu Thr Gln
            260                 265                 270

Leu Gln Ala Val Asp Ser Ser Glu Asn Phe Gln Ile Ser Leu Lys Ser
        275                 280                 285

Lys Gln Gly Pro Ile Asp Val Phe Leu Cys Pro Glu Glu Thr Val Gly
    290                 295                 300

Gly Ile Ser Pro Gly Lys Thr Pro Ser Gln Glu Val Thr Ser Glu Glu
305                 310                 315                 320

Glu Asn Arg Ala Thr Asp Ser Ala Thr Ile Val Ser Pro Pro Pro Ser
                325                 330                 335

Ser Pro Pro Ser Ser Leu Thr Thr Asp Pro Ser Gln Ser Leu Leu Ser
            340                 345                 350

Leu Glu Gln Glu Pro Leu Leu Ser Arg Met Gly Ser Leu Arg Ala Pro
        355                 360                 365

Val Asp Glu Asp Arg Leu Ser Pro Leu Val Ala Ala Asp Ser Leu Leu
    370                 375                 380

Glu His Val Arg Glu Asp Phe Ser Gly Leu Leu Pro Glu Glu Phe Ile
385                 390                 395                 400

Ser Leu Ser Pro Pro His Glu Ala Leu Asp Tyr His Phe Gly Leu Glu
```

```
                    405                 410                 415
Glu Gly Glu Gly Ile Arg Asp Leu Phe Asp Cys Asp Phe Gly Asp Leu
            420                 425                 430

Thr Pro Leu Asp Phe
        435

(2) INFORMATION FOR SEQ ID NO:2:

(i) SEQUENCE CHARACTERISTICS:
        (A) LENGTH: 2517 base pairs
        (B) TYPE: nucleic acid
        (C) STRANDEDNESS: single
        (D) TOPOLOGY: linear (xi) SEQUENCE DESCRIPTION: SEQ ID NO:2:

GGAATTCCGT GGCCGGGACT TTGCAGGCAG CGGCGGCCGG GGGCGGAGCG GGATCGAGCC      60

CTCGCCGAGG CCTGCCGCCA TGGGCCCGCG CCGCCGCCGC CGCCTGTCAC CCGGGCCGCG     120

CGGGCCGTGA GCGTCATGGC CTTGGCCGGG GCCCCTGCGG GCGGCCCATG CGCGCCGGCG     180

CTGGAGGCCC TGCTCGGGGC CGGCGCGCTG CGGCTGCTCG ACTCCTCGCA GATCGTCATC     240

ATCTCCGCCG CGCAGGACGC CAGCGCCCCG CCGGCTCCCA CCGGCCCCGC GGCGCCCGCC     300

GCCGGCCCCT GCGACCCTGA CCTGCTGCTC TTCGCCACAC CGCAGGCGCC CCGGCCCACA     360

CCCAGTGCGC CGCGGCCCGC GCTCGGCCGC CCGCCGGTGA AGCGGAGGCT GGACCTGGAA     420

ACTGACCATC AGTACCTGGC CGAGAGCAGT GGGCCAGCTC GGGCAGAGG CCGCCATCCA      480

GGAAAAGGTG TGAAATCCCC GGGGGAGAAG TCACGCTATG AGACCTCACT GAATCTGACC     540

ACCAAGCGCT TCCTGGAGCT GCTGAGCCAC TCGGCTGACG GTGTCGTCGA CCTGAACTGG     600

GCTGCCGAGG TGCTGAAGGT GCAGAAGCGG CGCATCTATG ACATCACCAA CGTCCTTGAG     660

GGCATCCAGC TCATTGCCAA GAAGTCCAAG AACCACATCC AGTGGCTGGG CAGCCACACC     720

ACAGTGGGCG TCGGCGGACG GCTTGAGGGG TTGACCCAGG ACCTCCGACA GCTGCAGGAG     780

AGCGAGCAGC AGCTGGACCA CCTGATGAAT ATCTGTACTA CGCAGCTGCG CCTGCTCTCC     840

GAGGACACTG ACAGCCAGCG CCTGGCCTAC GTGACGTGTC AGGACCTTCG TAGCATTGCA     900

GACCCTGCAG AGCAGATGGT TATGGTGATC AAAGCCCCTC CTGAGACCCA GCTCCAAGCC     960

GTGGACTCTT CGGAGAACTT TCAGATCTCC CTTAAGAGCA AACAAGGCCC GATCGATGTT    1020

TTCCTGTGCC CTGAGGAGAC CGTAGGTGGG ATCAGCCCTG GAAGACCCC ATCCAGGAG      1080

GTCACTTCTG AGGAGGAGAA CAGGGCCACT GACTCTGCCA CCATAGTGTC ACCACCACCA    1140

TCATCTCCCC CCTCATCCCT CACCACAGAT CCCAGCCAGT CTCTACTCAG CCTGGAGCAA    1200

GAACCGCTGT TGTCCCGGAT GGGCAGCCTG CGGGCTCCCG TGGACGAGGA CCGCCTGTCC    1260

CCGCTGGTGG CGGCCGACTC GCTCCTGGAG CATGTGCGGG AGGACTTCTC CGGCCTCCTC    1320

CCTGAGGAGT TCATCAGCCT TTCCCCACCC CACGAGGCCC TCGACTACCA CTTCGGCCTC    1380

GAGGAGGGCG AGGGCATCAG AGACCTCTTC GACTGTGACT TTGGGGACCT CACCCCCCTG    1440

GATTTCTGAC AGGGCTTGGA GGGACCAGGG TTTCCAGAGT AGCTCACCTT GTCTCTGCAG    1500

CCCTGGAGCC CCCTGTCCCT GGCCGTCCTC CCAGCCTGTT TGGAAACATT TAATTTATAC    1560

CCCTCTCCTC TGTCTCCAGA AGCTTCTAGC TCTGGGGTCT GGCTACCGCT AGGAGGCTGA    1620

GCAAGCCAGG AAGGGAAGGA GTCTGTGTGG TGTGTATGTG CATGCAGCCT ACACCCACAC    1680

GTGTGTACCG GGGGTGAATG TGTGTGAGCA TGTGTGTGTG CATGTACCGG GGAATGAAGG    1740

TGAACATACA CCTCTGTGTG TGCACTGCAG ACACGCCCCA GTGTGTCCAC ATGTGTGTGC    1800
```

-continued

```
ATGAGTCCAT CTCTGCGCGT GGGGGGGCTC TAACTGCACT TCGGCCCTT TTGCTCGTGG      1860

GGTCCCACAA GGCCCAGGGC AGTGCCTGCT CCCAGAATCT GGTGCTCTGA CCAGGCCAGG     1920

TGGGGAGGCT TTGGCTGGCT GGGCGTGTAG GACGGTGAGA GCACTTCTGT CTTAAAGGTT     1980

TTTTCTGATT GAAGCTTTAA TGGAGCGTTA TTTATTTATC GAGGCCTCTT TGGTGAGCCT     2040

GGGGAATCAG CAAAAGGGGA GGAGGGGTGT GGGGTTGATA CCCCAACTCC CTCTACCCTT     2100

GAGCAAGGGC AGGGGTCCCT GAGCTGTTCT TCTGCCCCAT ACTGAAGGAA CTGAGGCCTG     2160

GGTGATTTAT TTATTGGGAA AGTGAGGGAG GGAGACAGAC TGACTGACAG CCATGGGTGG     2220

TCAGATGGTG GGGTGGGCCC TCTCCAGGGG GCCAGTTCAG GGCCCAGCTG CCCCCCAGGA    2280

TGGATATGAG ATGGGAGAGG TGAGTGGGGG ACCTTCACTG ATGTGGGCAG GAGGGGTGGT    2340

GAAGGCCTCC CCCAGCCCAG ACCCTGTGGT CCCTCCTGCA GTGTCTGAAG CGCCTGCCTC    2400

CCCACTGCTC TGCCCCACCC TCCAATCTGC ACTTTGATTT GCTTCCTAAC AGCTCTGTTC    2460

CCTCCTGCTT TGGTTTTAAT AAATATTTTG ATGACGTTAA AAAAAGGAAT TCGATAT       2517
```

(2) INFORMATION FOR SEQ ID NO:3:

(i) SEQUENCE CHARACTERISTICS:
        (A) LENGTH: 2994 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

```
TTCCGGTTTT TCTCAGGGGA CGTTGAAATT ATTTTTGTAA CGGGAGTCGG GAGAGGACGG       60

GGCGTGCCCC GCGTGCGCGC GCGTCGTCCT CCCCGGCGCT CCTCCACAGC TCGCTGGCTC      120

CCGCCGCGGA AAGGCGTCAT GCCGCCCAAA ACCCCCGAA AAACGGCCGC CACCGCCGCC       180

GCTGCCGCCG CGGAACCCCC GGCACCGCCG CCGCCGCCCC CTCCTGAGGA GGACCCAGAG      240

CAGGACAGCG GCCCGGAGGA CCTGCCTCTC GTCAGGCTTG AGTTTGAAGA AACAGAAGAA      300

CCTGATTTTA CTGCATTATG TCAGAAATTA AAGATACCAG ATCATGTCAG AGAGAGAGCT      360

TGGTTAACTT GGGAGAAAGT TTCATCTGTG GATGGAGTAT TGGGAGGTTA TATTCAAAAG      420

AAAAAGGAAC TGTGGGGAAT CTGTATCTTT ATTGCAGCAG TTGACCTAGA TGAGATGTCG      480

TTCACTTTTA CTGAGCTACA GAAAAACATA GAAATCAGTG TCCATAAATT CTTTAACTTA      540

CTAAAAGAAA TTGATACCAG TACCAAAGTT GATAATGCTA TGTCAAGACT GTTGAAGAAG      600

TATGATGTAT TGTTTGCACT CTTCAGCAAA TTGGAAAGGA CATGTGAACT TATATATTTG      660

ACACAACCCA GCAGTTCGAT ATCTACTGAA ATAAATTCTG CATTGGTGCT AAAAGTTTCT      720

TGGATCACAT TTTTATTAGC TAAAGGGGAA GTATTACAAA TGGAAGATGA TCTGGTGATT      780

TCATTTCAGT TAATGCTATG TGTCCTTGAC TATTTTATTA AACTCTCACC TCCCATGTTG      840

CTCAAAGAAC CATATAAAAC AGCTGTTATA CCCATTAATG GTTCACCTCG AACACCCAGG      900

CGAGGTCAGA ACAGGAGTGC ACGGATAGCA AAACAACTAG AAAATGATAC AAGAATTATT      960

GAAGTTCTCT GTAAAGAACA TGAATGTAAT ATAGATGAGG TGAAAAATGT TTATTTCAAA     1020

AATTTTATAC CTTTTATGAA TTCTCTTGGA CTTGTAACAT CTAATGGACT TCCAGAGGTT     1080

GAAAATCTTT CTAAACGATA CGAAGAAATT TATCTTAAAA ATAAAGATCT AGATGCAAGA     1140

TTATTTTTGG ATCATGATAA AACTCTTCAG ACTGATTCTA TAGACAGTTT TGAAACACAG     1200

AGAACACCAC GAAAAAGTAA CCTTGATGAA GAGGTGAATG TAATTCCTCC ACACACTCCA     1260
```

-continued

```
GTTAGGACTG TTATGAACAC TATCCAACAA TTAATGATGA TTTTAAATTC AGCAAGTGAT    1320

CAACCTTCAG AAAATCTGAT TTCCTATTTT AACAACTGCA CAGTGAATCC AAAAGAAAGT    1380

ATACTGAAAA GAGTGAAGGA TATAGGATAC ATCTTTAAAG AGAAATTTGC TAAAGCTGTG    1440

GGACAGGGTT GTGTCGAAAT TGGATCACAG CGATACAAAC TTGGAGTTCG CTTGTATTAC    1500

CGAGTAATGG AATCCATGCT TAAATCAGAA GAAGAACGAT TATCCATTCA AAATTTTAGC    1560

AAACTTCTGA ATGACAACAT TTTTCATATG TCTTTATTGG CGTGCGCTCT TGAGGTTGTA    1620

ATGGCCACAT ATAGCAGAAG TACATCTCAG AATCTTGATT CTGGAACAGA TTTGTCTTTC    1680

CCATGGATTC TGAATGTGCT TAATTTAAAA GCCTTTGATT TTTACAAAGT GATCGAAAGT    1740

TTTATCAAAG CAGAAGGCAA CTTGACAAGA GAAATGATAA ACATTTAGA ACGATGTGAA     1800

CATCGAATCA TGGAATCCCT TGCATGGCTC TCAGATTCAC CTTTATTTGA TCTTATTAAA    1860

CAATCAAAGG ACCGAGAAGG ACCAACTGAT CACCTTGAAT CTGCTTGTCC TCTTAATCTT    1920

CCTCTCCAGA ATAATCACAC TGCAGCAGAT ATGTATCTTT CTCCTGTAAG ATCTCCAAAG    1980

AAAAAGGTT CAACTACGCG TGTAAATTCT ACTGCAAATG CAGAGACACA AGCAACCTCA     2040

GCCTTCCAGA CCCAGAAGCC ATTGAAATCT ACCTCTCTTT CACTGTTTTA TAAAAAGTG     2100

TATCGGCTAG CCTATCTCCG GCTAAATACA CTTTGTGAAC GCCTTCTGTC TGAGCACCCA    2160

GAATTAGAAC ATATCATCTG GACCCTTTTC CAGCACACCC TGCAGAATGA GTATGAACTC    2220

ATGAGAGACA GGCATTTGGA CCAAATTATG ATGTGTTCCA TGTATGGCAT ATGCAAAGTG    2280

AAGAATATAG ACCTTAAATT CAAAATCATT GTAACAGCAT ACAAGGATCT TCCTCATGCT    2340

GTTCAGGAGA CATTCAAACG TGTTTTGATC AAAGAAGAGG AGTATGATTC TATTATAGTA    2400

TTCTATAACT CGGTCTTCAT GCAGAGACTG AAAACAAATA TTTTGCAGTA TGCTTCCACC    2460

AGGCCCCCTA CCTTGTCACC AATACCTCAC ATTCCTCGAA GCCCTTACAA GTTTCCTAGT    2520

TCACCCTTAC GGATTCCTGG AGGGAACATC TATATTTCAC CCCTGAAGAG TCCATATAAA    2580

ATTTCAGAAG GTCTGCCAAC ACCAACAAAA ATGACTCCAA GATCAAGAAT CTTAGTATCA    2640

ATTGGTGAAT CATTCGGGAC TTCTGAGAAG TTCCAGAAAA TAAATCAGAT GGTATGTAAC    2700

AGCGACCGTG TGCTCAAAAG AAGTGCTGAA GGAAGCAACC CTCCTAAACC ACTGAAAAAA    2760

CTACGCTTTG ATATTGAAGG ATCAGATGAA GCAGATGGAA GTAAACATCT CCCAGGAGAG    2820

TCCAAATTTC AGCAGAAACT GGCAGAAATG ACTTCTACTC GAACACGAAT GCAAAAGCAG    2880

AAAATGAATG ATAGCATGGA TACCTCAAAC AAGGAAGAGA AATGAGGATC TCAGGACCTT    2940

GGTGGACACT GTGTACACCT CTGGATTCAT TGTCTCTCAC AGATGTGACT GTAT          2994
```

(2) INFORMATION FOR SEQ ID NO:4:

(i) SEQUENCE CHARACTERISTICS:
        (A) LENGTH: 928 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:4:

```
Met Pro Pro Lys Thr Pro Arg Lys Thr Ala Ala Thr Ala Ala Ala Ala
1               5                   10                  15

Ala Ala Glu Pro Pro Ala Pro Pro Pro Pro Pro Pro Glu Glu Asp
            20                  25                  30

Pro Glu Gln Asp Ser Gly Pro Glu Asp Leu Pro Leu Val Arg Leu Glu
        35                  40                  45
```

```
Phe Glu Glu Thr Glu Pro Asp Phe Thr Ala Leu Cys Gln Lys Leu
 50                  55                  60

Lys Ile Pro Asp His Val Arg Glu Arg Ala Trp Leu Thr Trp Glu Lys
 65                  70                  75                  80

Val Ser Ser Val Asp Gly Val Leu Gly Gly Tyr Ile Gln Lys Lys
                 85                  90                  95

Glu Leu Trp Gly Ile Cys Ile Phe Ile Ala Ala Val Asp Leu Asp Glu
            100                 105                 110

Met Ser Phe Thr Phe Thr Glu Leu Gln Lys Asn Ile Glu Ile Ser Val
        115                 120                 125

His Lys Phe Phe Asn Leu Leu Lys Glu Ile Asp Thr Ser Thr Lys Val
    130                 135                 140

Asp Asn Ala Met Ser Arg Leu Leu Lys Lys Tyr Asp Val Leu Phe Ala
145                 150                 155                 160

Leu Phe Ser Lys Leu Glu Arg Thr Cys Glu Leu Ile Tyr Leu Thr Gln
                165                 170                 175

Pro Ser Ser Ser Ile Ser Thr Glu Ile Asn Ser Ala Leu Val Leu Lys
            180                 185                 190

Val Ser Trp Ile Thr Phe Leu Leu Ala Lys Gly Glu Val Leu Gln Met
        195                 200                 205

Glu Asp Asp Leu Val Ile Ser Phe Gln Leu Met Leu Cys Val Leu Asp
210                 215                 220

Tyr Phe Ile Lys Leu Ser Pro Pro Met Leu Leu Lys Glu Pro Tyr Lys
225                 230                 235                 240

Thr Ala Val Ile Pro Ile Asn Gly Ser Pro Arg Thr Pro Arg Arg Gly
                245                 250                 255

Gln Asn Arg Ser Ala Arg Ile Ala Lys Gln Leu Glu Asn Asp Thr Arg
            260                 265                 270

Ile Ile Glu Val Leu Cys Lys Glu His Glu Cys Asn Ile Asp Glu Val
        275                 280                 285

Lys Asn Val Tyr Phe Lys Asn Phe Ile Pro Phe Met Asn Ser Leu Gly
    290                 295                 300

Leu Val Thr Ser Asn Gly Leu Pro Glu Val Glu Asn Leu Ser Lys Arg
305                 310                 315                 320

Tyr Glu Glu Ile Tyr Leu Lys Asn Lys Asp Leu Asp Ala Arg Leu Phe
                325                 330                 335

Leu Asp His Asp Lys Thr Leu Gln Thr Asp Ser Ile Asp Ser Phe Glu
            340                 345                 350

Thr Gln Arg Thr Pro Arg Lys Ser Asn Leu Asp Glu Glu Val Asn Val
        355                 360                 365

Ile Pro Pro His Thr Pro Val Arg Thr Val Met Asn Thr Ile Gln Gln
370                 375                 380

Leu Met Met Ile Leu Asn Ser Ala Ser Asp Gln Pro Ser Glu Asn Leu
385                 390                 395                 400

Ile Ser Tyr Phe Asn Asn Cys Thr Val Asn Pro Lys Glu Ser Ile Leu
                405                 410                 415

Lys Arg Val Lys Asp Ile Gly Tyr Ile Phe Lys Glu Lys Phe Ala Lys
            420                 425                 430

Ala Val Gly Gln Gly Cys Val Glu Ile Gly Ser Gln Arg Tyr Lys Leu
        435                 440                 445

Gly Val Arg Leu Tyr Tyr Arg Val Met Glu Ser Met Leu Lys Ser Glu
    450                 455                 460
```

-continued

```
Glu Glu Arg Leu Ser Ile Gln Asn Phe Ser Lys Leu Leu Asn Asp Asn
465                 470                 475                 480

Ile Phe His Met Ser Leu Leu Ala Cys Ala Leu Glu Val Val Met Ala
                485                 490                 495

Thr Tyr Ser Arg Ser Thr Ser Gln Asn Leu Asp Ser Gly Thr Asp Leu
            500                 505                 510

Ser Phe Pro Trp Ile Leu Asn Val Leu Asn Leu Lys Ala Phe Asp Phe
        515                 520                 525

Tyr Lys Val Ile Glu Ser Phe Ile Lys Ala Glu Gly Asn Leu Thr Arg
    530                 535                 540

Glu Met Ile Lys His Leu Glu Arg Cys Glu His Arg Ile Met Glu Ser
545                 550                 555                 560

Leu Ala Trp Leu Ser Asp Ser Pro Leu Phe Asp Leu Ile Lys Gln Ser
                565                 570                 575

Lys Asp Arg Glu Gly Pro Thr Asp His Leu Glu Ser Ala Cys Pro Leu
            580                 585                 590

Asn Leu Pro Leu Gln Asn Asn His Thr Ala Ala Asp Met Tyr Leu Ser
        595                 600                 605

Pro Val Arg Ser Pro Lys Lys Lys Gly Ser Thr Thr Arg Val Asn Ser
    610                 615                 620

Thr Ala Asn Ala Glu Thr Gln Ala Thr Ser Ala Phe Gln Thr Gln Lys
625                 630                 635                 640

Pro Leu Lys Ser Thr Ser Leu Ser Leu Phe Tyr Lys Lys Val Tyr Arg
                645                 650                 655

Leu Ala Tyr Leu Arg Leu Asn Thr Leu Cys Glu Arg Leu Leu Ser Glu
            660                 665                 670

His Pro Glu Leu Glu His Ile Ile Trp Thr Leu Phe Gln His Thr Leu
        675                 680                 685

Gln Asn Glu Tyr Glu Leu Met Arg Asp Arg His Leu Asp Gln Ile Met
    690                 695                 700

Met Cys Ser Met Tyr Gly Ile Cys Lys Val Lys Asn Ile Asp Leu Lys
705                 710                 715                 720

Phe Lys Ile Ile Val Thr Ala Tyr Lys Asp Leu Pro His Ala Val Gln
                725                 730                 735

Glu Thr Phe Lys Arg Val Leu Ile Lys Glu Glu Tyr Asp Ser Ile
            740                 745                 750

Ile Val Phe Tyr Asn Ser Val Phe Met Gln Arg Leu Lys Thr Asn Ile
        755                 760                 765

Leu Gln Tyr Ala Ser Thr Arg Pro Pro Thr Leu Ser Pro Ile Pro His
    770                 775                 780

Ile Pro Arg Ser Pro Tyr Lys Phe Pro Ser Ser Pro Leu Arg Ile Pro
785                 790                 795                 800

Gly Gly Asn Ile Tyr Ile Ser Pro Leu Lys Ser Pro Tyr Lys Ile Ser
                805                 810                 815

Glu Gly Leu Pro Thr Pro Thr Lys Met Thr Pro Arg Ser Arg Ile Leu
            820                 825                 830

Val Ser Ile Gly Glu Ser Phe Gly Thr Ser Glu Lys Phe Gln Lys Ile
        835                 840                 845

Asn Gln Met Val Cys Asn Ser Asp Arg Val Leu Lys Arg Ser Ala Glu
    850                 855                 860

Gly Ser Asn Pro Pro Lys Pro Leu Lys Lys Leu Arg Phe Asp Ile Glu
865                 870                 875                 880

Gly Ser Asp Glu Ala Asp Gly Ser Lys His Leu Pro Gly Glu Ser Lys
```

Phe Gln Gln Lys Leu Ala Glu Met Thr Ser Thr Arg Thr Arg Met Gln
            885                 890                 895
                            900                 905                 910

Lys Gln Lys Met Asn Asp Ser Met Asp Thr Ser Asn Lys Glu Glu Lys
            915                 920                 925

(2) INFORMATION FOR SEQ ID NO:5:

(i) SEQUENCE CHARACTERISTICS:
        (A) LENGTH: 3853 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 209..250

(ix) FEATURE:
        (A) NAME/KEY: CDS
        (B) LOCATION: 254..289

(ix) FEATURE:
        (A) NAME/KEY: CDS
        (B) LOCATION: 293..505

(ix) FEATURE:
        (A) NAME/KEY: CDS
        (B) LOCATION: 509..514

(ix) FEATURE:
        (A) NAME/KEY: CDS
        (B) LOCATION: 518..520

(ix) FEATURE:
        (A) NAME/KEY: CDS
        (B) LOCATION: 524..658

(ix) FEATURE:
        (A) NAME/KEY: CDS
        (B) LOCATION: 662..691

(ix) FEATURE:
        (A) NAME/KEY: CDS
        (B) LOCATION: 695..748

(ix) FEATURE:
        (A) NAME/KEY: CDS
        (B) LOCATION: 752..781

(ix) FEATURE:
        (A) NAME/KEY: CDS
        (B) LOCATION: 785..829

(ix) FEATURE:
        (A) NAME/KEY: CDS
        (B) LOCATION: 1132..1134

(ix) FEATURE:
        (A) NAME/KEY: CDS
        (B) LOCATION: 1138..1149

(ix) FEATURE:
        (A) NAME/KEY: CDS
        (B) LOCATION: 833..862

(xi) SEQUENCE DESCRIPTION: SEQ ID NO:5:

GACGGATCGG GAGATCTCCC GATCCCCTAT GGTCGACTCT CAGTACAATC TGCTCTGATG        60

CCGCATAGTT AAGCCAGTAT CTGCTCCCTG CTTGTGTGTT GGAGGTCGCT GAGTAGTGCG       120

CGAGCAAAAT TTAAGCTACA ACAAGGCAAG GCTTGACCGA CAATTGCATG AAGAATCTGC       180

```
TTAGGGTTAG GCGTTTTGCG CTGCTTCG CGA TGT ACG GGC CAG ATA TAC GCG         232
                              Arg Cys Thr Gly Gln Ile Tyr Ala
                               1               5

TTG ACA TTG ATT ATT GAC TAG TTA TTA ATA GTA ATC AAT TAC GGG GTC        280
Leu Thr Leu Ile Ile Asp     Leu Leu Ile Val Ile Asn Tyr Gly Val
        10                   1               5

ATT AGT TCA TAG CCC ATA TAT GGA GTT CCG CGT TAC ATA ACT TAC GGT        328
Ile Ser Ser     Pro Ile Tyr Gly Val Pro Arg Tyr Ile Thr Tyr Gly
 10              1               5                       10

AAA TGG CCC GCC TGG CTG ACC GCC CAA CGA CCC CCG CCC ATT GAC GTC        376
Lys Trp Pro Ala Trp Leu Thr Ala Gln Arg Pro Pro Pro Ile Asp Val
         15              20              25

AAT AAT GAC GTA TGT TCC CAT AGT AAC GCC AAT AGG GAC TTT CCA TTG        424
Asn Asn Asp Val Cys Ser His Ser Asn Ala Asn Arg Asp Phe Pro Leu
 30              35              40

ACG TCA ATG GGT GGA CTA TTT ACG GTA AAC TGC CCA CTT GGC AGT ACA        472
Thr Ser Met Gly Gly Leu Phe Thr Val Asn Cys Pro Leu Gly Ser Thr
 45              50              55                          60

TCA AGT GTA TCA TAT GCC AAG TAC GCC CCC TAT TGA CGT CAA                514
Ser Ser Val Ser Tyr Ala Lys Tyr Ala Pro Tyr     Arg Gln
             65              70                   1

TGA CGG TAA ATG GCC CGC CTG GCA TTA TGC CCA GTA CAT GAC CTT ATG        562
    Arg     Met Ala Arg Leu Ala Leu Cys Pro Val His Asp Leu Met
     1       1               5                       10

GGA CTT TCC TAC TTG GCA GTA CAT CTA CGT ATT AGT CAT CGC TAT TAC        610
Gly Leu Ser Tyr Leu Ala Val His Leu Arg Ile Ser His Arg Tyr Tyr
         15              20              25

CAT GGT GAT GCG GTT TTG GCA GTA CAT CAA TGG GCG TGG ATA GCG GTT        658
His Gly Asp Ala Val Leu Ala Val His Gln Trp Ala Trp Ile Ala Val
 30              35              40                          45

TGA CTC ACG GGG ATT TCC AAG TCT CCA CCC CAT TGA CGT CAA TGG GAG        706
    Leu Thr Gly Ile Ser Lys Ser Pro Pro His     Arg Gln Trp Glu
     1               5                  10       1

TTT GTT TTG GCA CCA AAA TCA ACG GGA CTT TCC AAA ATG TCG               748
Phe Val Leu Ala Pro Lys Ser Thr Gly Leu Ser Lys Met Ser
 5              10              15

TAA CAA CTC CGC CCC ATT GAC GCA AAT GGG CGG TAG CGC TGT ACG GTG        796
    Gln Leu Arg Pro Ile Asp Ala Asn Gly Arg     Arg Cys Thr Val
     1               5              10           1

GGA GGT CTA TAT AAG CAG AGC TCT CTG GCT AAC TAG AGA ACC CAC TGC        844
Gly Gly Leu Tyr Lys Gln Ser Ser Leu Ala Asn     Arg Thr His Cys
 5              10              15               1

TTA CTG GCT TAT CGA AAT TAATACGACT CACTATAGGG AGACCCAAGC               892
Leu Leu Ala Tyr Arg Asn
 5              10

TTCGCGCGGG TACCACTCTC TTCCGCATCG CTGTCTGCGA GGGCCAGCTG TTGGGCTCGC      952

GGTTGAGGAC AAACTCTTCG CGGTCTTTCC AGTACTCTTG GATCGGAAAC CCGTCGGCCT     1012

CCGAACGGTA CTCCGCCACC GAGGGACCTG AGCGAGTCCG CATCGACCGG ATCGGAAAAC     1072

CTCTCGAGGC GGCCGCTGCA GTCTAGACGA ATTCGCGTAC GATATCGATG GCCCTATT      1131

CTA TAG TGT CAC CTA AAT GCTAGAGCTC GCTGATCAGC CTCGACTGTG              1179
Leu     Cys His Leu Asn
 1       1

CCTTCTAGTT GCCAGCCATC TGTTGTTTGC CCCTCCCCCG TGCCTTCCTT GACCCTGGAA     1239

GGTGCCACTC CCACTGTCCT TTCCTAATAA AATGAGGAAA TTGCATCGCA TTGTCTGAGT     1299

AGGTGTCATT CTATTCTGGG GGGTGGGGTG GGCAGGACA GCAAGGGGGA GGATTGGGAA      1359

GACAATAGCC GAAATGACCG ACCAAGCGAC GCCCAACCTG CCATCACGAG ATTTCGATTC     1419
```

```
CACCGCCGCC TTCTATGAAA GGTTGGGCTT CGGAATCGTT TTCCGGGACG CCGGCTGGAT    1479

GATCCTCCAG CGCGGGGATC TCATGCTGGA GTTCTTCGCC CACCCCAACT TGTTTATTGC    1539

AGCTTATAAT GGTTACAAAT AAAGCAATAG CATCACAAAT TTCACAAATA AAGCATTTTT    1599

TTCACTGCAT TCTAGTTGTG GTTTGTCCAA ACTCATCAAT GTATCTTATC ATGTCTGTAT    1659

ACCGTCGACC TCTAGCTAGA GCTTGGCGTA ATCATGGTCA TAGCTGTTTC CTGTGTGAAA    1719

TTGTTATCCG CTCACAATTC CACACAACAT ACGAGCCGGA AGCATAAAGT GTAAAGCCTG    1779

GGGTGCCTAA TGAGTGAGCT AACTCACATT AATTGCGTTG CGCTCACTGC CCGCTTTCCA    1839

GTCGGGAAAC CTGTCGTGCC AGCTGCATTA ATGAATCGGC CAACGCGCGG GGAGAGGCGG    1899

TTTGCGTATT GGGCGCTCTT CCGCTTCCTC GCTCACTGAC TCGCTGCGCT CGGTCGTTCG    1959

GCTGCGGCGA GCGGTATCAG CTCACTCAAA GGCGGTAATA CGGTTATCCA CAGAATCAGG    2019

GGATAACGCA GGAAAGAACA TGTGAGCAAA AGGCCAGCAA AAGGCCAGGA ACCGTAAAAA    2079

GGCCGCGTTG CTGGCGTTTT TCCATAGGCT CCGCCCCCCT GACGAGCATC ACAAAAATCG    2139

ACGCTCAAGT CAGAGGTGGC GAAACCCGAC AGGACTATAA AGATACCAGG CGTTTCCCCC    2199

TGGAAGCTCC CTCGTGCGCT CTCCTGTTCC GACCCTGCCG CTTACCGGAT ACCTGTCCGC    2259

CTTTCTCCCT TCGGGAAGCG TGGCGCTTTC TCAATGCTCA CGCTGTAGGT ATCTCAGTTC    2319

GGTGTAGGTC GTTCGCTCCA AGCTGGGCTG TGTGCACGAA CCCCCCGTTC AGCCCGACCG    2379

CTGCGCCTTA TCCGGTAACT ATCGTCTTGA GTCCAACCCG GTAAGACACG ACTTATCGCC    2439

ACTGGCAGCA GCCACTGGTA ACAGGATTAG CAGAGCGAGG TATGTAGGCG GTGCTACAGA    2499

GTTCTTGAAG TGGTGGCCTA ACTACGGCTA CACTAGAAGG ACAGTATTTG GTATCTGCGC    2559

TCTGCTGAAG CCAGTTACCT TCGGAAAAAG AGTTGGTAGC TCTTGATCCG GCAAACAAAC    2619

CACCGCTGGT AGCGGTGGTT TTTTGTTTG CAAGCAGCAG ATTACGCGCA GAAAAAAAGG    2679

ATCTCAAGAA GATCCTTTGA TCTTTTCTAC GGGGTCTGAC GCTCAGTGGA ACGAAAACTC    2739

ACGTTAAGGG ATTTTGGTCA TGAGATTATC AAAAAGGATC TTCACCTAGA TCCTTTTAAA    2799

TTAAAAATGA AGTTTTAAAT CAATCTAAAG TATATATGAG TAAACTTGGT CTGACAGTTA    2859

CCAATGCTTA ATCAGTGAGG CACCTATCTC AGCGATCTGT CTATTTCGTT CATCCATAGT    2919

TGCCTGACTC CCCGTCGTGT AGATAACTAC GATACGGGAG GGCTTACCAT CTGGCCCCAG    2979

TGCTGCAATG ATACCGCGAG ACCCACGCTC ACCGGCTCCA GATTTATCAG CAATAAACCA    3039

GCCAGCCGGA AGGGCCGAGC GCAGAAGTGG TCCTGCAACT TTATCCGCCT CCATCCAGTC    3099

TATTAATTGT TGCCGGGAAG CTAGAGTAAG TAGTTCGCCA GTTAATAGTT TGCGCAACGT    3159

TGTTGCCATT GCTACAGGCA TCGTGGTGTC ACGCTCGTCG TTTGGTATGG CTTCATTCAG    3219

CTCCGGTTCC CAACGATCAA GGCGAGTTAC ATGATCCCCC ATGTTGTGCA AAAAAGCGGT    3279

TAGCTCCTTC GGTCCTCCGA TCGTTGTCAG AAGTAAGTTG GCCGCAGTGT TATCACTCAT    3339

GGTTATGGCA GCACTGCATA ATTCTCTTAC TGTCATGCCA TCCGTAAGAT GCTTTTCTGT    3399

GACTGGTGAG TACTCAACCA AGTCATTCTG AGAATAGTGT ATGCGGCGAC CGAGTTGCTC    3459

TTGCCCGGCG TCAATACGGG ATAATACCGC GCCACATAGC AGAACTTTAA AAGTGCTCAT    3519

CATTGGAAAA CGTTCTTCGG GGCGAAAACT CTCAAGGATC TTACCGCTGT TGAGATCCAG    3579

TTCGATGTAA CCCACTCGTG CACCCAACTG ATCTTCAGCA TCTTTTACTT TCACCAGCGT    3639

TTCTGGGTGA GCAAAAACAG GAAGGCAAAA TGCCGCAAAA AAGGGAATAA GGGCGACACG    3699

GAAATGTTGA ATACTCATAC TCTTCCTTTT TCAATATTAT TGAAGCATTT ATCAGGGTTA    3759
```

```
TTGTCTCATG AGCGGATACA TATTTGAATG TATTTAGAAA AATAAACAAA TAGGGGTTCC      3819

GCGCACATTT CCCCGAAAAG TGCCACCTGA CGTC                                 3853
```

(2) INFORMATION FOR SEQ ID NO:6:

(i) SEQUENCE CHARACTERISTICS:
        (A) LENGTH: 14 amino acids
        (B) TYPE: amino acid
        (D) TOPOLOGY: linear (ii) MOLECULE TYPE: protein (xi) SEQUENCE DESCRIPTION: SEQ ID NO:6:

```
Arg Cys Thr Gly Gln Ile Tyr Ala Leu Thr Leu Ile Ile Asp
 1               5                  10
```

(2) INFORMATION FOR SEQ ID NO:7:

(i) SEQUENCE CHARACTERISTICS:
        (A) LENGTH: 12 amino acids
        (B) TYPE: amino acid
        (D) TOPOLOGY: linear (ii) MOLECULE TYPE: protein (xi) SEQUENCE DESCRIPTION: SEQ ID NO:7:

```
Leu Leu Ile Val Ile Asn Tyr Gly Val Ile Ser Ser
 1               5                  10
```

(2) INFORMATION FOR SEQ ID NO:8:

(i) SEQUENCE CHARACTERISTICS:
        (A) LENGTH: 71 amino acids
        (B) TYPE: amino acid
        (D) TOPOLOGY: linear (ii) MOLECULE TYPE: protein (xi) SEQUENCE DESCRIPTION: SEQ ID NO:8:

```
Pro Ile Tyr Gly Val Pro Arg Tyr Ile Thr Tyr Gly Lys Trp Pro Ala
 1               5                  10                  15

Trp Leu Thr Ala Gln Arg Pro Pro Ile Asp Val Asn Asn Asp Val
                20                  25                  30

Cys Ser His Ser Asn Ala Asn Arg Asp Phe Pro Leu Thr Ser Met Gly
                35                  40                  45

Gly Leu Phe Thr Val Asn Cys Pro Leu Gly Ser Thr Ser Ser Val Ser
        50                  55                  60

Tyr Ala Lys Tyr Ala Pro Tyr
65                  70
```

(2) INFORMATION FOR SEQ ID NO:9:

(i) SEQUENCE CHARACTERISTICS:
        (A) LENGTH: 2 amino acids
        (B) TYPE: amino acid
        (D) TOPOLOGY: linear (ii) MOLECULE TYPE: protein (xi) SEQUENCE DESCRIPTION: SEQ ID NO:9:

```
Arg Gln
 1
```

(2) INFORMATION FOR SEQ ID NO:10:

```
    (i) SEQUENCE CHARACTERISTICS:
        (A) LENGTH: 1 amino acids
        (B) TYPE: amino acid
        (D) TOPOLOGY: linear (ii) MOLECULE TYPE: protein (xi) SEQUENCE DESCRIPTION: SEQ ID NO:10:

Arg
 1

(2) INFORMATION FOR SEQ ID NO:11:

(i) SEQUENCE CHARACTERISTICS:
        (A) LENGTH: 45 amino acids
        (B) TYPE: amino acid
        (D) TOPOLOGY: linear (ii) MOLECULE TYPE: protein (xi) SEQUENCE DESCRIPTION: SEQ ID NO:11:

Met Ala Arg Leu Ala Leu Cys Pro Val His Asp Leu Met Gly Leu Ser
 1               5                  10                  15

Tyr Leu Ala Val His Leu Arg Ile Ser His Arg Tyr Tyr His Gly Asp
                20                  25                  30

Ala Val Leu Ala Val His Gln Trp Ala Trp Ile Ala Val
            35                  40                  45

(2) INFORMATION FOR SEQ ID NO:12:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO:12:

Leu Thr Gly Ile Ser Lys Ser Pro Pro His
 1               5                  10

(2) INFORMATION FOR SEQ ID NO:13:

(i) SEQUENCE CHARACTERISTICS:
        (A) LENGTH: 18 amino acids
        (B) TYPE: amino acid
        (D) TOPOLOGY: linear (ii) MOLECULE TYPE: protein (xi) SEQUENCE DESCRIPTION: SEQ ID NO:13:

Arg Gln Trp Glu Phe Val Leu Ala Pro Lys Ser Thr Gly Leu Ser Lys
 1               5                  10                  15

Met Ser (2) INFORMATION FOR SEQ ID NO:14:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO:14:

Gln Leu Arg Pro Ile Asp Ala Asn Gly Arg
 1               5                  10
```

(2) INFORMATION FOR SEQ ID NO:15:

(i) SEQUENCE CHARACTERISTICS:
        (A) LENGTH: 15 amino acids
        (B) TYPE: amino acid
        (D) TOPOLOGY: linear (ii) MOLECULE TYPE: protein (xi) SEQUENCE DESCRIPTION: SEQ ID NO:15:

Arg Cys Thr Val Gly Gly Leu Tyr Lys Gln Ser Ser Leu Ala Asn
 1               5                  10                  15

(2) INFORMATION FOR SEQ ID NO:16:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO:16:

Arg Thr His Cys Leu Leu Ala Tyr Arg Asn
 1               5                  10

(2) INFORMATION FOR SEQ ID NO:17:

(i) SEQUENCE CHARACTERISTICS:
        (A) LENGTH: 1 amino acids
        (B) TYPE: amino acid
        (D) TOPOLOGY: linear (ii) MOLECULE TYPE: protein (xi) SEQUENCE DESCRIPTION: SEQ ID NO:17:

Leu
 1

(2) INFORMATION FOR SEQ ID NO:18:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO:18:

Cys His Leu Asn
 1

(2) INFORMATION FOR SEQ ID NO:19:

(i) SEQUENCE CHARACTERISTICS:
        (A) LENGTH: 4026 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 209..250

(ix) FEATURE:
        (A) NAME/KEY: CDS
        (B) LOCATION: 254..289

(ix) FEATURE:
    (A) NAME/KEY: CDS
    (B) LOCATION: 293..505

(ix) FEATURE:
    (A) NAME/KEY: CDS
    (B) LOCATION: 509..514

(ix) FEATURE:
    (A) NAME/KEY: CDS
    (B) LOCATION: 518..520

(ix) FEATURE:
    (A) NAME/KEY: CDS
    (B) LOCATION: 524..658

(ix) FEATURE:
    (A) NAME/KEY: CDS
    (B) LOCATION: 662..691

(ix) FEATURE:
    (A) NAME/KEY: CDS
    (B) LOCATION: 695..748

(ix) FEATURE:
    (A) NAME/KEY: CDS
    (B) LOCATION: 752..781

(ix) FEATURE:
    (A) NAME/KEY: CDS
    (B) LOCATION: 785..829

(ix) FEATURE:
    (A) NAME/KEY: CDS
    (B) LOCATION: 833..862

(ix) FEATURE:
    (A) NAME/KEY: CDS
    (B) LOCATION: 1305..1307

(ix) FEATURE:
    (A) NAME/KEY: CDS
    (B) LOCATION: 1311..1322

(xi) SEQUENCE DESCRIPTION: SEQ ID NO:19:

```
GACGGATCGG GAGATCTCCC GATCCCCTAT GGTCGACTCT CAGTACAATC TGCTCTGATG      60

CCGCATAGTT AAGCCAGTAT CTGCTCCCTG CTTGTGTGTT GGAGGTCGCT GAGTAGTGCG     120

CGAGCAAAAT TTAAGCTACA ACAAGGCAAG GCTTGACCGA CAATTGCATG AAGAATCTGC     180

TTAGGGTTAG GCGTTTTGCG CTGCTTCG CGA TGT ACG GGC CAG ATA TAC GCG        232
                                Arg Cys Thr Gly Gln Ile Tyr Ala
                                  1               5

TTG ACA TTG ATT ATT GAC TAG TTA TTA ATA GTA ATC AAT TAC GGG GTC       280
Leu Thr Leu Ile Ile Asp     Leu Leu Ile Val Ile Asn Tyr Gly Val
        10                    1               5

ATT AGT TCA TAG CCC ATA TAT GGA GTT CCG CGT TAC ATA ACT TAC GGT       328
Ile Ser Ser     Pro Ile Tyr Gly Val Pro Arg Tyr Ile Thr Tyr Gly
 10                 1               5                  10

AAA TGG CCC GCC TGG CTG ACC GCC CAA CGA CCC CCG CCC ATT GAC GTC       376
Lys Trp Pro Ala Trp Leu Thr Ala Gln Arg Pro Pro Pro Ile Asp Val
            15                  20              25

AAT AAT GAC GTA TGT TCC CAT AGT AAC GCC AAT AGG GAC TTT CCA TTG       424
Asn Asn Asp Val Cys Ser His Ser Asn Ala Asn Arg Asp Phe Pro Leu
        30              35              40

ACG TCA ATG GGT GGA CTA TTT ACG GTA AAC TGC CCA CTT GGC AGT ACA       472
Thr Ser Met Gly Gly Leu Phe Thr Val Asn Cys Pro Leu Gly Ser Thr
 45              50              55                  60

TCA AGT GTA TCA TAT GCC AAG TAC GCC CCC TAT TGA CGT CAA                514
Ser Ser Val Ser Tyr Ala Lys Tyr Ala Pro Tyr     Arg Gln
```

-continued

```
                  65                    70                  1
TGA CGG TAA ATG GCC CGC CTG GCA TTA TGC CCA GTA CAT GAC CTT ATG      562
    Arg     Met Ala Arg Leu Ala Leu Cys Pro Val His Asp Leu Met
     1       1               5                  10

GGA CTT TCC TAC TTG GCA GTA CAT CTA CGT ATT AGT CAT CGC TAT TAC      610
Gly Leu Ser Tyr Leu Ala Val His Leu Arg Ile Ser His Arg Tyr Tyr
         15                  20                  25

CAT GGT GAT GCG GTT TTG GCA GTA CAT CAA TGG GCG TGG ATA GCG GTT      658
His Gly Asp Ala Val Leu Ala Val His Gln Trp Ala Trp Ile Ala Val
 30                  35                  40                  45

TGA CTC ACG GGG ATT TCC AAG TCT CCA CCC CAT TGA CGT CAA TGG GAG      706
    Leu Thr Gly Ile Ser Lys Ser Pro Pro His     Arg Gln Trp Glu
     1               5                  10       1

TTT GTT TTG GCA CCA AAA TCA ACG GGA CTT TCC AAA ATG TCG              748
Phe Val Leu Ala Pro Lys Ser Thr Gly Leu Ser Lys Met Ser
 5              10                  15

TAA CAA CTC CGC CCC ATT GAC GCA AAT GGG CGG TAG GCG TGT ACG GTG      796
    Gln Leu Arg Pro Ile Asp Ala Asn Gly Arg     Ala Cys Thr Val
     1               5                  10       1

GGA GGT CTA TAT AAG CAG AGC TCT CTG GCT AAC TAG AGA ACC CAC TGC      844
Gly Gly Leu Tyr Lys Gln Ser Ser Leu Ala Asn     Arg Thr His Cys
 5              10                  15           1

TTA CTG GCT TAT CGA AAT TAATACGACT CACTATAGGG AGACCCAAGC             892
Leu Leu Ala Tyr Arg Asn
 5              10

TTCGCGCGGG TACCACTCTC TTCCGCATCG CTGTCTGCGA GGGCCAGCTG TTGGGCTCGC    952

GGTTGAGGAC AAACTCTTCG CGGTCTTTCC AGTACTCTTG GATCGGAAAC CCGTCGGCCT    1012

CCGAACGGTA CTCCGCCACC GAGGGACCTG AGCGAGTCCG CATCGACCGG ATCGGAAAAC    1072

CTCTCGAGGA ACTGAAAAAC CAGAAAGTTA ACTGGTAAGT TTAGTCTTTT TGTCTTTTTA    1132

TTTCAGGTCC CGGATCCGGT GGTGGTGCAA ATCAAAGAAC TGCTCCTCAG TGGATGTTGC    1192

CTTTACTTCT AGGCCTGTAC GGAAGTGTTA CTTCTGCTCT AAAAGCTGCG GAATTGTACC    1252

CGCGGCCGCT GCAGTCTAGA CGAATTCGCG TACGATATCG ATGGGCCCTA TT CTA        1307
                                                        Leu
                                                         1

TAG TGT CAC CTA AAT GCTAGAGCTC GCTGATCAGC CTCGACTGTG CCTTCTAGTT      1362
    Cys His Leu Asn
     1

GCCAGCCATC TGTTGTTTGC CCCTCCCCCG TGCCTTCCTT GACCCTGGAA GGTGCCACTC    1422

CCACTGTCCT TTCCTAATAA AATGAGGAAA TTGCATCGCA TTGTCTGAGT AGGTGTCATT    1482

CTATTCTGGG GGGTGGGGTG GGGCAGGACA GCAAGGGGGA GGATTGGGAA GACAATAGCC    1542

GAAATGACCG ACCAAGCGAC GCCCAACCTG CCATCACGAG ATTTCGATTC CACCGCCGCC    1602

TTCTATGAAA GGTTGGGCTT CGGAATCGTT TTCCGGACG CCGGCTGGAT GATCCTCCAG     1662

CGCGGGATC TCATGCTGGA GTTCTTCGCC CACCCCAACT TGTTTATTGC AGCTTATAAT     1722

GGTTACAAAT AAAGCAATAG CATCACAAAT TTCACAAATA AAGCATTTTT TTCACTGCAT    1782

TCTAGTTGTG GTTTGTCCAA ACTCATCAAT GTATCTTATC ATGTCTGTAT ACCGTCGACC    1842

TCTAGCTAGA GCTTGGCGTA ATCATGGTCA TAGCTGTTTC CTGTGTGAAA TTGTTATCCG    1902

CTCACAATTC CACACAACAT ACGAGCCGGA AGCATAAAGT GTAAAGCCTG GGGTGCCTAA    1962

TGAGTGAGCT AACTCACATT AATTGCGTTG CGCTCACTGC CCGCTTTCCA GTCGGGAAAC    2022

CTGTCGTGCC AGCTGCATTA ATGAATCGGC CAACGCGCGG GGAGAGGCGG TTTGCGTATT    2082

GGGCGCTCTT CCGCTTCCTC GCTCACTGAC TCGCTGCGCT CGGTCGTTCG GCTGCGGCGA    2142
```

-continued

```
GCGGTATCAG CTCACTCAAA GGCGGTAATA CGGTTATCCA CAGAATCAGG GGATAACGCA      2202

GGAAAGAACA TGTGAGCAAA AGGCCAGCAA AAGGCCAGGA ACCGTAAAAA GGCCGCGTTG      2262

CTGGCGTTTT TCCATAGGCT CCGCCCCCCT GACGAGCATC ACAAAAATCG ACGCTCAAGT      2322

CAGAGGTGGC GAAACCCGAC AGGACTATAA AGATACCAGG CGTTTCCCCC TGGAAGCTCC      2382

CTCGTGCGCT CTCCTGTTCC GACCCTGCCG CTTACCGGAT ACCTGTCCGC CTTTCTCCCT      2442

TCGGGAAGCG TGGCGCTTTC TCAATGCTCA CGCTGTAGGT ATCTGAGTTC GGTGTAGGTC      2502

GTTCGCTCCA AGCTGGGCTG TGTGCACGAA CCCCCCGTTC AGCCCGACCG CTGCGCCTTA      2562

TCCGGTAACT ATCGTCTTGA GTCCAACCCG GTAAGACACG ACTTATCGCC ACTGGCAGCA      2622

GCCACTGGTA ACAGGATTAG CAGAGCGAGG TATGTAGGCG GTGCTACAGA GTTCTTGAAG      2682

TGGTGGCCTA ACTACGGCTA CACTAGAAGG ACAGTATTTG GTATCTGCGC TCTGCTGAAG      2742

CCAGTTACCT TCGGAAAAAG AGTTGGTAGC TCTTGATCCG GCAAACAAAC CACCGCTGGT      2802

AGCGGTGGTT TTTTTGTTTG CAAGCAGCAG ATTACGCGCA GAAAAAAGG ATCTCAAGAA       2862

GATCCTTTGA TCTTTTCTAC GGGGTCTGAC GCTCAGTGGA ACGAAAACTC ACGTTAAGGG      2922

ATTTTGGTCA TGAGATTATC AAAAAGGATC TTCACCTAGA TCCTTTTAAA TTAAAAATGA      2982

AGTTTTAAAT CAATCTAAAG TATATATGAG TAAACTTGGT CTGACAGTTA CCAATGCTTA      3042

ATCAGTGAGG CACCTATCTC AGCGATCTGT CTATTTCGTT CATCCATAGT TGCCTGACTC      3102

CCCGTCGTGT AGATAACTAC GATACGGGAG GGCTTACCAT CTGGCCCCAG TGCTGCAATG      3162

ATACCGCGAG ACCCACGCTC ACCGGCTCCA GATTTATCAG CAATAAACCA GCCAGCCGGA      3222

AGGGCCGAGC GCAGAAGTGG TCCTGCAACT TTATCCGCCT CCATCCAGTC TATTAATTGT      3282

TGCCGGGAAG CTAGAGTAAG TAGTTCGCCA GTTAATAGTT TGCGCAACGT TGTTGCCATT      3342

GCTACAGGCA TCGTGGTGTC ACGCTCGTCG TTTGGTATGG CTTCATTCAG CTCCGGTTCC      3402

CAACGATCAA GGCGAGTTAC ATGATCCCCC ATGTTGTGCA AAAAAGCGGT TAGCTCCTTC      3462

GGTCCTCCGA TCGTTGTCAG AAGTAAGTTG GCCGCAGTGT TATCACTCAT GGTTATGGCA      3522

GCACTGCATA ATTCTCTTAC TGTCATGCCA TCCGTAAGAT GCTTTTCTGT GACTGGTGAG      3582

TACTCAACCA AGTCATTCTG AGAATAGTGT ATGCGGCGAC CGAGTTGCTC TTGCCCGGCG      3642

TCAATACGGG ATAATACCGC GCCACATAGC AGAACTTTAA AAGTGCTCAT CATTGGAAAA      3702

CGTTCTTCGG GGCGAAAACT CTCAAGGATC TTACCGCTGT TGAGATCCAG TTCGATGTAA      3762

CCCACTCGTG CACCCAACTG ATCTTCAGCA TCTTTTACTT TCACCAGCGT TTCTGGGTGA      3822

GCAAAAACAG GAAGGCAAAA TGCCGCAAAA AAGGGAATAA GGGCGACACG GAAATGTTGA      3882

ATACTCATAC TCTTCCTTTT TCAATATTAT TGAAGCATTT ATCAGGGTTA TTGTCTCATG      3942

AGCGGATACA TATTTGAATG TATTTAGAAA AATAAACAAA TAGGGGTTCC GCGCACATTT      4002

CCCCGAAAAG TGCCACCTGA CGTC                                              4026
```

(2) INFORMATION FOR SEQ ID NO:20:

(i) SEQUENCE CHARACTERISTICS:
        (A) LENGTH: 14 amino acids
        (B) TYPE: amino acid
        (D) TOPOLOGY: linear (ii) MOLECULE TYPE: protein (xi) SEQUENCE DESCRIPTION: SEQ ID NO:20:

```
Arg Cys Thr Gly Gln Ile Tyr Ala Leu Thr Leu Ile Ile Asp
 1               5                  10
```

(2) INFORMATION FOR SEQ ID NO:21:

(i) SEQUENCE CHARACTERISTICS:
        (A) LENGTH: 12 amino acids
        (B) TYPE: amino acid
        (D) TOPOLOGY: linear (ii) MOLECULE TYPE: protein (xi) SEQUENCE DESCRIPTION: SEQ ID NO:21:

```
Leu Leu Ile Val Ile Asn Tyr Gly Val Ile Ser Ser
 1               5                  10
```

(2) INFORMATION FOR SEQ ID NO:22:

(i) SEQUENCE CHARACTERISTICS:
        (A) LENGTH: 71 amino acids
        (B) TYPE: amino acid
        (D) TOPOLOGY: linear (ii) MOLECULE TYPE: protein (xi) SEQUENCE DESCRIPTION: SEQ ID NO:22:

```
Pro Ile Tyr Gly Val Pro Arg Tyr Ile Thr Tyr Gly Lys Trp Pro Ala
 1               5                  10                  15

Trp Leu Thr Ala Gln Arg Pro Pro Ile Asp Val Asn Asn Asp Val
                20                  25                  30

Cys Ser His Ser Asn Ala Asn Arg Asp Phe Pro Leu Thr Ser Met Gly
            35                  40                  45

Gly Leu Phe Thr Val Asn Cys Pro Leu Gly Ser Thr Ser Ser Val Ser
        50                  55                  60

Tyr Ala Lys Tyr Ala Pro Tyr
 65              70
```

(2) INFORMATION FOR SEQ ID NO:23:

(i) SEQUENCE CHARACTERISTICS:
        (A) LENGTH: 2 amino acids
        (B) TYPE: amino acid
        (D) TOPOLOGY: linear (ii) MOLECULE TYPE: protein (xi) SEQUENCE DESCRIPTION: SEQ ID NO:23:

```
Arg Gln
 1
```

(2) INFORMATION FOR SEQ ID NO:24:

(i) SEQUENCE CHARACTERISTICS:
        (A) LENGTH: 1 amino acids
        (B) TYPE: amino acid
        (D) TOPOLOGY: linear (ii) MOLECULE TYPE: protein (xi) SEQUENCE DESCRIPTION: SEQ ID NO:24:

```
Arg
 1
```

(2) INFORMATION FOR SEQ ID NO:25:

(i) SEQUENCE CHARACTERISTICS:
        (A) LENGTH: 45 amino acids
        (B) TYPE: amino acid (D) TOPOLOGY: linear (ii) MOLECULE TYPE: protein (xi) SEQUENCE DESCRIPTION: SEQ ID NO:25:

Met Ala Arg Leu Ala Leu Cys Pro Val His Asp Leu Met Gly Leu Ser
 1               5                  10                  15

Tyr Leu Ala Val His Leu Arg Ile Ser His Arg Tyr Tyr His Gly Asp
            20                  25                  30

Ala Val Leu Ala Val His Gln Trp Ala Trp Ile Ala Val
        35                  40                  45

(2) INFORMATION FOR SEQ ID NO:26:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO:26:

Leu Thr Gly Ile Ser Lys Ser Pro Pro His
 1               5                  10

(2) INFORMATION FOR SEQ ID NO:27:

(i) SEQUENCE CHARACTERISTICS:
        (A) LENGTH: 18 amino acids
        (B) TYPE: amino acid
        (D) TOPOLOGY: linear (ii) MOLECULE TYPE: protein (xi) SEQUENCE DESCRIPTION: SEQ ID NO:27:

Arg Gln Trp Glu Phe Val Leu Ala Pro Lys Ser Thr Gly Leu Ser Lys
 1               5                  10                  15

Met Ser (2) INFORMATION FOR SEQ ID NO:28:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO:28:

Gln Leu Arg Pro Ile Asp Ala Asn Gly Arg
 1               5                  10

(2) INFORMATION FOR SEQ ID NO:29:

(i) SEQUENCE CHARACTERISTICS:
        (A) LENGTH: 15 amino acids
        (B) TYPE: amino acid
        (D) TOPOLOGY: linear (ii) MOLECULE TYPE: protein (xi) SEQUENCE DESCRIPTION: SEQ ID NO:29:

Ala Cys Thr Val Gly Gly Leu Tyr Lys Gln Ser Ser Leu Ala Asn
 1               5                  10                  15

(2) INFORMATION FOR SEQ ID NO:30:

```
        (i) SEQUENCE CHARACTERISTICS:
             (A) LENGTH: 10 amino acids
             (B) TYPE: amino acid
             (D) TOPOLOGY: linear (ii) MOLECULE TYPE: protein (xi) SEQUENCE DESCRIPTION: SEQ ID NO:30:

Arg Thr His Cys Leu Leu Ala Tyr Arg Asn
 1               5                  10

(2) INFORMATION FOR SEQ ID NO:31:

(i) SEQUENCE CHARACTERISTICS:
             (A) LENGTH: 1 amino acids
             (B) TYPE: amino acid
             (D) TOPOLOGY: linear (ii) MOLECULE TYPE: protein (xi) SEQUENCE DESCRIPTION: SEQ ID NO:31:

Leu
 1

(2) INFORMATION FOR SEQ ID NO:32:

(i) SEQUENCE CHARACTERISTICS:
             (A) LENGTH: 4 amino acids
             (B) TYPE: amino acid
             (D) TOPOLOGY: linear (ii) MOLECULE TYPE: protein (xi) SEQUENCE DESCRIPTION: SEQ ID NO:32:

Cys His Leu Asn
 1

(2) INFORMATION FOR SEQ ID NO:33:

(i) SEQUENCE CHARACTERISTICS:
             (A) LENGTH: 4249 base pairs
             (B) TYPE: nucleic acid
             (C) STRANDEDNESS: single
             (D) TOPOLOGY: linear (ii) MOLECULE TYPE: DNA (genomic)

(ix) FEATURE:
             (A) NAME/KEY: CDS
             (B) LOCATION: 209..250

(ix) FEATURE:
             (A) NAME/KEY: CDS
             (B) LOCATION: 254..289

(ix) FEATURE:
             (A) NAME/KEY: CDS
             (B) LOCATION: 293..505

(ix) FEATURE:
             (A) NAME/KEY: CDS
             (B) LOCATION: 509..514

(ix) FEATURE:
             (A) NAME/KEY: CDS
             (B) LOCATION: 518..520

(ix) FEATURE:
             (A) NAME/KEY: CDS
             (B) LOCATION: 524..658

(ix) FEATURE:
```

(A) NAME/KEY: CDS
                (B) LOCATION: 662..691

(ix) FEATURE:
                (A) NAME/KEY: CDS
                (B) LOCATION: 695..748

(ix) FEATURE:
                (A) NAME/KEY: CDS
                (B) LOCATION: 752..781

(ix) FEATURE:
                (A) NAME/KEY: CDS
                (B) LOCATION: 785..829

(ix) FEATURE:
                (A) NAME/KEY: CDS
                (B) LOCATION: 833..862

(ix) FEATURE:
                (A) NAME/KEY: CDS
                (B) LOCATION: 1528..1530

(ix) FEATURE:
                (A) NAME/KEY: CDS
                (B) LOCATION: 1534..1545

(xi) SEQUENCE DESCRIPTION: SEQ ID NO:33:

```
GACGGATCGG GAGATCTCCC GATCCCCTAT GGTCGACTCT CAGTACAATC TGCTCTGATG        60

CCGCATAGTT AAGCCAGTAT CTGCTCCCTG CTTGTGTGTT GGAGGTCGCT GAGTAGTGCG       120

CGAGCAAAAT TTAAGCTACA ACAAGGCAAG CTTGACCGA CAATTGCATG AAGAATCTGC        180

TTAGGGTTAG GCGTTTTGCG CTGCTTCG CGA TGT ACG GGC CAG ATA TAC GCG          232
                                Arg Cys Thr Gly Gln Ile Tyr Ala
                                  1               5

TTG ACA TTG ATT ATT GAC TAG TTA TTA ATA GTA ATC AAT TAC GGG GTC         280
Leu Thr Leu Ile Ile Asp     Leu Leu Ile Val Ile Asn Tyr Gly Val
        10                    1               5

ATT AGT TCA TAG CCC ATA TAT GGA GTT CCG CGT TAC ATA ACT TAC GGT         328
Ile Ser Ser     Pro Ile Tyr Gly Val Pro Arg Tyr Ile Thr Tyr Gly
    10            1               5                   10

AAA TGG CCC GCC TGG CTG ACC GCC CAA CGA CCC CCG CCC ATT GAC GTC         376
Lys Trp Pro Ala Trp Leu Thr Ala Gln Arg Pro Pro Pro Ile Asp Val
            15              20              25

AAT AAT GAC GTA TGT TCC CAT AGT AAC GCC AAT AGG GAC TTT CCA TTG         424
Asn Asn Asp Val Cys Ser His Ser Asn Ala Asn Arg Asp Phe Pro Leu
        30              35              40

ACG TCA ATG GGT GGA CTA TTT ACG GTA AAC TGC CCA CTT GGC AGT ACA         472
Thr Ser Met Gly Gly Leu Phe Thr Val Asn Cys Pro Leu Gly Ser Thr
    45              50              55              60

TCA AGT GTA TCA TAT GCC AAG TAC GCC CCC TAT TGA CGT CAA                 514
Ser Ser Val Ser Tyr Ala Lys Tyr Ala Pro Tyr     Arg Gln
                65              70                1

TGA CGG TAA ATG GCC CGC CTG GCA TTA TGC CCA GTA CAT GAC CTT ATG         562
    Arg     Met Ala Arg Leu Ala Leu Cys Pro Val His Asp Leu Met
     1       1           5                       10

GGA CTT TCC TAC TTG GCA GTA CAT CTA CGT ATT AGT CAT CGC TAT TAC         610
Gly Leu Ser Tyr Leu Ala Val His Leu Arg Ile Ser His Arg Tyr Tyr
        15              20              25

CAT GGT GAT GCG GTT TTG GCA GTA CAT CAA TGG GCG TGG ATA GCG GTT         658
His Gly Asp Ala Val Leu Ala Val His Gln Trp Ala Trp Ile Ala Val
        30              35              40              45

TGA CTC ACG GGG ATT TCC AAG TCT CCA CCC CAT TGA CGT CAA TGG GAG         706
    Leu Thr Gly Ile Ser Lys Ser Pro Pro His     Arg Gln Trp Glu
         1           5               10           1
```

```
TTT GTT TTG GCA CCA AAA TCA ACG GGA CTT TCC AAA ATG TCG             748
Phe Val Leu Ala Pro Lys Ser Thr Gly Leu Ser Lys Met Ser
 5                  10                  15

TAA CAA CTC CGC CCC ATT GAC GCA AAT GGG CGG TAG GCG TGT ACG GTG     796
    Gln Leu Arg Pro Ile Asp Ala Asn Gly Arg     Ala Cys Thr Val
     1               5                  10       1

GGA GGT CTA TAT AAG CAG AGC TCT CTG GCT AAC TAG AGA ACC CAC TGC     844
Gly Gly Leu Tyr Lys Gln Ser Ser Leu Ala Asn     Arg Thr His Cys
 5                  10                  15       1

TTA CTG GCT TAT CGA AAT TAATACGACT CACTATAGGG AGACCCAAGC            892
Leu Leu Ala Tyr Arg Asn
 5                  10

TTCGCGCGGG TACCACTCTC TTCCGCATCG CTGTCTGCGA GGGCCAGCTG TTGGGCTCGC   952
GGTTGAGGAC AAACTCTTCG CGGTCTTTCC AGTACTCTTG GATCGGAAAC CCGTCGGCCT  1012
CCGAACGGTA CTCCGCCACC GAGGGACCTG AGCGAGTCCG CATCGACCGG ATCGGAAAAC  1072
CTCTCGAGGA ACTGAAAAAC CAGAAAGTTA ACTGGTAAGT TTAGTCTTTT TGTCTTTTTA  1132
TTTCAGGTCC CGGATCTGAG TTAGGGCGGG ACATGGGCGG AGTTAGGGGC GGGACTATGG  1192
TTGCTGACTA ATTGAGATGC ATGCTTTGCA TACTTCTGCC TGCTGGGGAG CCTGGGGACT  1252
TTCCACACCT GGTTGCTGAC TAATTGAGAT GCATGCTTTG CATACTTCTG CCTGCTGGGG  1312
AGCCTGGGGA CTTTCCACAC CCTAACTGAC ACACATTCCA CAGCTGGTTC TTTCAGATCC  1372
GGTGGTGGTG CAAATCAAAG AACTGCTCCT CAGTGGATGT TGCCTTTACT TCTAGGCCTG  1432
TACGGAAGTG TTACTTCTGC TCTAAAAGCT GCGGAATTGT ACCCGCGGCC GCTGCAGTCT  1492
AGACGAATTC GCGTACGATA TCGATGGGCC CTATT CTA TAG TGT CAC CTA AAT    1545
                                       Leu     Cys His Leu Asn
                                        1       1

GCTAGAGCTC GCTGATCAGC CTCGACTGTG CCTTCTAGTT GCCAGCCATC TGTTGTTTGC  1605
CCCTCCCCCG TGCCTTCCTT GACCCTGGAA GGTGCCACTC CCACTGTCCT TTCCTAATAA  1665
AATGAGGAAA TTGCATCGCA TTGTCTGAGT AGGTGTCATT CTATTCTGGG GGTGGGGTG   1725
GGGCAGGACA GCAAGGGGGA GGATTGGGAA GACAATAGCC GAAATGACCG ACCAAGCGAC  1785
GCCCAACCTG CCATCACGAG ATTTCGATTC CACCGCCGCC TTCTATGAAA GGTTGGGCTT  1845
CGGAATCGTT TTCCGGGACG CCGGCTGGAT GATCCTCCAG CGCGGGGATC TCATGCTGGA  1905
GTTCTTCGCC CACCCCAACT TGTTTATTGC AGCTTATAAT GGTTACAAAT AAAGCAATAG  1965
CATCACAAAT TTCACAAATA AAGCATTTTT TCACTGCAT TCTAGTTGTG GTTTGTCCAA   2025
ACTCATCAAT GTATCTTATC ATGTCTGTAT ACCGTCGACC TCTAGCTAGA GCTTGGCGTA  2085
ATCATGGTCA TAGCTGTTTC CTGTGTGAAA TTGTTATCCG CTCACAATTC CACACAACAT  2145
ACGAGCCGGA AGCATAAAGT GTAAAGCCTG GGGTGCCTAA TGAGTGAGCT AACTCACATT  2205
AATTGCGTTG CGCTCACTGC CCGCTTTCCA GTCGGGAAAC CTGTCGTGCC AGCTGCATTA  2265
ATGAATCGGC CAACGCGCGG GGAGAGGCGG TTTGCGTATT GGGCGCTCTT CCGCTTCCTC  2325
GCTCACTGAC TCGCTGCGCT CGGTCGTTCG GCTGCGGCGA GCGGTATCAG CTCACTCAAA  2385
GGCGGTAATA CGGTTATCCA CAGAATCAGG GGATAACGCA GGAAAGAACA TGTGAGCAAA  2445
AGGCCAGCAA AAGGCAGGA ACCGTAAAAA GGCCGCGTTG CTGGCGTTTT TCCATAGGCT   2505
CCGCCCCCCT GACGAGCATC ACAAAAATCG ACGCTCAAGT CAGAGGTGGC GAAACCCGAC  2565
AGGACTATAA AGATACCAGG CGTTTCCCCC TGGAAGCTCC CTCGTGCGCT CTCCTGTTCC  2625
GACCCTGCCG CTTACCGGAT ACCTGTCCGC CTTTCTCCCT TCGGGAAGCG TGGCGCTTTC  2685
TCAATGCTCA CGCTGTAGGT ATCTCAGTTC GGTGTAGGTC GTTCGCTCCA AGCTGGGCTG  2745
```

-continued

```
TGTGCACGAA CCCCCCGTTC AGCCCGACCG CTGCGCCTTA TCCGGTAACT ATCGTCTTGA      2805

GTCCAACCCG GTAAGACACG ACTTATCGCC ACTGGCAGCA GCCACTGGTA ACAGGATTAG      2865

CAGAGCGAGG TATGTAGGCG GTGCTACAGA GTTCTTGAAG TGGTGGCCTA ACTACGGCTA      2925

CACTAGAAGG ACAGTATTTG GTATCTGCGC TCTGCTGAAG CCAGTTACCT TCGGAAAAAG      2985

AGTTGGTAGC TCTTGATCCG GCAAACAAAC CACCGCTGGT AGCGGTGGTT TTTTTGTTTG      3045

CAAGCAGCAG ATTACGCGCA GAAAAAAGG ATCTCAAGAA GATCCTTTGA TCTTTTCTAC       3105

GGGGTCTGAC GCTCAGTGGA ACGAAAACTC ACGTTAAGGG ATTTTGGTCA TGAGATTATC     3165

AAAAAGGATC TTCACCTAGA TCCTTTTAAA TTAAAAATGA AGTTTTAAAT CAATCTAAAG     3225

TATATATGAG TAAACTTGGT CTGACAGTTA CCAATGCTTA ATCAGTGAGG CACCTATCTC     3285

AGCGATCTGT CTATTTCGTT CATCCATAGT TGCCTGACTC CCCGTCGTGT AGATAACTAC     3345

GATACGGGAG GGCTTACCAT CTGGCCCCAG TGCTGCAATG ATACCGCGAG ACCCACGCTC     3405

ACCGGCTCCA GATTTATCAG CAATAAACCA GCCAGCCGGA AGGGCCGAGC GCAGAAGTGG     3465

TCCTGCAACT TTATCCGCCT CCATCCAGTC TATTAATTGT TGCCGGGAAG CTAGAGTAAG     3525

TAGTTCGCCA GTTAATAGTT TGCGCAACGT TGTTGCCATT GCTACAGGCA TCGTGGTGTC     3585

ACGCTCGTCG TTTGGTATGG CTTCATTCAG CTCCGGTTCC CAACGATCAA GGCGAGTTAC     3645

ATGATCCCCC ATGTTGTGCA AAAAAGCGGT TAGCTCCTTC GGTCCTCCGA TCGTTGTCAG     3705

AAGTAAGTTG GCCGCAGTGT TATCACTCAT GGTTATGGCA GCACTGCATA ATTCTCTTAC     3765

TGTCATGCCA TCCGTAAGAT GCTTTTCTGT GACTGGTGAG TACTCAACCA AGTCATTCTG     3825

AGAATAGTGT ATGCGGCGAC CGAGTTGCTC TTGCCCGGCG TCAATACGGG ATAATACCGC     3885

GCCACATAGC AGAACTTTAA AAGTGCTCAT CATTGGAAAA CGTTCTTCGG GGCGAAAACT     3945

CTCAAGGATC TTACCGCTGT TGAGATCCAG TTCGATGTAA CCCACTCGTG CACCCAACTG     4005

ATCTTCAGCA TCTTTTACTT TCACCAGCGT TTCTGGGTGA GCAAAAACAG GAAGGCAAAA     4065

TGCCGCAAAA AAGGGAATAA GGGCGACACG GAAATGTTGA ATACTCATAC TCTTCCTTTT     4125

TCAATATTAT TGAAGCATTT ATCAGGGTTA TTGTCTCATG AGCGGATACA TATTTGAATG     4185

TATTTAGAAA AATAAACAAA TAGGGGTTCC GCGCACATTT CCCCGAAAAG TGCCACCTGA     4245

CGTC                                                                 4249
```

(2) INFORMATION FOR SEQ ID NO:34:

(i) SEQUENCE CHARACTERISTICS:
        (A) LENGTH: 14 amino acids
        (B) TYPE: amino acid
        (D) TOPOLOGY: linear (ii) MOLECULE TYPE: protein (xi) SEQUENCE DESCRIPTION: SEQ ID NO:34:

```
Arg Cys Thr Gly Gln Ile Tyr Ala Leu Thr Leu Ile Ile Asp
 1               5                  10
```

(2) INFORMATION FOR SEQ ID NO:35:

(i) SEQUENCE CHARACTERISTICS:
        (A) LENGTH: 12 amino acids
        (B) TYPE: amino acid
        (D) TOPOLOGY: linear (ii) MOLECULE TYPE: protein (xi) SEQUENCE DESCRIPTION: SEQ ID NO:35:

-continued

```
Leu Leu Ile Val Ile Asn Tyr Gly Val Ile Ser Ser
 1               5                  10
```

(2) INFORMATION FOR SEQ ID NO:36:

(i) SEQUENCE CHARACTERISTICS:
        (A) LENGTH: 71 amino acids
        (B) TYPE: amino acid
        (D) TOPOLOGY: linear (ii) MOLECULE TYPE: protein (xi) SEQUENCE DESCRIPTION: SEQ ID NO:36:

```
Pro Ile Tyr Gly Val Pro Arg Tyr Ile Thr Tyr Gly Lys Trp Pro Ala
 1               5                  10                  15

Trp Leu Thr Ala Gln Arg Pro Pro Ile Asp Val Asn Asn Asp Val
                20                  25                  30

Cys Ser His Ser Asn Ala Asn Arg Asp Phe Pro Leu Thr Ser Met Gly
                35                  40                  45

Gly Leu Phe Thr Val Asn Cys Pro Leu Gly Ser Thr Ser Ser Val Ser
                50                  55                  60

Tyr Ala Lys Tyr Ala Pro Tyr
65                  70
```

(2) INFORMATION FOR SEQ ID NO:37:

(i) SEQUENCE CHARACTERISTICS:
        (A) LENGTH: 2 amino acids
        (B) TYPE: amino acid
        (D) TOPOLOGY: linear (ii) MOLECULE TYPE: protein (xi) SEQUENCE DESCRIPTION: SEQ ID NO:37:

```
Arg Gln
 1
```

(2) INFORMATION FOR SEQ ID NO:38:

(i) SEQUENCE CHARACTERISTICS:
        (A) LENGTH: 1 amino acids
        (B) TYPE: amino acid
        (D) TOPOLOGY: linear (ii) MOLECULE TYPE: protein (xi) SEQUENCE DESCRIPTION: SEQ ID NO:38:

```
Arg
 1
```

(2) INFORMATION FOR SEQ ID NO:39:

(i) SEQUENCE CHARACTERISTICS:
        (A) LENGTH: 45 amino acids
        (B) TYPE: amino acid
        (D) TOPOLOGY: linear (ii) MOLECULE TYPE: protein (xi) SEQUENCE DESCRIPTION: SEQ ID NO:39:

```
Met Ala Arg Leu Ala Leu Cys Pro Val His Asp Leu Met Gly Leu Ser
 1               5                  10                  15

Tyr Leu Ala Val His Leu Arg Ile Ser His Arg Tyr Tyr His Gly Asp
                20                  25                  30
```

```
Ala Val Leu Ala Val His Gln Trp Ala Trp Ile Ala Val
         35                  40                  45

(2) INFORMATION FOR SEQ ID NO:40:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO:40:

Leu Thr Gly Ile Ser Lys Ser Pro Pro His
  1               5                  10

(2) INFORMATION FOR SEQ ID NO:41:

(i) SEQUENCE CHARACTERISTICS:
        (A) LENGTH: 18 amino acids
        (B) TYPE: amino acid
        (D) TOPOLOGY: linear (ii) MOLECULE TYPE: protein (xi) SEQUENCE DESCRIPTION: SEQ ID NO:41:

Arg Gln Trp Glu Phe Val Leu Ala Pro Lys Ser Thr Gly Leu Ser Lys
  1               5                  10                  15

Met Ser (2) INFORMATION FOR SEQ ID NO:42:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO:42:

Gln Leu Arg Pro Ile Asp Ala Asn Gly Arg
  1               5                  10

(2) INFORMATION FOR SEQ ID NO:43:

(i) SEQUENCE CHARACTERISTICS:
        (A) LENGTH: 15 amino acids
        (B) TYPE: amino acid
        (D) TOPOLOGY: linear (ii) MOLECULE TYPE: protein (xi) SEQUENCE DESCRIPTION: SEQ ID NO:43:

Ala Cys Thr Val Gly Gly Leu Tyr Lys Gln Ser Ser Leu Ala Asn
  1               5                  10                  15

(2) INFORMATION FOR SEQ ID NO:44:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO:44:

Arg Thr His Cys Leu Leu Ala Tyr Arg Asn
  1               5                  10
```

```
(2) INFORMATION FOR SEQ ID NO:45:

(i) SEQUENCE CHARACTERISTICS:
        (A) LENGTH: 1 amino acids
        (B) TYPE: amino acid
        (D) TOPOLOGY: linear (ii) MOLECULE TYPE: protein (xi) SEQUENCE DESCRIPTION: SEQ ID NO:45:

Leu
 1

(2) INFORMATION FOR SEQ ID NO:46:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO:46:

Cys His Leu Asn
```